United States Patent
Suga et al.

(10) Patent No.: US 10,197,567 B2
(45) Date of Patent: Feb. 5, 2019

(54) AZOLINE COMPOUND AND AZOLE COMPOUND LIBRARY AND METHOD FOR PRODUCING SAME

(75) Inventors: Hiroaki Suga, Tokyo (JP); Yuki Goto, Tokyo (JP); Yumi Ito, Tokyo (JP)

(73) Assignee: The University of Tokyo, Tokyo (JP)

( * ) Notice: Subject to any disclaimer, the term of this patent is extended or adjusted under 35 U.S.C. 154(b) by 1276 days.

(21) Appl. No.: 14/003,506

(22) PCT Filed: Mar. 9, 2012

(86) PCT No.: PCT/JP2012/056181
§ 371 (c)(1),
(2), (4) Date: Nov. 15, 2013

(87) PCT Pub. No.: WO2012/121392
PCT Pub. Date: Sep. 13, 2012

(65) Prior Publication Data
US 2014/0113830 A1    Apr. 24, 2014

(30) Foreign Application Priority Data
Mar. 9, 2011    (JP) ................. 2011-052219

(51) Int. Cl.
C12N 15/10    (2006.01)
G01N 33/543    (2006.01)
C12Q 1/37    (2006.01)
C07K 14/47    (2006.01)
C12P 21/02    (2006.01)
C12P 17/16    (2006.01)

(52) U.S. Cl.
CPC ....... *G01N 33/54393* (2013.01); *C07K 14/47* (2013.01); *C12N 15/1062* (2013.01); *C12P 21/02* (2013.01); *C12Q 1/37* (2013.01); *C12P 17/16* (2013.01); *G01N 2500/00* (2013.01)

(58) Field of Classification Search
None
See application file for complete search history.

(56) References Cited

U.S. PATENT DOCUMENTS

2009/0215172 A1* 8/2009 Schmidt .................. C07K 5/12
435/372.2
2010/0168380 A1 7/2010 Suga et al.

FOREIGN PATENT DOCUMENTS

WO    2007/103739 A2    9/2007
WO    2008/011783 A1    1/2008

OTHER PUBLICATIONS

McIntosh, et al., "Marine molecular machines: heterocyclization in cyanobactin biosynthesis", Jul. 5, 2010, pp. 1413-1421, vol. 11, No. 10, Publisher: ChemBioChem.

Mohamed S. Donia, et al., "Natural combinatorial peptide libraries in cyanobacterial symbionts of marine ascidians", Natural Chemical Biology, vol. 2; No. 12, Dec. 2006, pp. 729-735.
Peter Timmerman, et al. "Rapid and Quantitative Cyclization of Multiple Peptide Loops onto Synthetic Scaffolds for Structural Mimicry of Protein Surfaces", ChemBioChem, 2005, pp. 821-824.
Shaun W. Lee, et al. "Discovery of a widely distributed toxin biosynthetic gene cluster", PNAS, vol. 105; No. 15, Apr. 15, 2008, pp. 5879-5884.
Richard W. Roberts, et al., "RNA-peptide fusions for the in vitro selection of peptides and proteins", PNAS USA, vol. 94, Nov. 1997, pp. 12297-12302.
Yumi Ito, et al., "Substrate preference studies of a post-translational modification enzyme, PatD, toward the construction of azoline-containing chemical libraries", The Chemical Society of Japan, p. 724 [4 B4-36], English Abstract included.
Yumi Ito, et al., "A comprehensive study on the substrate tolerance of a promiscuous heterocyclase PatD", Annual Meeting of the Molecular Biology Society of Japan Program Yoshishu, Dec. 13, 2011, IP-0635 (1T11a-2).
International Search Report for PCT/JP2012/056181 (PCT/ISA/210); dated Jun. 12, 2012.
English Translation of International Search Report for PCT/JP2012/056181 (PCT/ISA210); dated Jun. 12, 2012.
Higuchi, et al., "Programmed Synthesis of Natural Product-like Non-standard Peptides Using the Translation System and Its Application", Mar. 2010, pp. 217-227, vol. 68, No. 3, Publisher: Journal of Synthetic Organic Chemistry, Published in: Japan.
Iida, et al., "Search for Special Peptide Drugs through RaPID System", Molecular tool to understand life phenomena From imaging to biological function analysis (Chemistry Frontier), ISBN: 978-4-7598-0752-3, Sep. 2010, p. 71-78, No. Chapter 9, Publisher: Chemical coterie, Hamada district (ed.) / Shiro Futaki (ed), Published in: Japan.
McIntosh, et al., "Marine molecular machines: heterocyclization in cyanobactin biosynthesis", Jul. 5, 2010, pp. 1413-1421, and support. Info. pp. 1-16, vol. 11, No. 10, Publisher Chembiochem.

(Continued)

*Primary Examiner* — Christopher M Gross
(74) *Attorney, Agent, or Firm* — Suzannah K. Sundby, Esq.; Canady + Lortz LLP

(57) ABSTRACT

An object of the present invention is to provide a method of efficiently constructing a library abundant in diversity and also usable for screening of a compound that binds to a target substance having protease activity.
The present invention provides a method of constructing an azoline compound library containing two or more azoline compounds having an azoline backbone introduced into at least one of Cys, Ser, Thr, and 2,3-diamino acid, and analogs thereof of Xaa$_0$ of a peptide represented by the following formula (I):

A-(Xaa$_0$)$_n$-B    (I)

[wherein, m numbers of Xaa$_0$s respectively represent arbitrary amino acids, at least one of which is an amino acid selected from the group consisting of Cys, Ser, Thr, and 2,3-diamino acid, and analogs thereof, m represents an inter selected from 2 to 40, and A and B each independently represent a peptide composed of from 0 to 100 amino acids].

16 Claims, 23 Drawing Sheets
Specification includes a Sequence Listing.

(56) References Cited

OTHER PUBLICATIONS

Goto, et al., "Goto XP002732732", "One-pot synthesis of azoline-containing peptides in a cell-free translation system integrated with a posttranslational cyclodehydratase", Jun. 19, 2014, pp. 766-774, vol. 21, No. 6, Publisher: Chemistry & Biology.

Mitchell, et al., "Structural and Functional Dissection of the Heterocyclic Peptide Cytotoxin Streptolysin S", May 8, 2009, pp. 13004-13012, vol. 284, Publisher: J Biol Chem.

Oman, et al., "Follow the leader: the use of leader peptides to guide natural product biosynthesis", Jan. 2010, pp. 9-18, vol. 6, Publisher: Nature Chemical Biology.

\* cited by examiner

Substrate tolerance of PatD - Effect of hydrophilic residue -

Fig. 5

| # | ID | Cassette sequence (1-14) |
|---|---|---|
| 1 | C1wt | V T A C I T F C |
| 2 | m005 | V S A S I S F S |
| 3 | m003 | V T A T I T F T |
| 4 | m004 | V C A C I C F C |
| 5 | m012 | V T A C N T F C |
| 6 | m026 | V T A C Q T F C |
| 7 | m013 | V T A C K T F C |
| 8 | m027 | V T A C H T F C |
| 9 | m028 | V T A C R T F C |
| 10 | m011 | V T A C D T F C |
| 11 | m025 | V T A C E T F C |
| 12 | m023 | N T A C I T F C |
| 13 | m024 | K T A C I T F C |
| 14 | m034 | R T A C I T F C |
| 15 | m022 | D T A C I T F C |
| 16 | m015 | V C A C N C F C |
| 17 | m016 | V C A C K C F C |
| 18 | m033 | V C A C R C F C |
| 19 | m040 | V S A S D S F S |
| 20 | m039 | V T A T D T F T |
| 21 | m014 | V C A C D C F C |
| 22 | m036 | R C D C D C R C |
| 23 | m042 | R C R C I C F C V C A C V C |
| 24 | m043 | V C A C I C R C R C A C V C |
| 25 | m044 | V C A C I C F C V C R C R C |
| 26 | m030 | V F A L I M F C |
| 27 | m031 | V F A L I M C C |
| 28 | m032 | V F A L I C C C |
| 29 | m035 | V F A L C C C C |
| 30 | m057 | S S S S S S |
| 31 | m056 | T T T T T T |
| 32 | m009 | C F T I C A T V |
| 33 | m021 | C F C I C A C V |
| 34 | m006 | V T A D I T F C |
| 35 | m007 | V T A N I T F C |
| 36 | m008 | V T A K I T F C |
| 37 | m058 | V F A T I T F T |
| 38 | m059 | C F A T I T F T |
| 39 | m045 | V T A T I C F C |
| 40 | m046 | V C A T I T F C |
| 41 | m047 | V C A C I T F T |
| 42 | m048 | V C A T I C F T |
| 43 | m017 | V C A T I T F T |
| 44 | m018 | V T A C I T F T |
| 45 | m019 | V T A T I C F T |
| 46 | m020 | V T A T I T F C |
| 47 | m029 | V T A C P T F C |

Formation of peptide from which leader sequence has been cleaved can be confirmed Synthesis of non-natural azoline by introducing and modifying non-natural amino acid
(List of non-natural amino acids tried)

Evaluation of binding ability of azoline-containing compound selected

Modification of synthetic peptide using substrate different from natural substrate - 2

Fig. 18

| Sequence | 5 10 15 20 25 30 35 | Number of loss of water molecule | | | | | Derived from |
|---|---|---|---|---|---|---|---|
| | | 4 | 3 | 2 | 1 | 0 | |
| 1 m190 | M------------ILASLSTFQQMWISKQEYDEAGDA- | ■ | | | | | actin |
| 2 m209 | M------------KEQNSFNLLQEVTESELDLILGA- | ■ | | | | | lacticin 481 |
| 3 m139 | MELQLRPSGLEKKQAPISELNIAQTQGGDSQVLALNA- | ■ | | | | | Shuffled |

Fig. 19

| Sequence | 5 10 15 20 25 30 35 | 4 | 3 | 2 | 1 | 0 |
|---|---|---|---|---|---|---|
| C1wt | MNKKNILPQQGQPVIRLTAGQLSSQLAELSEEALGDA- | ■ | ▓ |  |  |  |
| m127 | MNKKNILPQQGQPVIRLTAGQLSSQL------------ |  |  |  | ▓ | ■ |
| m111 | M--------GQPVIRLTAGQLSSQLAELSE------- |  |  |  | ■ |  |
| m076 | M--------GQPVIRLTAGQLSSQLAELSEEALGDA- | ■ | ▓ |  |  |  |
| m114 | M-------------IRLTAGQL--------------- |  |  |  | ■ |  |
| m112 | M-------------IRLTAGQLSSQL----------- |  |  |  | ▓ | ■ |
| m113 | M------------------AGQLSSQL---------- |  |  |  |  | ■ |
| m075 | M----------------GQLSSQLAELSEEALGDA- | ■ | ▓ | ▓ |  |  |
| m083 | M-------------------------LAELSE------ |  |  |  | ■ |  |
| m082 | M-------------------------LAELSEEAL---- |  | ■ |  |  |  |
| m074 | M-------------------------LAELSEEALGDA- | ■ | ▓ |  |  |  |
| m080 | M-----------------------------LSEEALGDA- |  | ■ | ▓ | ▓ |  |
| m081 | M--------------------------------EALGDA- |  |  |  | ▓ | ■ |
| m088 | M------------------------------------- |  |  |  |  | ■ |

Fig. 20

| Sequence | 5 10 15 20 25 30 35 | Number of loss of water molecule 4 3 2 1 0 |
|---|---|---|
| C1wt | MNKKNILPQQGQPVIRLTAGQLSSQLAELSEEALGDA- | |
| 26A | MNKKNILPQQGQPVIRLTAGQLSSQAAELSEEALGDA- | |
| 26N | MNKKNILPQQGQPVIRLTAGQLSSQNAELSEEALGDA- | |
| 27G | MNKKNILPQQGQPVIRLTAGQLSSQLGELSEEALGDA- | |
| 27N | MNKKNILPQQGQPVIRLTAGQLSSQLNELSEEALGDA- | |
| 28A | MNKKNILPQQGQPVIRLTAGQLSSQLAALSEEALGDA- | |
| 28Q | MNKKNILPQQGQPVIRLTAGQLSSQLAQLSEEALGDA- | |
| 29A | MNKKNILPQQGQPVIRLTAGQLSSQLAEASEEALGDA- | |
| 29N | MNKKNILPQQGQPVIRLTAGQLSSQLAENSEEALGDA- | |
| 30A | MNKKNILPQQGQPVIRLTAGQLSSQLAELAEEALGDA- | |
| 31A | MNKKNILPQQGQPVIRLTAGQLSSQLAELSAEALGDA- | |
| 31Q | MNKKNILPQQGQPVIRLTAGQLSSQLAELSQEALGDA- | |
| 32A | MNKKNILPQQGQPVIRLTAGQLSSQLAELSEAALGDA- | |
| 32Q | MNKKNILPQQGQPVIRLTAGQLSSQLAELSEQALGDA- | |
| 33G | MNKKNILPQQGQPVIRLTAGQLSSQLAELSEEGLGDA- | |
| 33N | MNKKNILPQQGQPVIRLTAGQLSSQLAELSEENLGDA- | |
| 34A | MNKKNILPQQGQPVIRLTAGQLSSQLAELSEEAAGDA- | |
| 34N | MNKKNILPQQGQPVIRLTAGQLSSQLAELSEEANGDA- | |
| 35A | MNKKNILPQQGQPVIRLTAGQLSSQLAELSEEALADA- | |
| 36A | MNKKNILPQQGQPVIRLTAGQLSSQLAELSEEALGAA- | |
| 36N | MNKKNILPQQGQPVIRLTAGQLSSQLAELSEEALGNA- | |
| 37G | MNKKNILPQQGQPVIRLTAGQLSSQLAELSEEALGDG- | |
| 37N | MNKKNILPQQGQPVIRLTAGQLSSQLAELSEEALGDN- | |
| p1 | MNKKNILPQQGQPVIRLTAGQLSSQLAENSEEGLGDA- | |
| p2 | MNKKNILPQQGQPVIRLTAGQLSSQLAENSEENLGDA- | |
| p3 | MNKKNILPQQGQPVIRLTAGQLSSQLAENSEEANGDA- | |
| p4 | MNKKNILPQQGQPVIRLTAGQLSSQLAELSEEGNGDA- | |
| p5 | MNKKNILPQQGQPVIRLTAGQLSSQLAELSEENNGDA- | |
| p6 | MNKKNILPQQGQPVIRLTAGQLSSQLAENSEEGNGDA- | |
| p7 | MNKKNILPQQGQPVIRLTAGQLSSQLAENSEENNGDA- | |
| p8 | MNKKNILPQQGQPVIRLTAGQLSSQLAQLSQEALGDA- | |
| p9 | MNKKNILPQQGQPVIRLTAGQLSSQLAQLSEQALGDA- | |
| p10 | MNKKNILPQQGQPVIRLTAGQLSSQLAQLSEEALGNA- | |
| p11 | MNKKNILPQQGQPVIRLTAGQLSSQLAELSQQALGDA- | |
| p12 | MNKKNILPQQGQPVIRLTAGQLSSQLAELSQEALGNA- | |
| p13 | MNKKNILPQQGQPVIRLTAGQLSSQLAELSEQALGNA- | |
| p14 | MNKKNILPQQGQPVIRLTAGQLSSQLAQLSQQALGDA- | |
| p15 | MNKKNILPQQGQPVIRLTAGQLSSQLAQLSQEALGNA- | |
| p16 | MNKKNILPQQGQPVIRLTAGQLSSQLAQLSEQALGNA- | |
| p17 | MNKKNILPQQGQPVIRLTAGQLSSQLAELSQQALGNA- | |
| m126 | MNKKNILPQQGQPVIRLTAGQLSSQLAQLSQQALGNA- | |
| p21 | MNKKNILPQQGQPVIRLTAGQLSSQLAQNSQQANGDA- | |
| m171 | MNKKNILPQQGQPVIRLTAGQGSSQGAEGSEEGLGDA- | |
| m172 | MNKKNILPQQGQPVIRLTAGQNSSQNAENSEEGLGDA- | |
| m173 | MNKKNILPQQGQPVIRLTAGQNSSQNAENSEEALGDA- | |
| m174 | MNKKNILPQQGQPVIRLTAGQNSSQNAENAEEALGDA- | |
| m175 | MNKKNILPQQGQPVIRLTAGQNSSQNAEEENLGDA- | |
| m225 | MNKKNILPQQGQPVNRLTNGQNSSQNAELSEEALGDA- | |
| m176 | MNKKNILPQQGQPVNRLTGGQNSSQNAELSEEALGDA- | |
| m125 | MNKKNILPQQGQPVGRLTGGQGSSQGAELSEEALGDA- | |
| m170 | MNKKNILPQQGQPVIRLTAGQLSSQLAELSEEPLGDA- | |
| m169 | MNKKNILPQQGQPVIRLTAGQLSSQLPELSEEPLGDA- | |
| m168 | MNKKNILPQQGQPVIRLTAGPLSSQLPELSEEPLGDA- | |
| m187 | MNKKNILPQQGQPVIRPTAGQPSSQLPELSEEPLGDA- | |
| 35P | MNKKNILPQQGQPVIRLTAGQLSSQLAELSEEALPDA- | |
| 30P | MNKKNILPQQGQPVIRLTAGQLSSQLAELPEEALGDA- | |
| p18 | MNKKNILPQQGQPVIRLTAGQLSSQLAELPEEALPDA- | |
| p19 | MNKKNILPQQGQPVIRLTAGQLSPQLAELPEEALPDA- | |
| p20 | MNKKNILPQQGQPVIRLPAGQLSPQLAELPEEALPDA- | |
| m088 | M------------------------------------ | |

AZOLINE COMPOUND AND AZOLE COMPOUND LIBRARY AND METHOD FOR PRODUCING SAME

REFERENCE TO A SEQUENCE LISTING SUBMITTED VIA EFS-WEB

The content of the ASCII text file of the Sequence Listing named "20131205_034574_003US1_seq" which is 134 KB in size was created on 5 Dec. 2013 and electronically submitted via EFS-Web on 5 Dec. 2013 is incorporated herein by reference in its entirety.

TECHNICAL FIELD

The present invention relates to an azoline compound library, an azole compound library, and the like.

BACKGROUND ART

In recent years, a variety of peptides has attracted attentions as a drug candidate or research tool. There have been various attempts to develop a peptide library and screen peptides having affinity with a target substance.

As a method of artificially constructing a peptide library, a method using chemical synthesis, a method using a biosynthetic enzyme of a secondary metabolite, and a translation synthesis system, and the like have been employed conventionally.

It is however difficult, in the method using chemical synthesis, to increase the diversity of a library. In addition, it takes time for screening or analyzing the relationship between the structure of a compound and activity.

The method of using a biosynthetic enzyme of a secondary metabolite, on the other hand, enables rapid and easy construction or chemical conversion of a precise backbone that is difficult to be achieved by the chemical synthesis method. Since enzymes have substrate specificity, however, kinds of compounds that can be synthesized are limited. This method is therefore not suited for use in the construction of a compound library with highly diverse kinds of molecules.

When a translation system is used, a peptide library rich in diversity can be constructed in a short time by constructing an mRNA library and translating it in one pot. By using this system in combination with an mRNA display method or the like, both a peptide selected by screening and information on a nucleic acid encoding such peptide can be obtained simultaneously so that the genotype and the phenotype of the selected peptide can be related to each other easily. Despite the fact that synthesis of a peptide library using such a translation system has many advantages, it can only produce compounds consisting of peptidic backbone.

In screening using a library, identification of a compound inhibiting a target substance having protease activity is often required. The library of peptidic compounds is however cleaved by protease, and thus compounds inhibiting the activity of a target substance cannot be screened efficiently.

Each peptide of the peptide library may be modified in vitro with a post-translational modification enzyme, but an enzyme having a desired activity does not always have activity in vitro. In addition, the expressed peptide library should be purified prior to the reaction with an enzyme, and investigation of substrate specificity of the enzyme is also required. It is therefore not easy to obtain a library comprised of peptides having a desired structure.

A library in which the presence or absence, or degree of modification of each member cannot be identified is inferior in usefulness because it eventually requires correlation analysis between structure and activity, as in the chemical synthesis system.

Patellamide produced by *Prochloron didemni*, that is, endozoic algae of sea squirt is a low molecular cyclic peptide which is presumed to have various physiological activities and it is biosynthesized via a unique pathway with products of a pat gene cluster consisting of patA to patG. The pat gene cluster and biosynthesis pathway of patellamide are schematically shown in FIG. 15.

In this biosynthesis, PatE peptide which is a patE gene product serves as a precursor. Since the patE gene has a hypervariable region (cassette domain), the product of it constructs a natural combinatorial library.

The PatE peptide has, on both sides of the cassette domain, a recognition sequence by a post-translational modification enzyme. PatA, PatD, and PatG serve as the post-translational modification enzyme. Pat D introduces an azoline backbone into Cys, Ser, and Thr in the cassette of PatE and converts Cys to a thiazoline backbone and Ser and Thr into an oxazoline backbone.

PatE cleaves the recognition sequence at the N-terminus side of the cassette domain of the PatE.

PatG is composed of two domains. An oxidase domain on the N-terminus side converts an azoline backbone introduced by PatD into an azole backbone, that is, converts a thiazoline backbone into an azole backbone. A peptidase domain on the C-terminus side macrocyclizes PatE, while cleaving the recognition sequence on the C-terminus side of the cassette domain of PatE.

With regard to the cassette domain of the above-mentioned natural PatE, sequences shown in the following table are described in M. S. Donia et al. (Non-patent Document 1).

[Table 1] is provided as FIG. 22.

TABLE 2

| COMPOUND | CODING SEQUENCE |
|---|---|
| patellamide family: | |
| patellamide C (E1I, E2I) | V T A C I T F C |
| patellamide A (E1II) | I T V C I S V C |
| patellamide B (E4I, E5I) | L T A C I T F C |
| new compound 1 (E6I) | V A A C I T F C |
| new compound 2 (E7I) | L T T C I T F C |
| new compound 3 (E8I) | L T A C V T F C |
| new compound 4 (E9II) | I T V C I T V C |
| new compound 5 (E10I) | L A A C I T F C |
| new compound 6 (E11I) | L T A C I T L C |
| new compound 7 (E12II) | I T V C I S A C |
| new compound 8 (E13II) | S T V C F T V C |
| new compound 9 (E15I) | V T A C I A F C |
| new compound 10 (E16I) | V T A C I T S C |
| new compound 11 (E17I) | V T A C I T L C |
| new compound 12 (E18I) | V T T C I T F C |
| new compound 13 (E20I) | V T A C T T F C |
| ulithiacyclamide family: | |
| ulithiacyclamide (E2II) | C T L C C T L C |
| new compound 14 (E14II) | C T L C C T L R |
| new compound 15 (E19II) | C I L C C T L C |
| new compound 16 (E21II) | C T L C C A L C |
| new compound 17 (E22II) | C T L C C T V C |
| new compound 18 (E23II) | C T L C C T F C |
| new compound 19 (E24II) | C T V C C A V C |
| new compound 20 (E25II) | C T L C Y T L C |
| lissoclinamide family: | |
| lissoclinamide 2/3 (E3I) | A C F P T I C |
| lissoclinamide 4/5 (E3II) | F C F P T V C |
| new compound 21 (E26II) | L C F P T V C |
| new compound 22 (E27II) | F C V P T V C |

TABLE 2-continued

| COMPOUND | CODING SEQUENCE |
|---|---|
| new compound 23 (E28II) | F C F P A V C |
| new compound 24 (E29II) | F C L P T V C | patellamide A

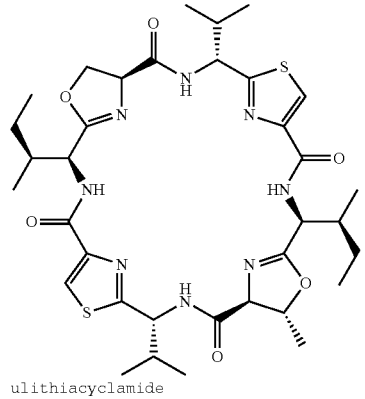

ulithiacyclamide

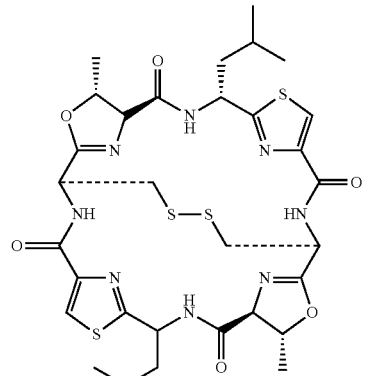

lissoclinamide 2/3

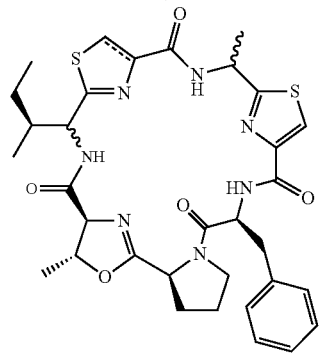

The corresponding sequence numbers of Table 2 from top to bottom are: SEQ ID NOS: 60, 348-376, respectively.

These tables show that sequences of natural cassette domains have following similarities: (i) they have 7 or 8 residues, (ii) they tend to have Ser/Thr/Cys to be modified at 2, 4, 6, or 8 positions from the N-terminus of the cassette domain, (iii) the residues (Ser, Thr, and Cys) to be modified are not adjacent to each other in most cases, and (iv) many of the residues other than Ser, Thr, and Cys are hydrophobic residues such as Val, Ala, Ile, Phe, and Leu.

These similarities were presumed to be necessary for becoming a substrate of PatD or PatG, a post-translational modification enzyme. It is however not known which residue of Ser, Thr, and Cys has been modified or not modified and substrate specificity of PatD and PatG has not been elucidated yet.

PRIOR ART DOCUMENT

Non-Patent Document

Non-Patent Document 1: Donia, M. S. et al., Nat. Chem. Biol., 2006, 2:729-735.

SUMMARY OF THE INVENTION

Problem to be Solved by the Invention

An object of the present invention is to provide a method of efficiently constructing a library having sufficient diversity and usable for screening of a compound that binds to a target substance even having protease activity.

Means for Solving the Problem

The present inventors considered that a library usable for screening of compounds that bind to a target substance having protease activity can be obtained and the above-mentioned problem can be solved if a PatE library more abundant in diversity than natural one can be obtained efficiently by some method and if modification with a post-translational modification enzyme can be made by using such library as a substrate.

As a result of further investigation described herein, we found that some of azoline backbone-introducing enzymes have azoline backbone forming activity even in vitro; and the sequence of the cassette domain which is a substrate of such an azoline backbone-introducing enzyme is not limited to that described in M. S. Donia et al. but a cassette domain having from 2 to 40 amino acid residues may also be a substrate of the enzyme and Cys, Ser, Thr, and 2,3-diamino acid and analogs thereof in the cassette domain can be converted into an azoline backbone.

It has further been confirmed that steps of expressing a PatE library in a cell-free translation system by using a precursor peptide comprising, in the order of mention from the N-terminus, a leader sequence of PatE, a recognition sequence 1 by an azoline backbone-introducing enzyme, a cassette domain, and a recognition sequence 2 by the azoline backbone-introducing enzyme, modifying it with the azoline backbone-introducing enzyme, and cutting off an unnecessary region can be conducted efficiently in one pot and as a result, an azoline compound library sufficiently abundant in diversity and usable for screening using even a target substance having protease activity can be obtained.

We also found that the above-mentioned precursor peptide may be a substrate of an azoline backbone-introducing enzyme when, in the above-mentioned precursor peptide, only a portion of a conventionally known leader sequence is used as the leader sequence of PatE or the leader sequence is completely removed; when sequences different from those conventionally known as the recognition sequence 1 or 2 is used; when the recognition sequences 1 and 2 are removed; or the like. Moreover, it has been confirmed that even if as the leader sequence portion, a peptide separated from a precursor peptide comprising a cassette domain is used, as long as the peptide is present in a reaction system, the precursor peptide comprising a cassette domain may be a substrate of an azoline backbone-introducing enzyme, leading to the completion of the present invention.

The present invention relates to:

[1] a method of constructing an azoline compound library containing two or more azoline compounds having an azoline backbone introduced into at least one of Cys, Ser, Thr, and 2,3-diamino acid, and analogs thereof of $Xaa_0$ of a peptide represented by the following formula (I):

$$A\text{-}(Xaa_0)_m\text{-}B \quad (I)$$

(wherein, m numbers of $Xaa_0$s respectively represent arbitrary amino acids, at least one of which is an amino acid selected from the group consisting of Cys, Ser, Thr, and 2,3-diamino acid, and analogs thereof, m represents an integer selected from 2 to 40, and A and B each independently represent a peptide composed of from 0 to 100 amino acids), including:

a step of constructing an mRNA library encoding a precursor peptide comprising, in order of mention from the N-terminus, a recognition sequence 1 by an azoline backbone-introducing enzyme, $\text{-}(Xaa_0)_m\text{-}$, and a recognition sequence 2 by the azoline backbone-introducing enzyme (the recognition sequences 1 and 2 being recognition sequences by the azoline backbone-introducing enzyme each composed of from 0 to 10 amino acids);

a step of expressing the precursor peptide in a cell-free translation system by using the mRNA library and thereby constructing a peptide library; and a step of reacting the azoline backbone-introducing enzyme and the peptide library in the presence of a peptide comprising a leader sequence of a substrate of the azoline backbone-introducing enzyme and thereby introducing an azoline backbone into at least one of Cys, Ser, Thr, and 2,3-diamino acid, and analogs thereof of $Xaa_0$ (the leader sequence being a leader sequence of a substrate of the azoline backbone-introducing enzyme composed of from 0 to 50 amino acid);

[2] a method of constructing an azoline compound library containing two or more complexes between an azoline compound having an azoline backbone introduced into at least one of Cys, Ser, Thr, and 2,3-diamino acid, and analogs thereof of $Xaa_0$ of a peptide represented by the following formula (I):

$$A\text{-}(Xaa_0)_m\text{-}B \quad (I)$$

(wherein, m numbers of $Xaa_0$s respectively represent arbitrary amino acids, at least one of which represents an amino acid selected from the group consisting of Cys, Ser, Thr, and 2,3-diamino acid, and analogs thereof, m represents an integer selected from 2 to 40, and A and B each independently represent a peptide composed of from 0 to 100 amino acids) and an mRNA encoding the peptide represented by the formula (I), including:

a step of constructing an mRNA library encoding a precursor peptide comprising, in order of mention from the N-terminus, a recognition sequence 1 by an azoline backbone-introducing enzyme, $\text{-}(Xaa_0)_m\text{-}$, and a recognition sequence 2 by the azoline backbone-introducing enzyme (the recognition sequences 1 and 2 being recognition sequences by the azoline backbone-introducing enzyme each composed of from 0 to 10 amino acids);

a step of binding a puromycin to the 3' end of each mRNA of the mRNA library to construct a puromycin bound mRNA library;

expressing the precursor peptide in a cell-free translation system by using the puromycin-bound mRNA library and constructing a peptide-mRNA complex library; and a step of reacting the azoline backbone-introducing enzyme and the peptide-mRNA complex library in the presence of a peptide comprising a leader sequence of a substrate of the azoline backbone-introducing enzyme and introducing an azoline backbone into at least one of Cys, Ser, Thr, and 2,3-diamino acid, and analogs thereof of $Xaa_0$ (the leader sequence being a leader sequence of a substrate of the azoline backbone-introducing enzyme composed of from 0 to 50 amino acid);

[3] the method of constructing an azoline compound library as described above in [1] or [2], wherein:

in the formula (I), $\text{-}(Xaa_0)_m\text{-}$ means $\text{-}(Xaa_1\text{-}Xaa_2)_n\text{-}$ (wherein, n numbers of $Xaa_1$ each independently represent an arbitrary amino acid, n numbers of $Xaa_2$ each independently represent an amino acid selected from the group consisting of Cys, Ser, Thr, and 2,3-diamino acid, and analogs thereof, and n represents an integer selected from 1 to 20); and an azoline backbone has been introduced into at least one of Cys, Ser, Thr, and 2,3-diamino acid, and analogs thereof of $Xaa_1$ and $Xaa_2$ of the azoline compound;

[4] the method as described above in any one of [1] to [3], wherein at least one of the peptides represented by the formula (I) is a peptide having at least one of the following characteristics (i) to (iv):

(i) m represents from 2 to 40 (with the proviso that 7 and 8 are excluded);

(ii) n represents from 1 to 20 (with the proviso that 3 and 4 are excluded);

(iii) at least one of $Xaa_1$s is an amino acid selected from Cys, Ser, Thr, and 2,3-diamino acid, and analogs thereof; and (iv) at least one of $Xaa_1$s is a hydrophilic amino acid;

[5] the method as described above in any one of [1] to [3], wherein at least one of the peptides represented by the formula $\text{-}(Xaa_0)_m\text{-}$ is a peptide represented by any of SEQ ID NOS: 10 to 57;

[6] the method as described above in any one of [1] to [5], wherein at least one of the azoline compounds has 5 or more azoline backbones;

[7] the method as described above in any one of [1] to [6], wherein each of the mRNAs of the mRNA library is constituted so that each peptide comprising the leader sequence is expressed as a fusion peptide with the precursor peptide comprising a recognition sequence 1, $\text{-}(Xaa_0)_m\text{-}$, and a recognition sequence 2;

[8] the method as described above in [7], further comprising, after introduction of the azoline backbone, a step of cleaving the leader sequence from the precursor peptide;

[9] the method as described above in any one of [1] to [6], wherein in the step of introducing an azoline backbone, the peptide comprising a leader sequence is separated from the precursor peptide comprising a recognition sequence 1, $\text{-}(Xaa_0)_m\text{-}$, and a recognition sequence 2;

[10] the method as described above in any one of [1] to [9], further comprising a step of macrocyclizing the azoline compound;

[11] the method of constructing an azole compound library, comprising, after the step of introducing an azoline backbone in the method of constructing an azoline compound library according to any one of claims 1 to 10, a step of reacting the library having an azoline backbone introduced therein with an azole backbone-introducing enzyme in the presence or absence of a peptide comprising a leader sequence of a substrate of the azole backbone-introducing enzyme and converting at least one of the azoline backbones into an azole backbone (the leader sequence meaning a leader sequence of a substrate of the azoline backbone-introducing enzyme composed of from 0 to 50 amino acids);

[12] the method as described above in [11], wherein the azole backbone-introducing enzyme is a mutant of PatG that has lost the peptidase domain thereof or that has lost the peptidase activity by point mutation;

[13] an azoline compound library containing two or more azoline compounds having an azoline backbone introduced into at least one of Cys, Ser, Thr, and 2,3-diamino acid, and analogs thereof of $Xaa_0$ of a peptide represented by the following formula (I):

$$A\text{-}(Xaa_0)_m\text{-}B \qquad (I)$$

(wherein, m numbers of $Xaa_0$s respectively represent arbitrary amino acids, at least one of which is an amino acid selected from the group consisting of Cys, Ser, Thr, and 2,3-diamino acid, and analogs thereof, m represents an integer selected from 2 to 40, and A and B each independently represent a peptide composed of from 0 to 100 amino acids), wherein:

in at least one of the peptides represented by the formula (I), m does not represent 7 or 8;

[14] the azoline compound library as described above in [13], wherein in the formula (I), -$(Xaa_0)_m$- means -$(Xaa_1$-$Xaa_2)_n$- [wherein, n numbers of $Xaa_1$ each independently represent an arbitrary amino acid, n numbers of $Xaa_2$ each independently represent an amino acid selected from the group consisting of Cys, Ser, Thr, and 2,3-diamino acid, and analogs thereof, and n represents an integer selected from 1 to 10]; and at least one of the peptides represented by the formula (I) is a peptide having at least one of the following characteristics (i) to (iv):

(i) m represents from 2 to 40 (with the proviso that 7 and 8 are excluded);

(ii) n represents from 1 to 20 (with the proviso that 3 and 4 are excluded);

(iii) at least one of $Xaa_1$s is an amino acid selected from Cys, Ser, Thr, and 2,3-diamino acid, and analogs thereof; and (iv) at least one of $Xaa_1$s is a hydrophilic amino acid;

[15] the azoline compound library as described above in [13] or [14], wherein each of the azoline compounds forms a complex with an mRNA encoding the peptide portion of the azoline compound;

[16] the azoline compound library as described above in any one of [13] to [15], wherein the entirety or a portion of the recognition sequence by the azoline backbone-introducing enzyme has been bound to the N-terminus and C-terminus of the peptide represented by the formula (I);

[17] an azole compound library containing two or more azole compounds having an azole backbone introduced into at least one of Cys, Ser, Thr, and 2,3-diamino acid, and analogs thereof of $Xaa_0$ of a peptide represented by the following formula (I):

$$A\text{-}(Xaa_0)_m\text{-}B \qquad (I)$$

[wherein, m numbers of $Xaa_0$s represent arbitrary amino acids, at least one of which is an amino acid selected from the group consisting of Cys, Ser, Thr, and 2,3-diamino acid, and analogs thereof, m represents an integer selected from 2 to 40, and A and B each independently represents a peptide composed of from 0 to 100 amino acids], wherein:

in at least one of the peptides represented by the formula (I), m does not represent 7 or 8;

[18] the azole compound library as described above in [17], wherein in the formula (I), -$(Xaa_0)_m$- means -$(Xaa_1$-$Xaa_2)_n$- [wherein, n numbers of $Xaa_1$ each independently represent an arbitrary amino acid, n numbers of $Xaa_2$ each independently represent an amino acid selected from the group consisting of Cys, Ser, Thr, and 2,3-diamino acid, and analogs thereof, and n represents an integer selected from 1 to 20); and at least one of the peptides represented by the formula (I) has at least one of the following characteristics (i) to (iv):

(i) m represents from 2 to 40 (with the proviso that 7 and 8 are excluded);

(ii) n represents from 1 to 20 (with the proviso that 3 and 4 are excluded);

(iii) at least one of $Xaa_1$s is an amino acid selected from Cys, Ser, Thr, and 2,3-diamino acid, and analogs thereof; and (iv) at least one of $Xaa_1$s is a hydrophilic amino acid;

[19] the azole compound library as described above in [17] or [18], wherein each of the azole compounds forms a complex with an mRNA encoding the peptide portion of the compound;

[20] the azole compound library as described above in any one of [17] to [19], wherein the entirety or a portion of the recognition sequence by the azoline backbone-introducing enzyme binds to the N-terminus and C-terminus of the peptide represented by the formula (I);

[21] a screening method for identifying an azoline compound that binds to a target substance, including:

a step of bringing the azoline compound library constructed by using any one of the methods described in from [1] to [10] or the azoline compound library as described above in any one of [13] to [16] into contact with a target substance, followed by incubation, and a step of selecting the azoline compound that has bound to the target substance;

[22] a screening method for identifying an azoline compound that binds to a target substance, including:

a step of bringing the azoline compound library constructed by using any one of the methods described in from [2] to [10] or the azoline compound library as described above in [15] or [16] into contact with a target substance, followed by incubation, a step of selecting an azoline compound that has bound to the target substance, and a step of analyzing the base sequence of the mRNA of the thus-selected azoline compound;

[23] a screening method for identifying an azole compound that binds to a target substance, including:

a step of bringing the azole compound library constructed by using the method described in [11] or [12] or the azole compound library as described above in any one of from [17] to [20] into contact with a target substance, followed by incubation, and a step of selecting an azole compound that has bound to the target substance;

[24] a screening method for identifying an azole compound that binds to a target substance, including:

a step of bringing the azole compound library constructed by using the method described in [11] or [12] or the azole compound library as described above in [19] or [20] into contact with a target substance, followed by incubation, a step of selecting an azole compound that has bound to the target substance, and a step of analyzing the base sequence of the mRNA of the thus-selected azole compound;

[25] a screening kit for identifying an azoline compound that binds to a target substance, including:

the azoline compound library constructed by using the method as described in any one of from [1] to [10] or the azoline compound library as described above in any one of from [13] to [16];

[26] the kit as described above in [25], wherein the library has been immobilized onto a solid phase support;

[27] a screening kit for identifying an azole compound that binds to a target substance, including:

the azole compound library constructed by using the method as described above in [11] or [12] or the azole compound library as described above in any one of from [17] to [20];

[28] the kit as described above in [27], wherein the library has been immobilized onto a solid phase support;

[29] a method of preparing an azoline compound having an azoline compound introduced into at least one of Cys, Ser, Thr, and 2,3-diamino acid, and analogs thereof of $Xaa_0$ of a peptide represented by the following formula (I):

[wherein, m numbers of $Xaa_0$s represent arbitrary amino acids, at least one of which is an amino acid selected from the group consisting of Cys, Ser, Thr, and 2,3-diamino acid, and analogs thereof, m represents an integer selected from 2 to 40, and A and B each independently represent a peptide composed of from 0 to 100 amino acids), including:

a step of preparing an mRNA encoding a precursor peptide comprising, in order of mention from the N-terminus, a recognition sequence 1 by an azoline backbone-introducing enzyme, $-(Xaa_0)_m-$, and a recognition sequence 2 by the azoline backbone-introducing enzyme (the recognition sequences 1 and 2 being recognition sequences by the azoline backbone-introducing enzyme each composed of from 0 to 10 amino acids);

a step of expressing the precursor peptide in a cell-free translation system by using the mRNA; and a step of reacting the azoline backbone-introducing enzyme and the precursor peptide in the presence of a peptide comprising a leader sequence of a substrate of the azoline backbone-introducing enzyme and thereby introducing an azoline backbone into at least one of Cys, Ser, Thr, and 2,3-diamino acid, and analogs thereof of $Xaa_0$ (with the proviso that the peptide comprising the leader sequence is separated from the precursor peptide comprising the recognition sequence 1, $-(Xaa_0)_m-$, and the recognition sequence 2);

[30] a method of preparing an azole compound including:

a step of reacting the azoline compound prepared by using the method as described above in [29] and an azole backbone-introducing enzyme in the presence or absence of a peptide comprising a leader sequence of a substrate of the azole backbone-introducing enzyme and thereby converting at least one of the azoline backbones into an azole backbone; and

[31] a kit for preparing an azoline compound or an azole compound, comprising an azoline backbone-introducing enzyme or azole backbone-introducing enzyme and a peptide comprising a leader sequence of a substrate of the azoline backbone-introducing enzyme.

Effect of the Invention

The method of the present invention makes it possible to rapidly and easily provide an azoline compound library and an azole compound library much more abundant in diversity than a natural PatE library.

By using such an azoline compound or azole compound library, an azoline compound or azole compound that binds to a target substance having protease activity can be screened.

In addition, when an mRNA display method is applied to the azoline compound or azole compound library of the present invention and a library of complexes between an azoline compound or azole compound and an mRNA encoding the peptide portion thereof is constructed, it is possible to determine a nucleic acid sequence encoding the azoline compound/azole compound identified by screening and thereby easily analyze the relationship between the structure and activity of the compound.

BRIEF DESCRIPTION OF THE DRAWINGS

FIG. 5 shows the results of the substrate acceptance of PatD based on the results of tests of introducing an azoline backbone by using PatD into cassette domains having various sequences. In each of these sequences, the number of heterocycles introduced after the reaction of PatD is shown with the color density in the box as an indicator. It shows that the darker the color is, the greater the number of products having heterocycles introduced therein is observed.

The box in light color shows byproducts. The corresponding sequence numbers of FIG. 5 from top to bottom are SEQ ID NOS: 60, 14, 12, 13, 21, 35, 22, 36, 37, 20, 34, 32, 33, 43, 31, 24, 25, 42, 49, 48, 23, 45, 51, 52, 53, 39, 40, 41, 44, 188, 187, 18, 30, 15, 16, 17, 189, 190, 54, 55, 56, 57, 26, 27, 28, 29, and 38, respectively.

Figure 6:
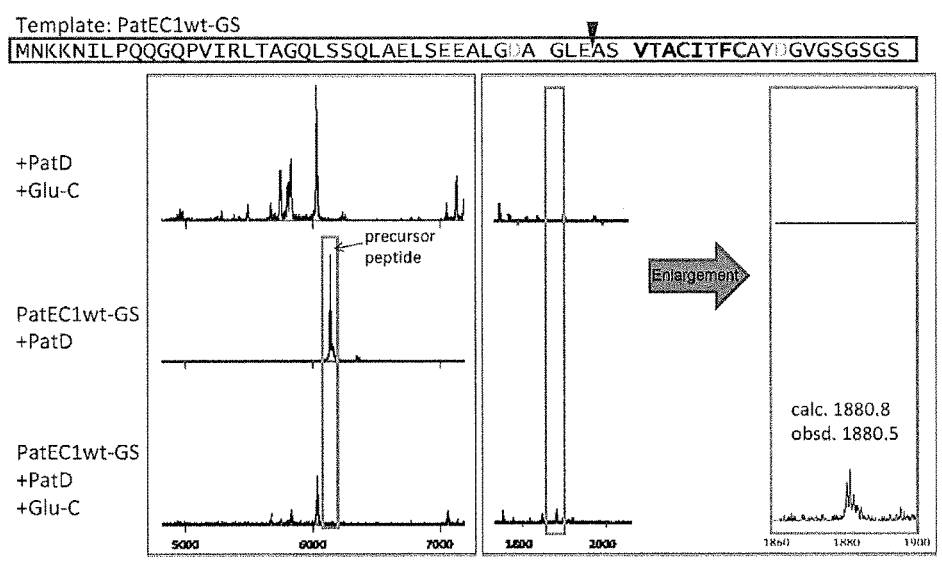

FIG. 6 shows the confirmation results, by mass spectrometry analysis, of cleavage of a leader sequence by Glu-C. When PatEC1wt-GS was treated with PatD and Glu-C (PatEC1wt-GS+PatD+Glu-C), a peak which was not found in the absence of a substrate peptide (+PatD+Glu-C) was observed (1880.5).

It corresponds to a C-terminal short peptide site containing four heterocycles. The corresponding sequence numbers of FIG. 6 are:
MNKKNILPQQGQPVIRLTAGQLSSQLAELS
EEALGDA=SEQ ID NO: 1,
GLEAS=SEQ ID NO: 3,
VTACITFC=SEQ ID NO: 60, and
AYDGVGSGSGS=SEQ ID NO: 7.

Figure 7:
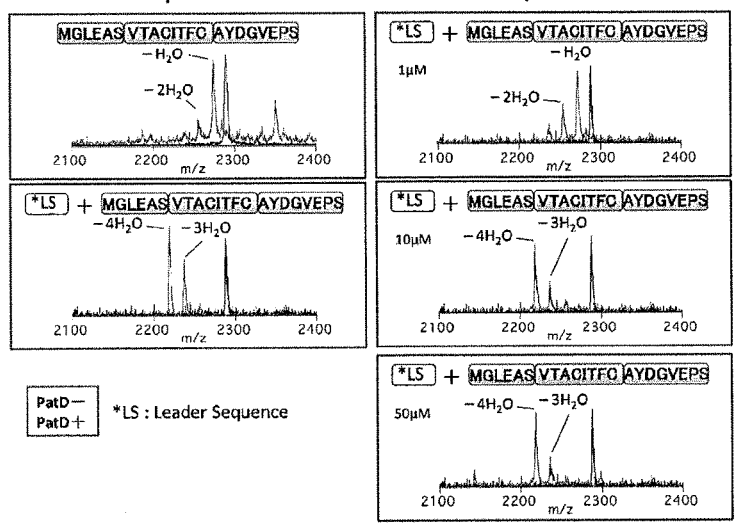

FIG. 7 shows the results of investigating the substrate acceptance of PatD while adding to the reaction system a leader sequence as a separate peptide or while not adding any leader sequence. The corresponding sequence numbers of FIG. 7 are:
GLEAS=SEQ ID NO: 3,
VTACITFC=SEQ ID NO: 60, and
AYDGVEPS=SEQ ID NO: 5.

Figure 8:
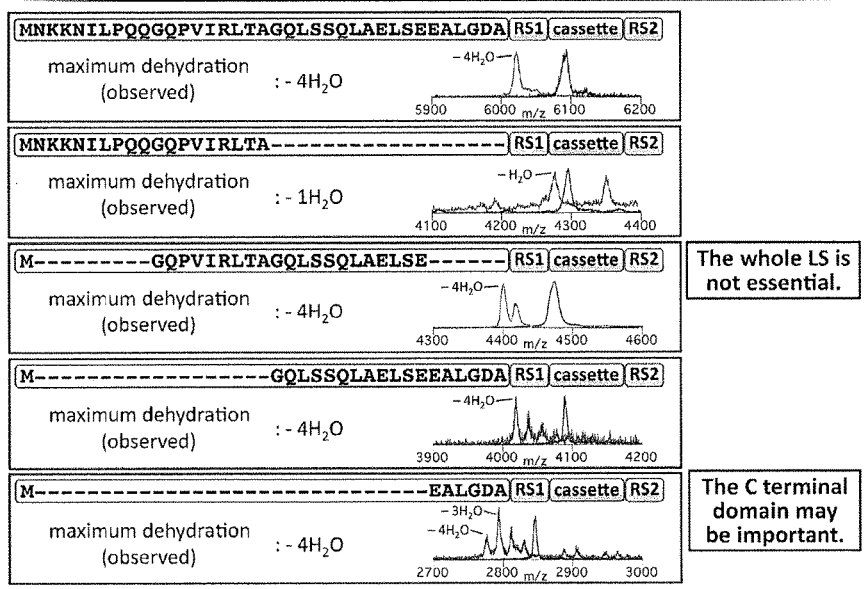

FIG. 8 shows an example of the results of investigating the substrate acceptance of PatD while deleting a portion of the leader sequence. The corresponding sequence number of FIG. 8 is SEQ ID NO: 1.

Figure 9:
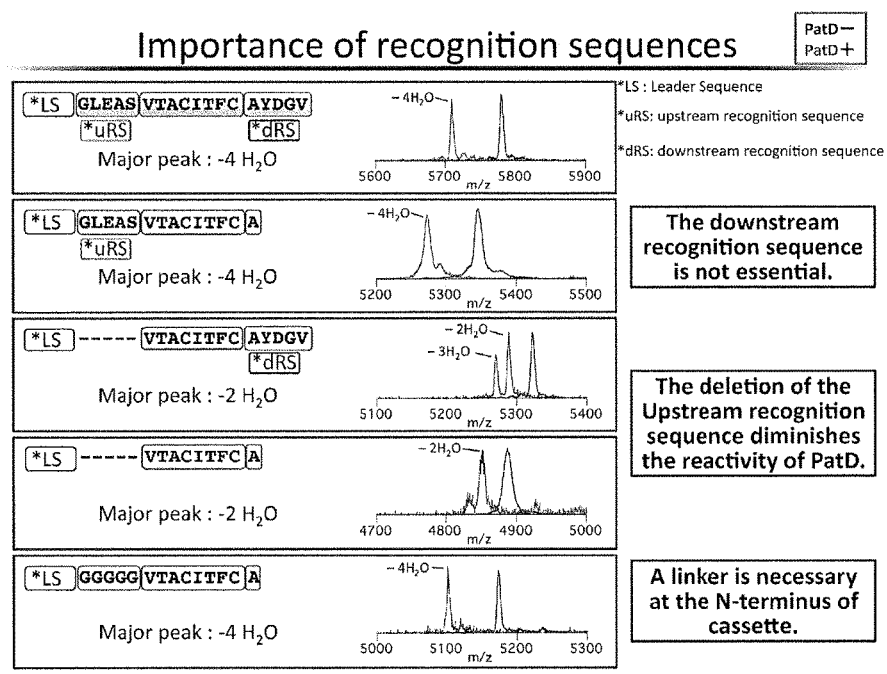

FIG. 9 shows the results of investigating the substrate acceptance of PatD while changing the recognition sequence. The corresponding sequence numbers of FIG. 9 are:
GLEAS=SEQ ID NO: 3,
VTACITFC=SEQ ID NO: 60,
AYDGV=SEQ ID NO: 6, and
GGGGG=SEQ ID NO: 173.

Figure 10A:
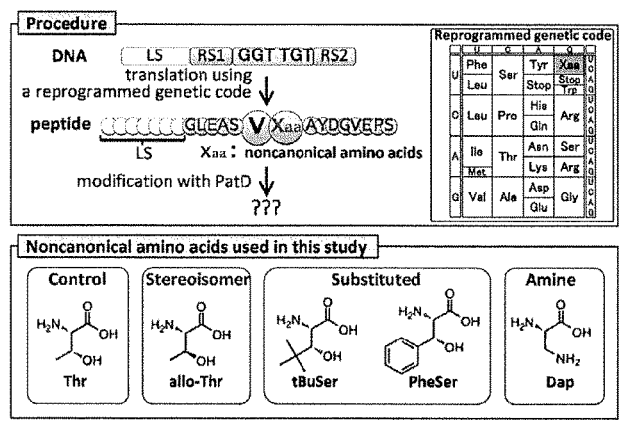

FIG. 10A shows the outline of a test to study the substrate acceptance of Pat D conducted by preparing a substrate containing a non-natural amino acid in the cassette sequence by translational synthesis. The corresponding sequence numbers of FIG. 10A are:
GLEAS=SEQ ID NO: 3 and
AYDGVEPS=SEQ ID NO: 5.

Figure 10B:
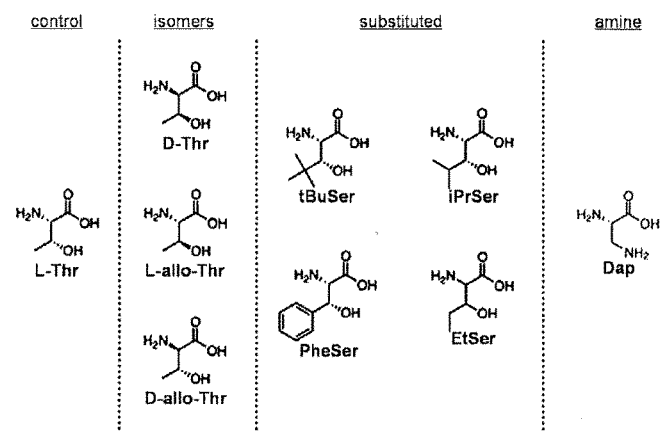

FIG. 10B shows non-natural amino acids used in the test of FIG. 10A.

Figure 11:
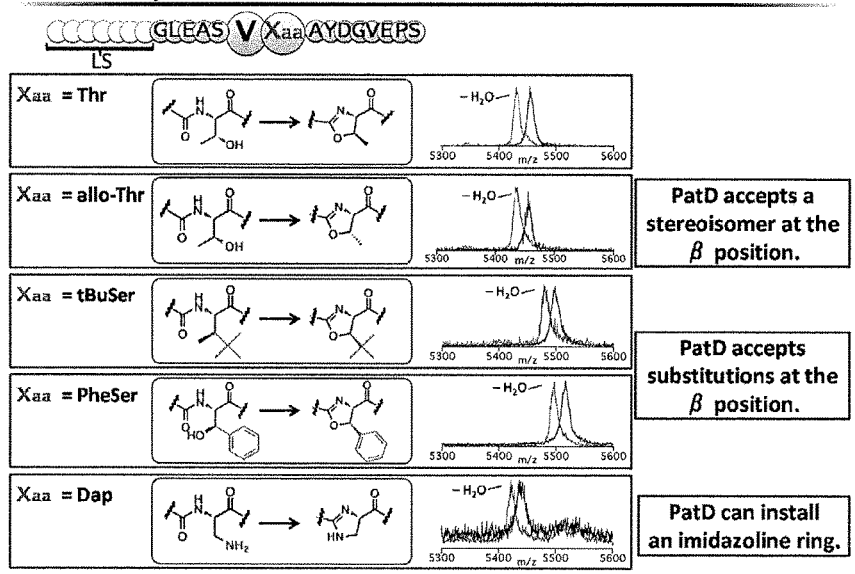

FIG. 11 shows typical results of the test of FIG. 10. The corresponding sequence numbers of FIG. 11 are:
GLEAS=SEQ ID NO: 3 and
AYDGVEPS=SEQ ID NO: 5.

Figure 12:
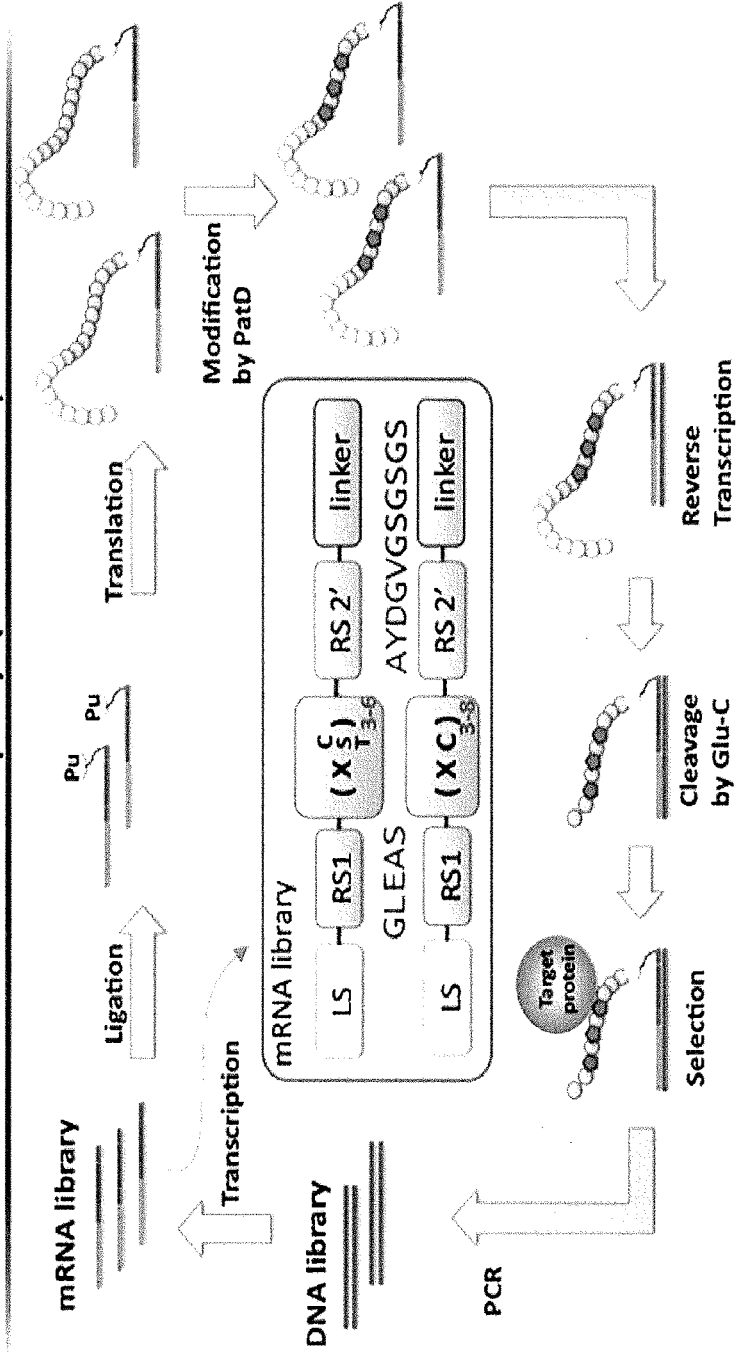

FIG. 12 shows the outline of screening using an mRNA display method. The corresponding sequence numbers of FIG. 12 are:
GLEAS=SEQ ID NO: 3 and
AYDGVGSGSGS=SEQ ID NO: 7.

Figure 13:
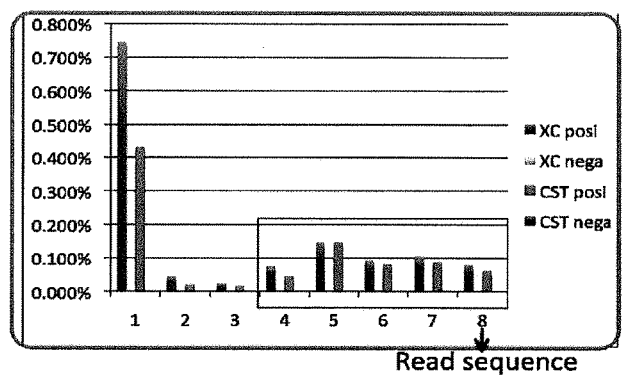

FIG. 13 shows the results of selection obtained by screening using the mRNA display method with MMP12 as a target.

Figure 14:
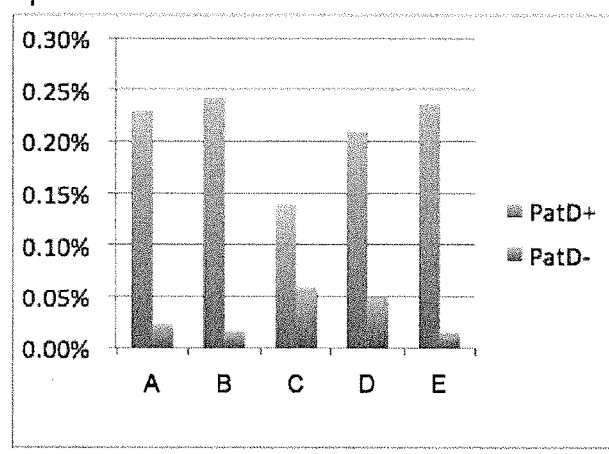

FIG. 14 shows the evaluation results of binding ability, to MMP12, of the azoline-containing compound selected by the method of FIG. 13.

Figure 15:
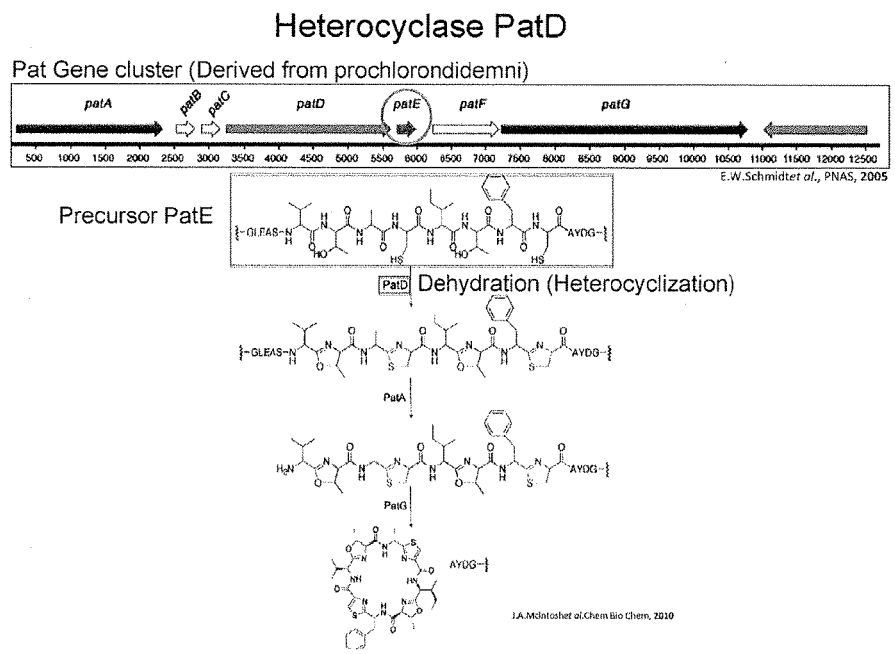

FIG. 15 is a schematic view showing the structure of a pat gene cluster and a biosynthesis pathway of patellamide. The corresponding sequence number of FIG. 15 is:
GLEAS=SEQ ID NO: 3.

Figure 16:
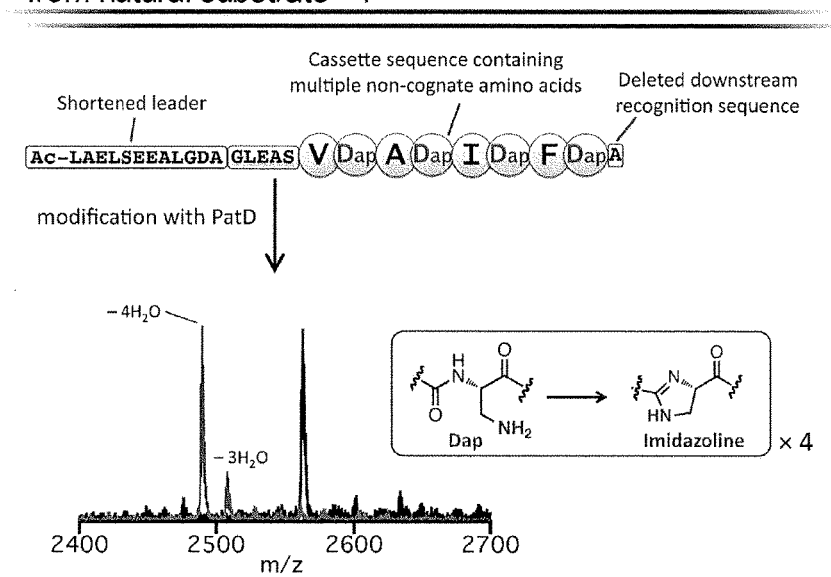

FIG. 16 shows an example of the results of investigating the substrate acceptance of PatD for a synthetic peptide significantly different from a natural substrate. The corresponding sequence number of FIG. 16 is SEQ ID NO: 222.

Figure 17:
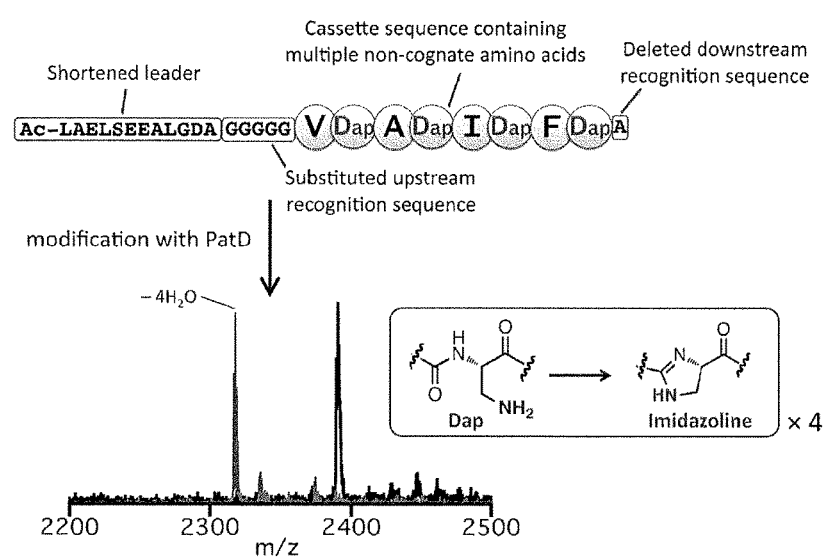

FIG. 17 shows an example of the results of investigating the substrate acceptance of PatD for a synthetic peptic significantly different from a natural substrate. The corresponding sequence number of FIG. 17 is SEQ ID NO: 223.

FIG. 18 shows the results of investigating the substrate acceptance of PatD in the case where as the leader sequence, a sequence derived from Lacticin 481 precursor or derived from human actin or a sequence obtained by shuffling the leader sequence of PatE is used. The corresponding sequence numbers of FIG. 18 from top to bottom are SEQ ID NOS: 178, 177, and 179, respectively.

FIG. 19 shows the results of investigating the substrate acceptance of PatD while deleting a portion of the leader sequence. The corresponding sequence number of FIG. 19 is SEQ ID NO: 1.

FIG. 20 shows the results of investigating the substrate acceptance of PatD while introducing point mutation into the leader sequence. The corresponding sequence numbers of FIG. 20 from top to bottom are SEQ ID NOS: 1, 260-317, respectively.

Figure 21:
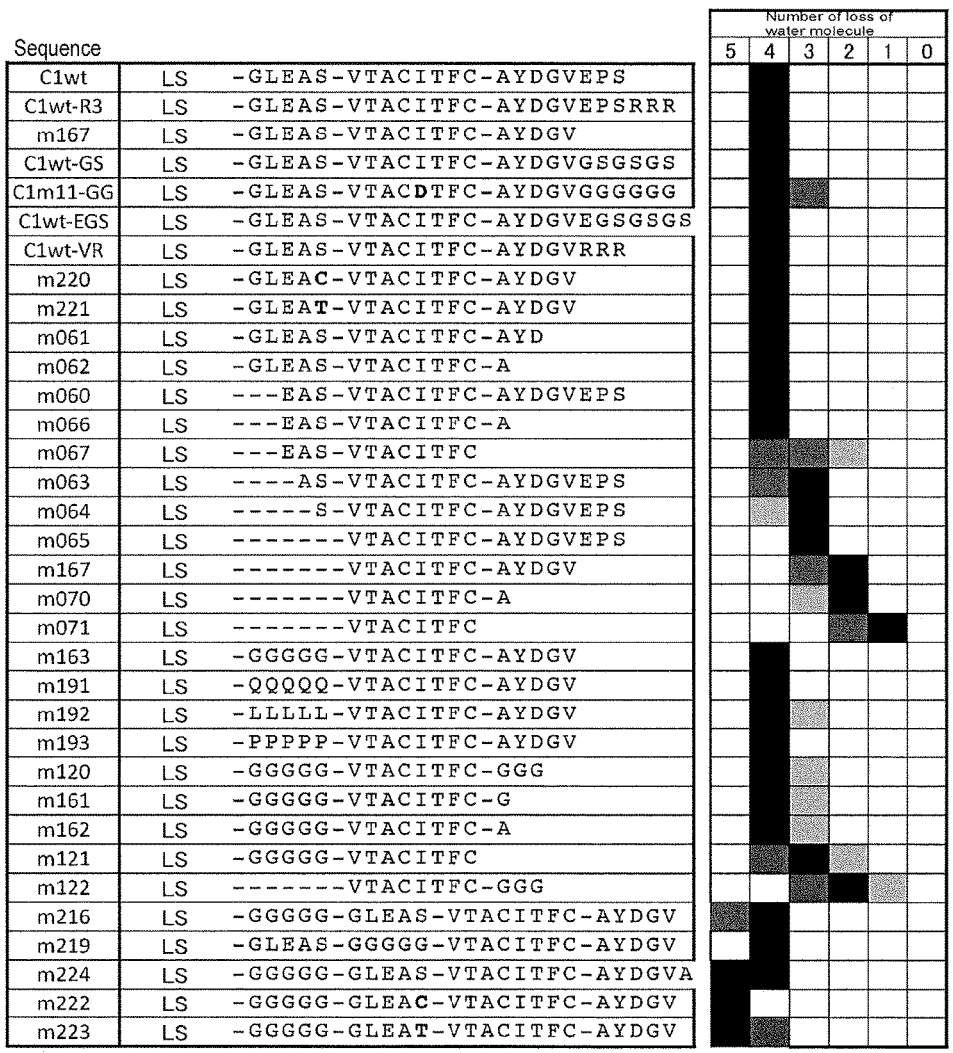

FIG. 21 shows the results of investigating the substrate acceptance of PatD while changing the recognition sequence. The corresponding sequence numbers of FIG. 21, following the leader sequence, from top to bottom are:
C1wt=(SEQ ID NO: 3)-(SEQ ID NO: 60)-(SEQ ID NO: 5),
C1wt-R3=(SEQ ID NO: 3)-(SEQ ID NO: 60)-(SEQ ID NO: 257),
m167=(SEQ ID NO: 3)-(SEQ ID NO: 60)-(SEQ ID NO: 6),
C1wt-GS=(SEQ ID NO: 3)-(SEQ ID NO: 60)-(SEQ ID NO: 7),
C1m11-GG=(SEQ ID NO: 3)-(SEQ ID NO: 20)-(SEQ ID NO: 8),
C1wt-EGS=(SEQ ID NO: 3)-(SEQ ID NO: 60)-(SEQ ID NO: 9),
C1wt-VR=(SEQ ID NO: 3)-(SEQ ID NO: 60)-(SEQ ID NO: 258),
m220=(SEQ ID NO: 2)-(SEQ ID NO: 60)-(SEQ ID NO: 6),
m221=(SEQ ID NO: 2)-(SEQ ID NO: 60)-(SEQ ID NO: 6),
m061=(SEQ ID NO: 3)-(SEQ ID NO: 60),
m062=(SEQ ID NO: 3)-(SEQ ID NO: 60),
m060=(SEQ ID NO: 60)-(SEQ ID NO: 5),
m066=(SEQ ID NO: 60),
m067=(SEQ ID NO: 60),
m063=(SEQ ID NO: 60)-(SEQ ID NO: 5),
m064=(SEQ ID NO: 60)-(SEQ ID NO: 5),
m065=(SEQ ID NO: 60)-(SEQ ID NO: 5),
m167=(SEQ ID NO: 60)-(SEQ ID NO: 6),
m070=(SEQ ID NO: 60),
m071=(SEQ ID NO: 60),
m163=(SEQ ID NO: 173)-(SEQ ID NO: 60)-(SEQ ID NO: 6),
m191=(SEQ ID NO: 174)-(SEQ ID NO: 60)-(SEQ ID NO: 6),
m192=(SEQ ID NO: 175)-(SEQ ID NO: 60)-(SEQ ID NO: 6),
m193=(SEQ ID NO: 176)-(SEQ ID NO: 60)-(SEQ ID NO: 6),
m120=(SEQ ID NO: 173)-(SEQ ID NO: 60),
m161=(SEQ ID NO: 173)-(SEQ ID NO: 60),
m162=(SEQ ID NO: 173)-(SEQ ID NO: 60),
m121=(SEQ ID NO: 173)-(SEQ ID NO: 60),
m122=(SEQ ID NO: 60),
m216=(SEQ ID NO: 173)-(SEQ ID NO: 3)-(SEQ ID NO: 60)-(SEQ ID NO: 6),
m219=(SEQ ID NO: 3)-(SEQ ID NO: 173)-(SEQ ID NO: 60)-(SEQ ID NO: 6),
m224=(SEQ ID NO: 173)-(SEQ ID NO: 3)-(SEQ ID NO: 60)-(SEQ ID NO: 259),
m222=(SEQ ID NO: 173)-(SEQ ID NO: 2)-(SEQ ID NO: 60)-(SEQ ID NO: 6), and m223=(SEQ ID NO: 173)-(SEQ ID NO: 2)-(SEQ ID NO: 60)-(SEQ ID NO: 6).

Figure 22:
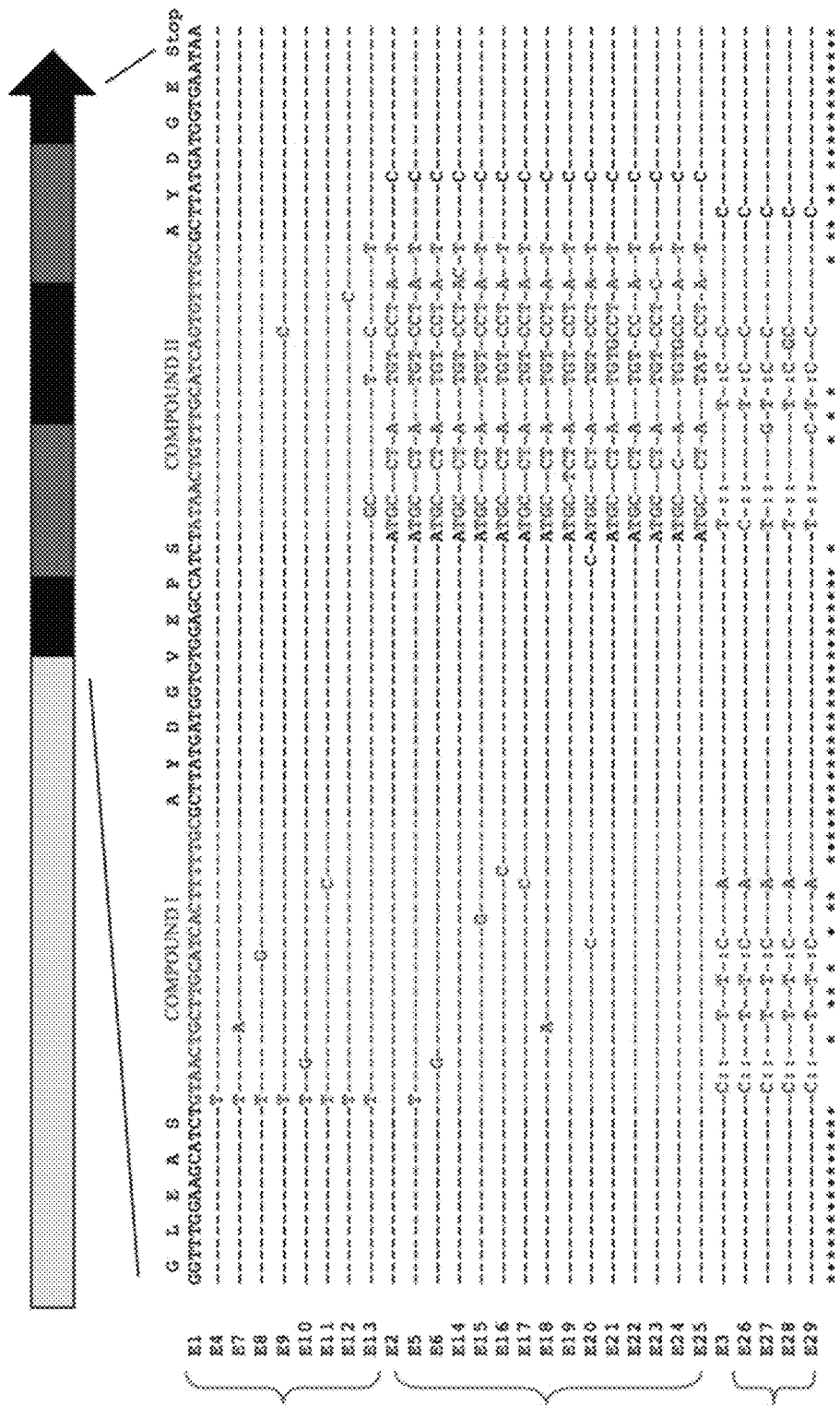

FIG. 22 shows Table 1. The corresponding sequence numbers of Table 1 are:
GLEAS=SEQ ID NO: 3,
AYDGVEPS=SEQ ID NO: 5,
AYDGE=SEQ ID NO: 318, and
E1-E29 (from top to bottom)=SEQ ID NOS: 319-347, respectively.

MODE FOR CARRYING OUT THE INVENTION (Construction Method of Azoline Compound Library)

The present invention provides a construction method of an azoline compound library including two or more azoline compounds.

The term "azoline compound" as used herein means a compound having an azoline backbone introduced into at least one of Cys, Ser, Thr, and 2,3-diamino acid, and analogs thereof of a peptide represented by the following formula (I):

A-(Xaa$_0$)$_m$-B  (I)

[wherein, m numbers of Xaa$_0$s represent arbitrary amino acids, at least one of which represents an amino acid selected from the group consisting of Cys, Ser, Thr, and 2,3-diamino acid, and analogs thereof, m represents an integer selected from 2 to 40, and A and B each independently represent a peptide composed of from 0 to 100 amino acids].

In one embodiment of the present invention, the azoline compound is represented by the formula (I) in which -(Xaa$_0$)$_m$- is -(Xaa$_1$-Xaa$_2$)$_n$- [wherein, n numbers of Xaa$_1$s each independently represent an arbitrary amino acid, n numbers of Xaa$_2$s each independently represent an amino acid selected from the group consisting of Cys, Ser, Thr, and 2,3-diamino acid, and analogs thereof, and n represents an integer selected from 1 to 20].

The Cys, Ser, Thr, and 2,3-diamino acid, and analogs thereof into which the azoline backbone has been introduced may be either at a position of Xaa$_1$ or at a position of Xaa$_2$.

The term "amino acid" is used herein in the broadest meaning and includes, in addition to natural amino acids, artificial amino acid mutants and derivatives. Examples of the amino acid as described herein include natural proteinogenic L-amino acids; D-amino acids; chemically modified amino acids such as amino acid mutants and derivatives; natural non-proteinogenic amino acids such as norleucine, β-alanine, and ornithine; and chemically synthesized compounds having properties known per se in the art and characteristic to amino acids. Examples of the non-natural amino acids include α-methylamino acids α-methylalanine, etc.), D-amino acid, histidine-like amino acids (β-hydroxy-histidine, homohistidine, α-fluoromethyl-histidine, α-methyl-histidine, etc.), amino acids ("homo" amino acids) having, on the side chain thereof, extra methylene, and amino acids (cysteic acid, etc.) obtained by substituting, with a sulfonic acid group, a side-chain amino acid with a carboxylic acid functional group.

The amino acid herein is represented by commonly used single-letter or three-letter code. The amino acids represented by single-letter or three-letter code include mutants and derivatives thereof.

Examples of the analogs of Thr include, but not limited to those represented by the following formula:

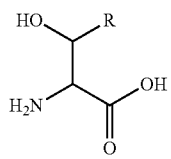

[Chemical formula 1]

[wherein, R represents a hydrogen atom, a substituted or unsubstituted alkyl group having from 1 to 10 carbon atoms, or a substituted or unsubstituted aromatic group].

Examples of the analogs of Cys include, but not limited to, those represented by the following formula:

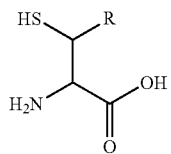

[Chemical formula 2]

[wherein, R represents a hydrogen atom, a substituted or unsubstituted alkyl group having from 1 to 10 carbon atoms, or a substituted or unsubstituted aromatic group].

Examples of the analogs of Ser or Thr include, but not limited to, those represented by the following formulas:

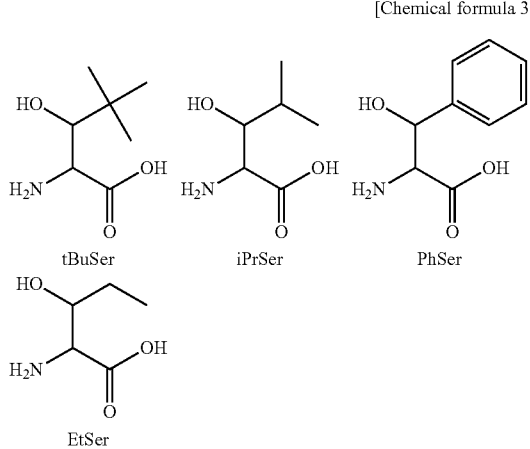

[Chemical formula 3]

tBuSer     iPrSer     PhSer

EtSer

Examples of the 2,3-diamino acid and analogs thereof include, but not limited to, those represented by the following formulas:

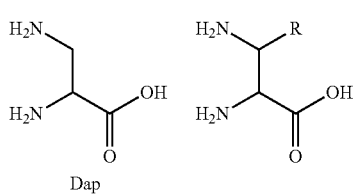

[Chemical formula 4]

Dap

[wherein, R represents a hydrogen atom, a substituted or unsubstituted alkyl group having from 1 to 10 carbon atoms, or a substituted or unsubstituted aromatic group].

The term "introducing an azoline backbone into at least one of Cys, Ser, Thr, and 2,3-diamino acid, and analogs thereof" as used herein means that a dehydration reaction occurs at Cys, Ser, Thr, or 2,3-diamino acid to introduce an azoline ring represented by the following formulas:

[Chemical formula 5]

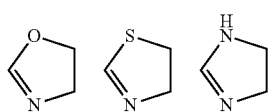

Introduction of an azoline backbone into Ser, Thr, Cys, or 2,3-diaminopropionic acid produces an oxazoline, thiazoline backbone, or an imidazoline backbone as follows:

[Chemical formula 6]

Ser:

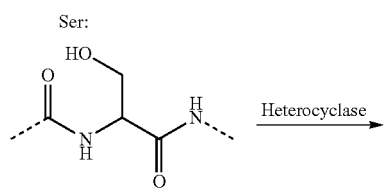

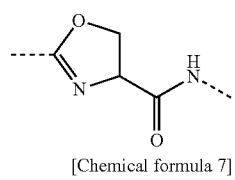

[Chemical formula 7]

Thr:

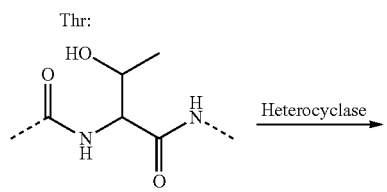

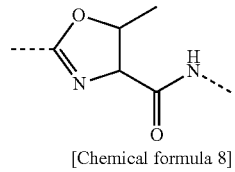

[Chemical formula 8]

Cys:

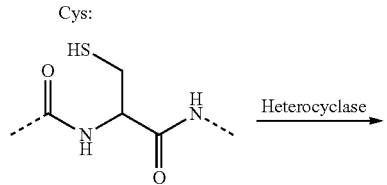

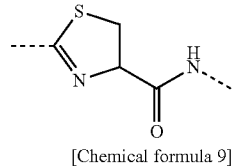

[Chemical formula 9]

2,3-Diaminopropionic acid:

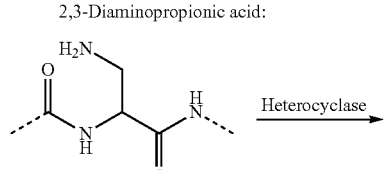

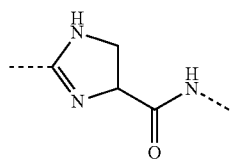

For example, introduction of an azoline backbone into the above-mentioned Thr analogue residue produces the following oxazoline backbone.

[Chemical formula 10]

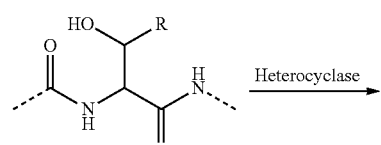

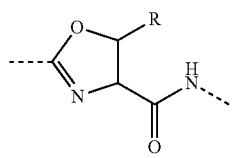

Introduction of an azoline backbone into the above-mentioned Cys analog residue produces the following imidazoline backbone.

[Chemical formula 11]

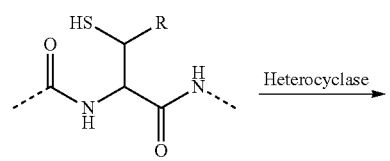

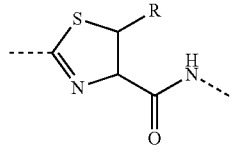

Introduction of an azoline backbone into the above-mentioned 2,3-diamino acid analog residue produces the following thiazoline backbone.

[Chemical formula 12]

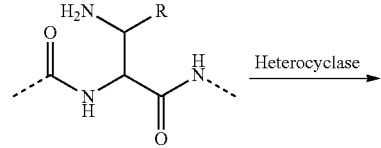

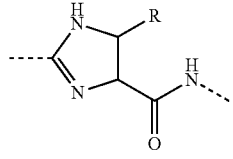

In the above formula (I), $Xaa_0$ represents an arbitrary amino acid insofar as it contains at least one of Cys, Ser, Thr, 2,3-diamino acid, and an analog thereof. As described above, although it has been considered that an azoline backbone-introducing enzyme such as PatD modifies only a cassette domain having 7 or 8 amino acids and having predetermined regularity, a wide sequence with m of from 2 to 40 becomes a substrate.

In the above-mentioned formula (I), $Xaa_1$s each independently represent an arbitrary amino acid. As described above, it has been conventionally considered that in peptide which is a substrate of an azoline backbone-introducing enzyme such as PatD, residues to be modified rarely be adjacent to each other, but as shown in Examples which will be described later, even if $Xaa_1$ represents Cys, Ser, or Thr and is the same amino acid as that of $Xaa_2$ adjacent thereto, the peptide of the formula (I) may be a substrate of an azoline backbone-introducing enzyme.

In addition, it has been conventionally considered that in peptide which may be a substrate of an azoline backbone-introducing enzyme such as PatD, many of residues other than Ser, Cys, and Thr are hydrophobic amino acid residues, but as shown later in Examples, a peptide having, as $Xaa_1$ thereof, a hydrophilic amino acid may be a substrate of an azoline backbone-introducing enzyme.

In the above formula (I), m represents an integer of 2 or greater, and 16 or less, 18 or less, 20 or less, 30 or less, or 40 or less; and n represents an integer of 1 or greater, and 8 or less, 9 or less, 10 or less, or 20 or less. As described above, it has conventionally been considered that in the peptide which may be a substrate of an azoline backbone-introducing enzyme such as PatD, m=7 or 8, meaning that n=3 or 4, but as will be shown later by Examples, the peptide of the formula (I) having, as m, 9 or greater and, as n, 5 or greater may also be a substrate of the azoline backbone-introducing enzyme.

In the above formula (I), A and B each independently represent a peptide composed of from 0 to 100 amino acids. A may contain the entirety or a portion of a recognition sequence 1 of an azoline backbone-introducing enzyme. It may contain the entirety or a portion of a leader sequence of PatE, a His tag, a linker, and the like. B may contain the entirety or a portion of a recognition sequence 2. It may contain a His tag, a linker, and the like. A and B each may have a length of, for example, 100, 70, 60, 50, 40, 30, 20, 10, 5, 2, 0 amino acid(s), but the length is not limited thereto. In A or B, one or several amino acids may be a modified amino acid or amino acid analog.

The construction method of an azoline compound library according to one embodiment of the present invention includes a step of constructing an mRNA library encoding a precursor peptide comprising, in order of mention from the N-terminus, the recognition sequence 1 of an azoline backbone-introducing enzyme, the $(Xaa_1\text{-}Xaa_2)_n$-, and the recognition sequence 2 of an azoline backbone-introducing enzyme.

The recognition sequences 1 and 2 of an azoline backbone-introducing enzyme are recognition sequences composed of from 0 to 10 amino acids and to be recognized by an azoline backbone-introducing enzyme. They may have any sequence insofar as the azoline backbone-introducing enzyme recognizes them and introduce an azoline backbone into $-(Xaa_0)_m$-. When the azoline backbone-introducing enzyme is PatD, for example, G(A/L/V) (G/E/D) (A/P) (S/T/C) (SEQ. ID NO: 2) can be used as the recognition sequence 1. It may be, for example, GLEAS (SEQ. ID NO: 3). As the recognition sequence 2 by the azoline backbone-introducing enzyme, that containing (A/S)Y(D/E)G(A/L/V) (SEQ ID NO:4) can be used. As such a sequence, for example, AYDGVEPS (SEQ ID NO: 5), AYDGV (SEQ ID NO: 6), AYDGVGSGSGS (SEQ ID NO: 7), AYDGVGGGGGG (SEQ ID NO: 8), or AYDGVEGSGSGS (SEQ ID NO: 9) may be used.

As shown later in Examples, the above-mentioned precursor peptide may become a substrate of the azoline backbone-introducing enzyme even if it does not have the recognition sequence 1 and/or 2, and thus the recognition sequences 1 and 2 are optional constituting elements of the precursor peptide.

Further, as shown later in Examples, the above-mentioned precursor peptide may become a substrate of the azoline backbone-introducing enzyme even if it uses a sequence utterly unrelated to sequences conventionally known as a recognition sequence.

In particular, the precursor peptide having the recognition sequence 1 on the N-terminus side of $-(Xaa_1\text{-}Xaa_2)_n$- is susceptible to modification with the azoline backbone-introducing enzyme but the sequence is not particularly limited insofar as it is present.

As the recognition sequence 1, a sequence, for example, GGGGG (SEQ ID NO: 173), QQQQQ (SEQ ID NO: 174), LLLLL (SEQ ID NO: 175), or PPPPP (SEQ ID NO: 176) may be used.

As will be described later, the above-mentioned precursor peptide may be fused further with a peptide having, on the N-terminus side thereof, a leader sequence.

The leader sequence, the recognition sequence 1 by the azoline ring-introducing enzyme, $-(Xaa_0)_m$-, and the recognition sequence 2 by the azoline ring-introducing enzyme may be adjacent to each other in the precursor peptide. The precursor peptide may have a sequence of from one to several amino acids between the leader sequence, the recognition sequence 1, $-(Xaa_0)_m$-, and the recognition sequence 2 insofar as it is expressed as a precursor peptide in a cell-free expression system and is subjected to modification with the azoline ring-introducing enzyme.

An mRNA library encoding $-(Xaa_0)_m$- can be constructed by synthesizing a DNA containing a sequence such as —$(NNN)_n$-, -$(NNK)_n$—, —$(NNT)_n$-, or -$(NNG)_n$- and transcribing it. Here, the "N" means any one of A, C, G, and T; "K" means either one of G and T; NNN and NNK each mean any one of 20 protein amino acids; and NNU and NNG encode any one of 15 and 14 protein amino acids, respectively.

An mRNA library encoding $-(Xaa_1\text{-}Xaa_2)n$- can be constructed, for example, by synthesizing a DNA containing a sequence such as —$(NNK\text{-}WST)_n$- or -$(NNK\text{-}TGT)_n$- and transcribing it. Here, N means any one of A, C, G, and T; K means either one of G and T; W means either one of A and T; and S means either one of C and G. NNN and NNK each encode any one of 20 protein amino acids; WSU encodes any one of Ser, Thr, and Cys; and UGU encodes Cys.

When such a constitution is employed, a sufficient size of library can be obtained. For example, in the case of $-(Xaa_0)_m$- and m=10, $20^{10}$ kinds of variants can be prepared theoretically even from only 20 natural amino acids; and in the case of $-(Xaa_1\text{-}Xaa_2)_n$- and n=5, $20^5 \times 3^5$ kinds of mutants can be prepared.

By synthesizing a DNA encoding $-(Xaa_0)_m$-, containing, at the 5' end thereof, a DNA encoding the recognition sequence 1 and, at the 3' end thereof, a DNA encoding the recognition sequence 2 and transcribing it, an mRNA encoding a precursor peptide comprising the recognition sequence 1, $-(Xaa_1\text{-}Xaa_2)_n$-, and the recognition sequence 2 can be obtained. By synthesizing a DNA further containing, on the 5' end side of the DNA encoding the recognition sequence 1, a DNA encoding a leader sequence and transcribing it, an mRNA encoding a precursor peptide comprising the leader sequence, the recognition sequence 1, -(Xaa$_1$-Xaa$_2$)$_n$-, and the recognition sequence 2 can be obtained.

The construction method of an azoline compound library according to one embodiment of the present invention includes a step of using the above-mentioned mRNA library to express the above-mentioned precursor peptide with a cell-free translation system and thereby constructing a peptide library.

The cell-free translation system contains, for example, ribosome protein, aminoacyl tRNA synthetase (ARS), ribosome RNA, amino acid, GTP, ATP, translation initiation factor (IF), extension factor (EF), release factor (RF), ribosome regeneration factor (RRF), and other factors necessary for translation. An *Escherichia coli* extract or wheat germ extract may be used for enhancing the expression efficiency. Alternatively, a rabbit erythrocyte extract or insect cell extract may be used.

From several hundred micrograms to several milligram/mL of proteins can be produced by continuously supplying the system containing them with energy under dialysis. The system may contain an RNA polymerase for simultaneously conducting transcription from a gene DNA. Commercially available cell-free translation systems that can be used include *E. coli*-derived systems such as "RTS-100" (registered trademark), product of Roche Diagnostics and "PURE-SYSTEM" (registered trademark), product of PGI and systems using a wheat germ extract available from ZOEGENE Corporation and CellFree Sciences Co., Ltd.

When the cell-free translation system is used, a peptide can be modified in one pot by adding a post-translation modification enzyme to the same container without purifying an expression product.

The construction method of an azoline compound library according to one embodiment of the present invention includes a step of reacting an azoline backbone-introducing enzyme and the above-mentioned peptide library in the presence of a peptide comprising a leader sequence of a substrate of the azoline backbone-introducing enzyme, and thereby introducing an azoline backbone into at least one of Cys, Ser, Thr, and 2,3-diamino acid, and analogs thereof. More specifically, an oxazoline backbone is introduced into Ser and Thr, a thiazoline backbone is introduced into Cys, and an imidazoline backbone is introduced into 2,3-diamino acid.

The leader sequence is a sequence that facilitates modification with the azoline backbone-introducing enzyme and any sequence may be used insofar as it satisfies this object. As will be described later in Examples, the precursor peptide comprising the recognition sequence 1, -(Xaa$_1$-Xaa$_2$)$_n$-, and the recognition sequence 2 may become a substrate of the azoline backbone-introducing enzyme without the leader sequence. The leader sequence may be composed of, for example, about 5 amino acids, about 7 amino acids, about 10 amino acids, about 20 amino acids, about 30 amino acids, about 40 amino acids, or about 50 amino acids.

As the leader sequence, for example, a peptide composed of the following amino acid sequence; a partial sequence of this amino acid sequence; or an amino acid sequence obtained by deleting, adding, or substituting one to several amino acids in this amino acid sequence may be used.

MNKKNILPQQGQPVIRLTAGQLSSQLAELSEEAL-GDA (SEQ ID NO: 1)

The partial sequence of the amino acid sequence having SEQ ID NO: 1 is a sequence containing at least four successive amino acids, five successive amino acids, or six successive amino acids of this amino acid sequence. Although no particular limitation is imposed on the position of these amino acids in SEQ ID No: 1, the partial sequence contains four amino acids, five amino acids, or six amino acids, for example, at the C-terminus of the amino acid sequence of SEQ ID NO: 1.

Further, as will be shown later in Examples, the above-mentioned precursor peptide may become a substrate of an azoline backbone-introducing enzyme even when using, as the leader sequence, a sequence entirely unrelated to a leader sequence of PatE conventionally known as the leader sequence.

For example, as the leader sequence, a sequence such as MKEQNSFNLLQEVTESELDLILGA (SEQ ID NO: 177) derived from another peptide (Lacticin 481 precursor), a sequence such as MILASLSTFQQMWISKQEYDEAGDA (SEQ ID NO: 178) derived from human actin, or a sequence such as MELQLRPSGLEKKQAPISELNIAQTQGGD-SQVLALNA (SEQ ID NO: 179) obtained by shuffling the leader sequence of PatE.

As the leader sequence, a sequence having high helicity (α helicity) may be used.

In the phrase "in the presence of a peptide comprising a leader sequence of a substrate of the azoline backbone-introducing enzyme" as used herein, the peptide may be, in the reaction system, present as an independent peptide from the precursor peptide comprising the recognition sequence 1, -(Xaa$_1$-Xaa$_2$)$_n$-, and the recognition sequence 2 or have been fused with the precursor peptide comprising the recognition sequence 1, -(Xaa$_1$-Xaa$_2$)$_n$-, and the recognition sequence 2.

In the substrate of natural PatD, the leader sequence, recognition sequence 1, cassette sequence, and recognition sequence 2 are fused with each other, but as will be shown later in Examples, the present inventors have found that in reacting the precursor peptide comprising the recognition sequence 1, —(Xaa$_1$-Xaa$_2$)$_n$-, and the recognition sequence 2 with the azoline backbone-introducing enzyme, the precursor peptide may become a substrate of the azoline backbone-introducing enzyme even if the leader sequence is added to the reaction system as an independent peptide.

When the leader sequence is allowed to exist as a peptide independent from the precursor peptide comprising the recognition sequence 1, -(Xaa$_1$-Xaa$_2$)$_n$-, and the recognition sequence 2, each of these peptides (that is, the peptide comprising the leader sequence and the precursor peptide) becomes shorter, which makes preparation easy. When the leader sequence is fused to the precursor peptide, the leader sequence is desirably cleaved therefrom prior to screening, because there is a possibility of causing steric hindrance when the peptide is bound to a target molecule. When the peptide comprising the leader sequence is originally allowed to exist as a peptide independent from the precursor peptide, cleaving of it therefrom is not necessary.

These two peptides may be prepared by either translational synthesis or chemical synthesis.

Examples of the azoline backbone-introducing enzyme include PatD and enzymes having homology therewith. As the enzyme having homology with PatD, those included in the report of Lee, etc. (Lee, S. W. et al., PNAS vol. 105, No. 15, 5879-5884, 2008) may be used, but it is not limited to them.

The azoline backbone-introducing enzyme may be extracted/purified from microorganisms producing the azoline backbone-introducing enzyme or may be expressed by gene recombination. For example, an azoline backbone-introducing enzyme can be expressed in *Escherichia coli* as a construct having at the N-terminus thereof a His tag and purified by making use of the His tag according to a conventional manner. The azoline backbone-introducing enzyme may be a mutant thereof insofar as it has an azoline backbone introducing ability.

The reaction between the azoline backbone-introducing enzyme and the peptide library can be conducted by adding the azoline backbone-introducing enzyme in the container in which the precursor peptide was expressed, that is, in one pot without purifying the precursor peptide. The reaction between the azoline backbone-introducing enzyme and the peptide library can be conducted under appropriate conditions selected by those skilled in the art and for example, when the azoline backbone-introducing enzyme is PatD, the conditions are selected within a range of a final concentration of from 0.1 µM to 50 µM, a reaction temperature of from 4° C. to 45° C., and a reaction time of from 5 minutes to 100 hours.

Confirmation of the reaction can be conducted by measuring a mass change by using, for example, MALDI-TOF MS.

As the construction method of an azoline compound library according to one embodiment of the present invention, when the leader sequence is fused with the precursor peptide comprising the recognition sequence 1, -(Xaa$_1$-Xaa$_2$)$_n$-, and the recognition sequence 2, a step of cleaving the leader sequence from the precursor peptide may be conducted. This facilitates binding of a cassette domain portion represented by -(Xaa$_0$)$_m$- to a target substance.

Cleavage of the leader sequence can also be conducted by adding a peptidase in the container where the reaction of the azoline backbone-introducing enzyme was conducted.

Cleavage of the leader sequence may be conducted by cleaving in the middle of the leader sequence, in the middle of the recognition sequence 1, at the binding site between the leader sequence and the recognition sequence 1, at the binding site between the recognition site 1 and the cassette domain, and at the binding site between the cassette domain and the recognition site 2. The kind of a peptidase may be selected depending on the sequence at the cleavage site. Examples of the peptidase include, but not limited to, trypsin, Glu-C, Lys-C, Asp-N, Lys-N, Arg-C, thrombin, Factor Xa, prescission protease, TEV protease, entherokinase, and HRV 3C Protease.

As one example, when GLEAS (SEQ ID NO: 3) is used the recognition sequence 1 of the azoline backbone-introducing enzyme, endoproteinase Glu-C can be used and cleaving is conducted between Glu and Ala. The reaction of Glu-C can be conducted in a known manner.

In one embodiment of the construction method of an azoline compound library according to the present invention, an azoline compound library containing at least two complexes between an azoline compound and an mRNA encoding the peptide represented by the formula (I) is constructed. This makes it possible to apply the azoline compound library to mRNA display (Nemoto, N. et al., FE BS Lett. 1997, 405-408; Roberts, R. W. and Szostak, J. W. Proc. Natl. Acad. Sci. USA 1997, 94, 12297-12302).

By using such an azoline compound-mRNA complex library and conducting screening of an azoline compound that binds to a target substance, it is possible to obtain a cDNA-containing complex by a reverse transcription reaction of the azoline compound-mRNA complex selected and determine the base sequence of it.

The azoline compound-mRNA complex can be prepared, for example, by binding puromycin to the 3' end of each of mRNAs of the mRNA library in a known manner to prepare a puromycin-bound mRNA library and expressing a precursor peptide in a cell-free translation system by using this puromycin bound mRNA library.

After preparation of the peptide-mRNA complex library in such a manner, it is reacted with PatD and then a leader sequence is cleaved if necessary to obtain an azoline compound library.

In the construction method of an azoline compound library according to one embodiment of the present invention, at least one of peptides represented by the formula (I) has at least one of the following characteristics (i) to (iv):

(i) m represents from 2 to 40 (with the proviso that 7 and 8 are excluded) and m is, for example, 2, 3, 4, 5, 6, 9, 10, 12, 14, 16, 20, 30, or 40;

(ii) n represents from 1 to 20 (with the proviso that 3 and 4 are excluded) and n is, for example, 1, 2, 5, 6, 7, 8, 10, 15, or 20;

(iii) at least one, at least two, at least three, at least four, or at least five of Xaa$_1$s is (are) an amino acid selected from Cys, Ser, Thr, and 2,3-diamino acid, and analogs thereof; and (iv) at least one, at least two, at least three, at least four, or at least five of Xaa$_1$s is (are) a hydrophilic amino acid.

Peptides having at least one of the characteristics of (i) to (iv) include peptides which have conventionally been considered unsuitable as a substrate of the azoline backbone-introducing enzyme such as PatD and the present inventors have confirmed, for the first time, that they become a substrate of the azoline backbone-introducing enzyme.

The following are cassette sequences confirmed for the first time as a substrate of the azoline backbone-introducing enzyme.

TABLE 3

| Mutant | -(Xaa$_0$)m- | SEQ ID NO: |
|---|---|---|
| C1m1 | VTACIT | 10 |
| C1m2 | VTACITFCVT | 11 |
| C1m3 | VTATITFT | 12 |
| C1m4 | VCACICFC | 13 |
| C1m5 | VSASISFS | 14 |
| C1m6 | VTADITFC | 15 |
| C1m7 | VTANITFC | 16 |
| C1m8 | VTAKITFC | 17 |
| C1m9 | CFTICATV | 18 |
| C1m10 | VTACITFCVTIC | 19 |
| C1m11 | VTACDTFC | 20 |
| C1m12 | VTACNTFC | 21 |
| C1m13 | VTACKTFC | 22 |
| C1m14 | VCACDCFC | 23 |
| C1m15 | VCACNCFC | 24 |
| C1m16 | VCACKCFC | 25 |
| C1mI7 | VCATITFT | 26 |
| C1m18 | VTACITFT | 27 |
| C1m19 | VTATICFT | 28 |

TABLE 3 -continued

| Mutant | -(Xaa$_0$)m- | SEQ ID NO: |
|---|---|---|
| C1m20 | VTATITFC | 29 |
| C1m21 | CFCICACV | 30 |
| C1m22 | DTACITFC | 31 |
| C1m23 | NTACITFC | 32 |
| C1m24 | KTACITFC | 33 |
| C1m25 | VTACETFC | 34 |
| C1m26 | VTACDTFC | 35 |
| C1m27 | VTACHTFC | 36 |
| C1m28 | VTACRTFC | 37 |
| C1m29 | VTACPTFC | 38 |
| C1m30 | VFALIMFC | 39 |
| C1m31 | VFALIMCC | 40 |
| C1m32 | VFALCCCC | 41 |
| C1m33 | VCACRCFC | 42 |
| C1m34 | RTACITFC | 43 |
| C1m35 | VFALCCCC | 44 |
| C1m36 | RCDCDCRC | 45 |
| C1m37 | VCACICFCVCACVC | 46 |
| C1m38 | VCACICFCVCACVCIC | 47 |
| C1m39 | VTATDTFT | 48 |
| C1m40 | VSASDSFS | 49 |

TABLE 4

| C1m41 | VTATITFTVTIT | 50 |
|---|---|---|
| C1m42 | RCRCICFCVCACVC | 51 |
| C1m43 | VCACICRCRCACVC | 52 |
| C1m44 | VCACICFCVCRCRC | 53 |
| C1m45 | VTATICFC | 54 |
| C1m46 | VCATITFC | 55 |
| C1m47 | VCACITFT | 56 |
| C1m48 | VCATICFT | 57 |

TABLE 4-2

| Mutant | -(Xaa$_0$)m- | SEQ ID NO: |
|---|---|---|
| m049 | VC | |
| m050 | VCAC | |
| m051 | VCACICFCVCACVCICYCFCIC | |
| m052 | VCACICFCVCVCFCYCACYCIC FCACVCICYCFCIC | |

TABLE 4-2 -continued

| Mutant | -(Xaa$_0$)m- | SEQ ID NO: |
|---|---|---|
| m053 | RTDTDTRT | |
| m054 | RSDSDSRS | |
| m055 | CCCCCC | |
| m056 | TTTTTT | |
| m057 | SSSSSS | |
| m058 | VFATITFT | |
| m059 | CFATITFT | |
| m068 | VFALCCCC | |
| m119 | VT | |
| m196 | VTAC | |
| m197 | VTACITFCVTAC | |
| m198 | VTACITFCVTACVSIC | |
| m199 | VTACITFCVTACVSICYTFCIT | |
| m200 | VTACITFCVTACVSICYTFCIT FCATVCISYCFTIC | |
| m201 | VTACITFCVTACVTIC | |
| m202 | VTACITFCVTACVTICYTFCIT | |
| m203 | VTACITFCVTACVTICYTFCIT FCATVCITYCFTIC | |

The corresponding sequence numbers of Table 4-2 from top to bottom are SEQ ID NOS: 180-200, respectively.

In the construction method of an azoline compound library according to one embodiment of the present invention, at least one of the azoline compounds has 5 or more azoline backbones.

It has conventionally been considered that 5 or more azoline backbones can not be introduced into the cassette domain of natural PatE even if an azoline backbone-introducing enzyme is used. The present inventors for the first time succeeded in synthesis of an azoline compound having 5 or more azoline backbones.

In one embodiment of the construction method of an azoline compound library according to the present invention, at least one of the azoline compounds has an azoline backbone other than ordinary oxazoline/thiazoline obtained from Ser/Thr/Cys.

It has conventionally been considered that an azoline backbone is not introduced into an amino acid other than Ser, Thr, and Cys present in the cassette domain of natural PatE even if an azoline backbone-introducing enzyme is used. The present inventors have for the first time synthesized compounds in which an imidazoline backbone or a substituted azoline backbone derived from non-protein amino acids such as Dap, tBuSer, iPrSer, PhSer, and EtSer has been introduced using an azoline backbone-introducing enzyme such as PatD.

The construction method of an azoline compound library according to one embodiment of the present invention includes a step of macrocyclizing an azoline compound before or after cleavage of the leader sequence. Macrocyclization of an azoline compound can be conducted in a known method of macrocyclizing a peptide or a method equivalent thereto. For example, it can be conducted in accordance with the method disclosed in WO2008/117833 or the method of Timmerman, et al. (Timmerman, P et al., ChemBioChem 2005, 6: 821-824).

(Construction Method of Azole Compound Library)

The present invention also provides a construction method of an azole compound library containing two or more azole compounds. Of the terms used in the construction method of an azole compound library according to the present invention, those also used in the above-mentioned construction method of an azoline compound library are regarded as having the same meanings unless otherwise particularly specified.

The term "azole compound" as used herein means a compound having an azole backbone introduced into at least one of Cys, Ser, Thr, and 2,3-diamino acid, and analogs thereof of a peptide represented by the following formula (I):

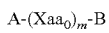

[wherein, m numbers of $Xaa_0$s represent arbitrary amino acids, at least one of which is an amino acid selected from the group consisting of Cys, Ser, Thr, and 2,3-diamino acid, and analogs thereof, m represents an integer selected from 2 to 20, and A and B each independently represents a peptide composed of from 0 to 8 amino acids).

In one embodiment of the present invention, the azole compound is a compound of the formula (I) in which -$(Xaa_0)_m$- is -$(Xaa_1$-$Xaa_2)_n$-

[wherein, n numbers of $Xaa_1$ each independently represent an arbitrary amino acid, n numbers of $Xaa_2$ each independently represent an amino acid selected from the group consisting of Cys, Ser, Thr, and 2,3-diamino acid, and analogs thereof, and n represents an integer selected from 1 to 10].

The Cys, Ser, Thr, and 2,3-diamino acid, and analogs thereof into which the azole backbone has been introduced may be either at a position of $Xaa_1$ or at a position of $Xaa_2$.

The term "introducing an azole backbone into at least one of Cys, Ser, Thr, and 2,3-diamino acid, and analogs thereof" as used herein means that an oxidation reaction of an azoline ring produced by the dehydration reaction of Cys, Ser, or Thr proceeds to introduce an azole ring represented by the following formulas:

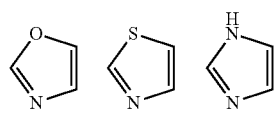

[Chemical formula 13]

Introduction of an azole backbone into Ser, Thr, Cys, or 2,3-diamino acid produces an oxazole, thiazole, or imidazole backbone as follows:

Ser:

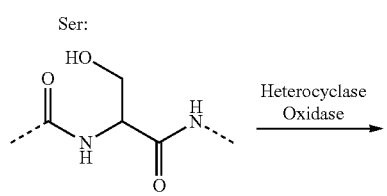

[Chemical formula 14]

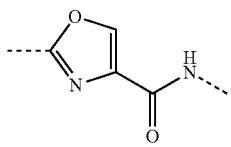

[Chemical formula 15]

Thr:

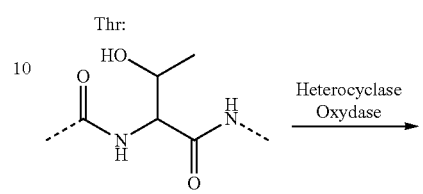

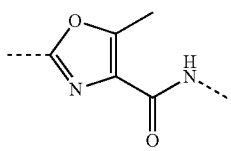

[Chemical formula 16]

Cys:

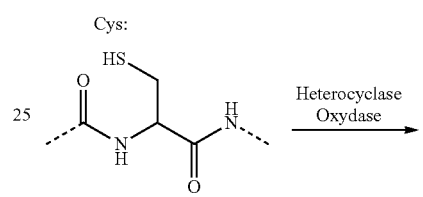

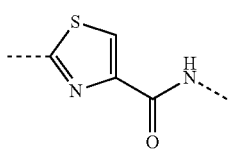

[Chemical formula 17]

Dap:

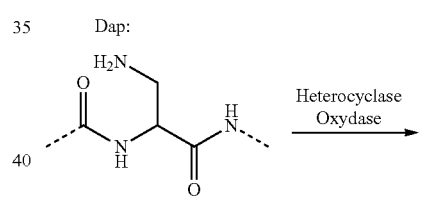

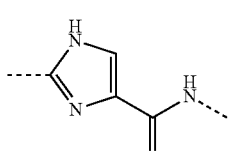

For example, introduction of an azole backbone into the above-mentioned artificial Thr analog residue produces the following oxazole backbone.

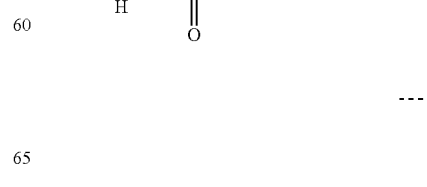

[Chemical formula 18]

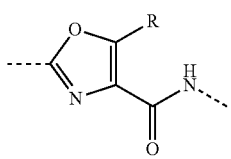

Introduction of an azole backbone into the above-mentioned artificial Cys analog residue produces the following thiazole backbone.

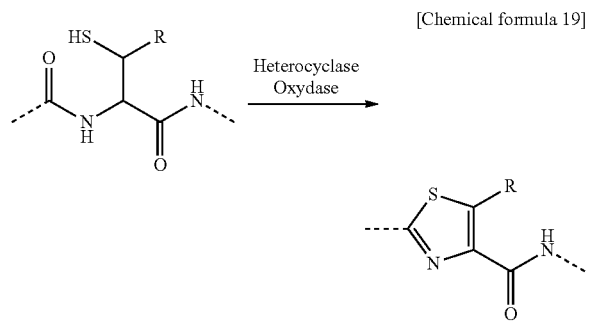

[Chemical formula 19]

Introduction of an azole backbone into the above-mentioned artificial diamino acid analog residue produces the following imidazole backbone.

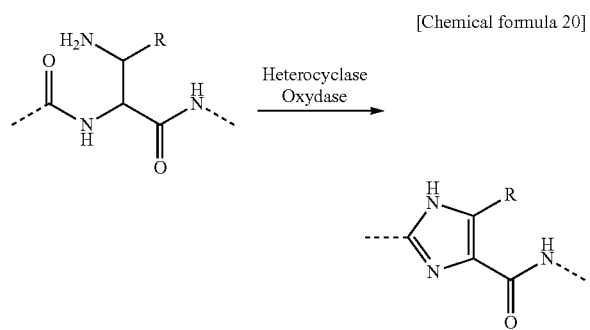

[Chemical formula 20]

In the construction method of an azole compound library according to one embodiment of the present invention, an azoline backbone-introducing step in the above-mentioned construction method of an azole compound library is followed by a step of reacting the library having azoline backbones introduced therein with an azole backbone-introducing enzyme to convert at least one of the azoline backbones into an azole backbone. The oxazoline backbone introduced into Ser or Thr, the thiazoline backbone introduced into Cys, and an imidazoline backbone introduced into 2,3-diamino acid are converted into an oxazole backbone, a thiazole backbone, and an imidazole backbone, respectively. The step of reacting the library having an azoline backbone introduced therein with the azole backbone-introducing enzyme may be conducted in the presence of a peptide comprising a leader sequence of a substrate of the azole backbone-introducing enzyme. The peptide comprising a leader sequence of a substrate of the azole backbone-introducing enzyme may be the same as or different from the peptide comprising a leader sequence of a substrate of the azoline backbone-introducing enzyme.

Examples of the azole backbone-introducing enzyme include PatG and enzymes having homology therewith. Examples of the enzymes having homology with PatG include, but not limited to, those included in the report of Lee, et al. (Lee, S. W. et al., PNAS vol. 105, No. 15, 5879-5884, 2008).

The reaction with the azole backbone-introducing enzyme can be conducted by adding the azole backbone-introducing enzyme in the container in which the reaction with the azoline backbone-introducing enzyme has been conducted.

In the construction method of an azole compound library according to one embodiment of the present invention, a mutant obtained by deleting a peptidase domain from PatG or a mutant which has lost its peptidase activity by point mutation is used as the azole backbone-introducing enzyme. PatG is comprised of two domains and in natural one, an oxidase domain at the N-terminus is involved in conversion of an azoline backbone constructed by PatD into an azole backbone, while a peptidase domain at the C-terminus is involved in cleaving of the peptide site and macrocyclization after modification. Accordingly, in the construction method of an azole compound library according to the present invention, a peptidase domain-deficient mutant or a mutant that has lost its peptidase activity as a result of point mutation can be used.

(Azoline Compound Library)

The present invention also provides an azoline compound library containing two or more azoline compounds. Of the terms used here, those also used in the above-mentioned construction method of a library are regarded as having the same meanings unless otherwise particularly specified.

The azoline compound library according to one embodiment of the present invention includes at least one of azoline compounds having at least one of the following characteristics (i) to (iv):

(i) m represents from 2 to 20 (with the proviso that 7 and 8 are excluded) and m is, for example, 2, 3, 4, 5, 6, 9, 10, 12, 14, 16, 20, 30, or 40;

(ii) n represents from 1 to 10 (with the proviso that 3 and 4 are excluded) and n is, for example, 1, 2, 5, 6, 7, 8, 10, 15, or 20;

(iii) at least one, at least two, at least three, at least four, or at least five of $Xaa_1$s is (are) an amino acid selected from Cys, Ser, Thr, and 2,3-diamino acid, and analogs thereof; and (iv) at least one, at least two, at least three, at least four, or at least five of $Xaa_1$s is (are) a hydrophilic amino acid.

Peptides having at least one of the characteristics of (i) to (iv) include peptides which have conventionally been considered unsuitable as a substrate of the azoline backbone-introducing enzyme such as PatD and the present inventors have confirmed for the first time that they become a substrate of the azoline backbone-introducing enzyme.

In the azoline compound library according to one embodiment of the present invention, azoline compounds each constitute a complex with mRNA encoding the peptide portion thereof. The library may be applicable to mRNA display.

In the azoline compound library according to one embodiment of the present invention, the entirety or a portion of the recognition sequence by the azoline backbone-introducing enzyme may have been bound to the N-terminus and C-terminus of the peptide represented by the formula (I).

The recognition sequence of the azoline backbone-introducing enzyme is necessary for modifying the peptide, which has been expressed in a cell-free translation system, with the azoline backbone-introducing enzyme. When an azoline compound library is constructed using the method of the present invention and the leader sequence is cleaved using a peptidase, the entirety or a portion of these sequences may remain at the N-terminus and C-terminus.

For example, supposing that the recognition sequence 1 is GLEAS (SEQ ID NO: 3) and the leader sequence is cleaved using Glu-C, Ala-Ser remains on the N-terminus side of the cassette domain.

(Azole Compound Library)

The present invention also provides an azole compound library containing two or more azole compounds. Of the terms used here, those also used in the above-mentioned construction method of a library are regarded as having the same meanings unless otherwise particularly specified.

The azole compound library according to one embodiment of the present invention includes at least one of azole compounds having at least one of the following characteristics (i) to (iv):

(i) m represents from 2 to 20 (with the proviso that 7 and 8 are excluded) and m is, for example, 2, 3, 4, 5, 6, 9, 10, 12, 14, 16, 20, 30, or 40;

(ii) n represents from 1 to 10 (with the proviso that 3 and 4 are excluded) and n is, for example, 1, 2, 5, 6, 7, 8, 10, 15, or 20;

(iii) at least one, at least two, at least three, at least four, or at least five of $Xaa_1$s is (are) an amino acid selected from Cys, Ser, Thr, and 2,3-diamino acid, and analogs thereof; and (iv) at least one, at least two, at least three, at least four, or at least five of $Xaa_1$s is (are) a hydrophilic amino acid.

Peptides having at least one of the characteristics (i) to (iv) include peptides which have conventionally been considered unsuitable as a substrate of the azoline backbone-introducing enzyme such as PatD and the present inventors have confirmed for the first time that they become a substrate of the azoline backbone-introducing enzyme. It is therefore understood that an azole backbone may be introduced by introducing an azoline backbone by using the azoline backbone-introducing enzyme and then conducting modification with the azole backbone-introducing enzyme.

In the azole compound library according to one embodiment of the present invention, the azole compounds each constitute a complex with mRNA encoding the peptide portion thereof. The library may be applicable to mRNA display.

In the azole compound library according to one embodiment of the present invention, the entirety or a portion of the recognition sequence of PatD may have been bound to the N-terminus and C-terminus of the peptide represented by the formula (I).

The recognition sequence of PatD is necessary for modifying the peptide, which has been expressed in a cell-free translation system, with PatD. When an azole compound library is constructed using the method of the present invention and the leader sequence is cleaved using a peptidase, the entirety or a portion of these sequences may remain at the N-terminus and C-terminus.

For example, supposing that the recognition sequence 1 is GLEAS (SEQ ID NO: 3) and the leader sequence is cleaved using Glu-C, Ala-Ser remains on the N-terminus side of the cassette domain.

(Screening Method of Azoline Compound)

The present invention provides a screening method for identifying an azoline compound that binds to a target substance.

The screening method according to one embodiment of the present invention includes a step of bringing the azoline compound library constructed by the construction method of the present invention or the azoline compound library according to the present invention into contact with a target substance; and incubating the resulting compound.

The target substance is not particularly limited herein and may be, for example, a small molecular compound, a high molecular compound, a nucleic acid, a peptide, a protein, or the like. In particular, according to the library of the present invention, a target substance having a protease activity can also be used.

The target substance, for example, immobilized on a solid phase support may be brought into contact with the library of the present invention. The "solid phase support" to be used herein is not particularly limited insofar as it is a carrier onto which a target substance can be immobilized and examples include microtiter plates, a substrate and beads made of glass, a metal, a resin, or the like, nitrocellulose membrane, nylon membrane, and PVDF membrane. The target substance can be immobilized onto such a solid phase support in a known manner.

The target substance and the library may be brought into contact with each other in a buffer selected as needed and reacted while controlling pH, temperature, time, or the like.

The screening method according to one embodiment of the present invention may further include a step of selecting the azoline compound bound to the target substance. The azoline compound may be labeled using a known method capable of detectably labeling peptides before it is bound to the target substance. After the step of bringing them into contact, the surface of the solid phase support may be washed with a buffer to detect the azoline compound which has bound to the target substance.

Examples of the detectable label include enzymes such as peroxidase and alkaliphosphatase, radioactive substances such as $^{125}$I, $^{131}$I, $^{35}$S, and $^3$H, fluorescent substances such as fluorescein isothiocyanate, rhodamine, dansyl chloride, phycoerythrin, tetramethyl rhodamine isothiocyanate, and infrared fluorescent materials, light-emitting substances such as luciferase, luciferin, and aequorin, and nanoparticles such as gold colloid and quantum dot. When the label is an enzyme, the azoline compound can be detected by adding a substrate of the enzyme to develop a color. The peptide may also be detected by binding biotin thereto and then binding avidin or streptavidin labeled with an enzyme or the like to the biotin-bound peptide.

It is possible not only to detect or analyze the presence/absence or degree of binding but also to analyze the enhanced or inhibited activity of the target substance and thereby identify an azoline compound having such enhancing or inhibitory activity. Such a method makes it possible to identify an azoline compound having physiological activity and useful as a pharmaceutical.

When the azoline compound library is comprised of azoline compound-mRNA complexes, after an azoline compound bound to a target substance is selected by the above-mentioned method, a step of analyzing the base sequence of the mRNA of the azoline compound thus selected may be conducted.

The analysis of the base sequence of mRNA can be conducted by synthesizing cDNA by using a reverse transcription reaction and then, analyzing the base sequence of the resulting cDNA. This makes it possible to easily specify the relationship between a genotype and a phenotype.

An azoline compound having strong binding ability to the target substance may be concentrated by conducting transcription further after the reverse transcription reaction to convert the library into the mRNA library again, and repeating screening with the target compound.

(Screening Method of Azole Compound)

The present invention provides a screening method for identifying an azole compound that binds to a target substance.

The screening method according to one embodiment of the present invention may include a step of bringing the azole compound library constructed using the construction method of an azole compound library according to the present invention or the azole compound library according to the present invention into contact with a target substance, followed by incubation.

The screening method of an azole compound can be conducted in accordance with the above-mentioned screening method of an azoline compound.

(Screening Kit)

The present invention provides a screening kit of an azoline compound or azole compound.

The screening kit according to one embodiment of the present invention includes an azoline compound library or azole compound library constructed by the construction method of the present invention or the azoline compound library or azole compound library according to the present invention. The screening kit of the present invention includes, in addition, a reagent and an apparatus necessary for detecting the binding between a target substance and an azoline compound or azole compound. Examples of such a reagent and apparatus include, but not limited to, solid phase supports, buffers, labeling reagents, enzymes, enzyme reaction terminator solutions, and microplate readers.

In the screening kit of the present invention, the library may be immobilized in array form on a solid phase support.

(Preparation Method of Azoline Compound)

The present invention provides a method of preparing an azoline compound in which at least one azoline backbone has been introduced into at least one of Cys, Ser, Thr, and 2,3-diamino acid, and analogs thereof of $Xaa_0$ of a peptide represented by the formula (I).

This method includes:

a step of preparing an mRNA encoding a precursor peptide having, in order of mention from the N-terminus, a recognition sequence 1 by an azoline backbone-introducing enzyme, $-(Xaa_0)_m-$, and a recognition sequence 2 by an azoline backbone-introducing enzyme (the recognition sequences 1 and 2 meaning recognition sequences by an azoline backbone-introducing enzyme composed of from 0 to 10 amino acids);

a step of expressing a precursor peptide in a cell-free translation system by using the above-mentioned mRNA; and a step of reacting the azoline backbone-introducing enzyme and the precursor peptide in the presence of a peptide having a leader sequence of a substrate of the azoline backbone-introducing enzyme to introduce an azoline backbone into at least one of Cys, Ser, Thr, and 2,3-diamino acid, and analogs thereof of $Xaa_0$.

The peptide having a leader sequence and the precursor peptide having a recognition sequence 1, $-(Xaa_0)_m-$, and a recognition sequence 2 are separate peptides.

According to this method, the peptide having a leader sequence and the precursor peptide having a recognition sequence 1, $-(Xaa_0)_m-$, and a recognition sequence 2 may be made shorter, respectively, so that they can be prepared easily. For the preparation, chemical synthesis, translational synthesis and combination of them can be employed. Prior to screening, separation of the leader sequence is not necessary.

The present method is therefore particularly advantageous when an azoline compound that binds to a target substance is identified by using the screening method of the present invention and then, the azoline compound is mass produced.

(Preparation Method of Azole Compound)

The present invention embraces a preparation method of an azole compound by using the azoline compound obtained using the above-mentioned preparation method of an azoline compound.

The present method includes a step of reacting an azoline compound and an azole backbone-introducing enzyme in the presence of a peptide having a leader sequence of a substrate of the azole backbone-introducing enzyme and thereby converting at least one of azoline backbones into an azole backbone.

According to the present method, preparation of an azole compound may be easily prepared because the peptide comprising a leader sequence and the azoline compound may each be made shorter. The preparation may be conducted using chemical synthesis, translational synthesis, or combination of them. In addition, prior to screening, separation of the leader sequence is not necessary.

The present method is therefore particularly advantageous for, after identification of an azole compound that binds to a target substance, mass production of the azole compound.

(Kit for Preparing Azoline Compound or Azole Compound)

The kit for preparing an azoline compound or an azole compound according to the present invention serves to prepare an azoline compound or azole compound by using the above-mentioned method so that it includes an azoline backbone-introducing enzyme or azole backbone-introducing enzyme and a peptide having a leader sequence of a substrate of the azole backbone-introducing enzyme.

In addition, the present kit may include necessary reagents and instruments, an instruction manual, and the like.

Example

The present invention will next be described more specifically based on Example. It should however be borne in mind that the present invention is not limited to or by the Example.

Figure 1:
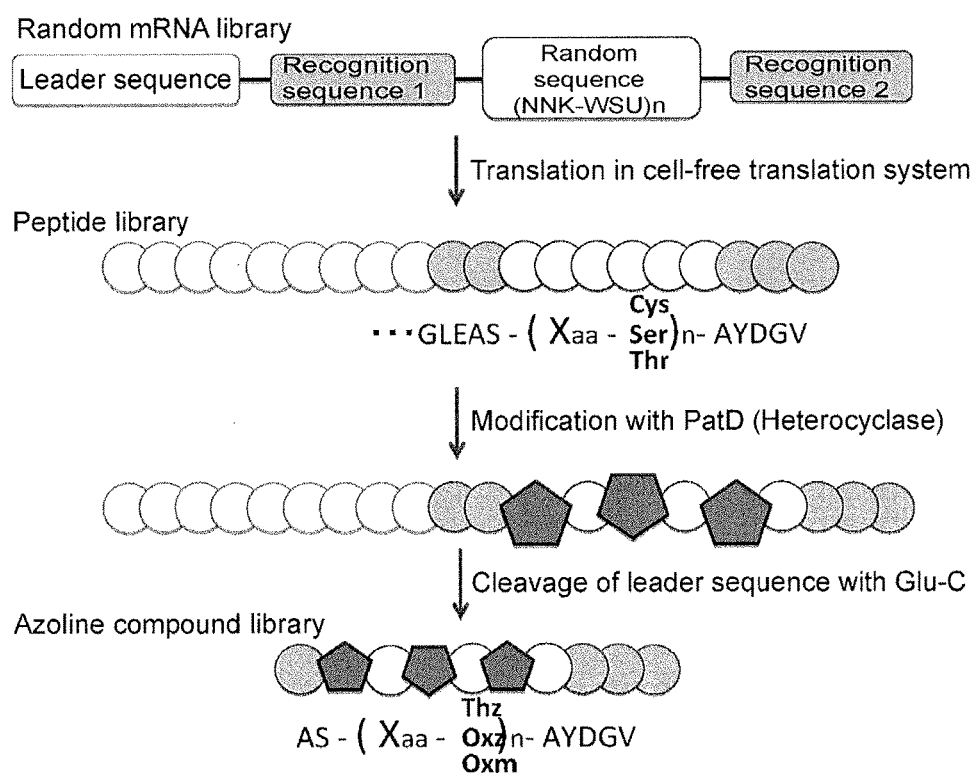
FIG. 1 is a schematic view showing one embodiment of a method of constructing an azoline compound library according to the present invention. The corresponding sequence numbers of FIG. 1 are:
GLEAS=SEQ ID NO: 3 and
AYDGV=SEQ ID NO: 6.

Synthesis scheme of an azoline compound library in the following Example is shown in FIG. 1.

[1] Expression and Purification of PatD

A PatD gene was inserted into a pET16b plasmid to prepare a construct plasmid containing at the N-terminus thereof a 10×His tag. It was transformed into an *E. coli* BL21(DE3)pLysS strain, followed by culturing at 30° C. When O.D. reached 0.4, 0.1 mM of IPTG was added to induce expression, followed by culturing overnight at 16° C. The cells collected were suspended in a lysis buffer (1 M NaCl, 10 mM Imidazole, 50 mM HEPES-Na (pH7.5)) and then lysed ultrasonically. The sample was filtered and purified using a His-Trap HP column. The column was equilibrated in advance with 10 CV of Buffer A (500 mM NaCl, 25 mM imidazole, 50 mM HEPES-Na (pH7.5)) and after injection of the sample therein, the protein was eluted from the column by gradually increasing the concentration of Buffer B (500 mM NaCl, 500 mM imidazole, 50 mM HEPES-Na (pH7.5)) to obtain a pure PatD fraction. The sample thus obtained was concentrated to about 4 times with Amicon Ultra (Millipore) 30 kDa. Then, buffer was exchanged with Storage Buffer (200 mM NaCl, 25 mM HEPES (pH7.5), 10% glycerol) by using PD-10 (GE Lifescience) and the resulting sample was stored at −80°.

[2] Construction of PatE Plasmid (pET16b)

The following PatE sequence was subcloned into pET16b.

(SEQ ID NO: 58)
ATGAACAAGAAAAACATCCTGCCCCAACAAGGTCAACCGGTTATCCGCTTAACCGCAGG

ACAGTTGAGCTCGCAACTCGCCGAACTGTCTGAAGAAGCACTGGGCGACGCGGGGTTGG

AGGCAAGCGTTACGGCGTGTATCACGTTTTGTGCGTACGATGGCGTTGAGCCATCTATT

ACGGTCTGCATTAGTGTCTGCGCCTATGATGGGGAGTAA

[3] Preparation of DNA of Substrate Peptide
[3-1] Preparation of PatEpre

DNA of PatEpre was prepared by conducting PCR twice with the PatE plasmid as a template. The underlined portion is DNA encoding GLEAS (SEQ ID NO: 3) of the recognition sequence 1. The region from position 48 to position 153 of SEQ ID NO: 59 is a code region of the leader sequence.

(SEQ ID NO: 59)
GGCGTAATACGACTCACTATAGGGTTAACTTTAACAAGGAGAAAAACATGAACAAGAAA

AACATCCTGCCCCAACAAGGTCAACCGGTTATCCGCTTAACCGCAGGACAGTTGAGCTC

GCAACTCGCCGAACTGTCTGAAGAAGCACTGGGCGACGCGGGGTTGGAGGCAAGC

PatEpre encodes a peptide composed of the following amino acid sequence having the leader sequence and the recognition sequence (underlined portion). MNKKNIL-PQQGQPVIRLTAGQLSSQLAELSEEALGDAGLEAS (SEQ ID NO: 201)

MNKKNILPQQGQPVIRLTAGQLSSQLAELSEEALGDAGLEAS

Primers used for PCR of PatEpre are shown in the following table. The sequence of the primers is shown in a primer list which will be shown later.

TABLE 5

| final product | 1st F primer | 1st R primer | 2nd F primer | 2nd R primer |
|---|---|---|---|---|
| PatEpre | pre-Ion a | pre-Ion c | pre-Ion b | pre-Ion c |

[3-2] Preparation of DNA of Substrate Peptide

[3-2-1] Peptide having AYDGVEPS (SEQ ID NO: 5) as the recognition sequence 2

A mutant DNA having mutation in the cassette domain thereof was prepared by conducting PCR twice or three times with PatEpre as a template. The peptide thus obtained had the following sequence:

(SEQ ID NO: 202)
MNKKNILPQQGQPVIRLTAGQLSSQLAELSEEALGDAGLEAS (XXX)
AYDGVEPS

The sequence in (XXX) corresponding to the cassette domain and primers used are shown below. The sequence of the primers is shown in the primer list which will be described later.

TABLE 6

| mutant | Amino acid sequence in (XXX) | SEQ ID NO: | F primer | 1st R primer | 2nd R primer | 3rd R primer |
|---|---|---|---|---|---|---|
| C1wt | VTACITFC | 60 | T7ex5 | wt-a | wt-b | — |
| C1m1 | VTACIT | 10 | T7ex5 | m1-a | m1-b | — |
| C1m2 | VTACITFCVT | 11 | T7ex5 | m2-a | m2-b | — |
| C1m3 | VTATITFT | 12 | T7ex5 | m3-a | m3-b | — |
| C1m4 | VCACICFC | 13 | T7ex5 | m4-a | m4-b | — |
| C1m5 | VSASISFS | 14 | T7ex5 | m5-a | m5-b | — |
| C1m6 | VTADITFC | 15 | T7ex5 | m6-a | wt-b | — |
| C1m7 | VTANITFC | 16 | T7ex5 | m7-a | wt-b | — |
| C1m8 | VTAKITFC | 17 | T7ex5 | m8-a | wt-b | — |
| C1m9 | CFTICATV | 18 | T7ex5 | m9-a | m9-b | — |
| C1m10 | VTACITFCVTIC | 19 | T7ex5 | m10-a | m10-b | m10-c |
| C1m11 | VTACDTFC | 20 | T7ex5 | m11-a | wt-b | — |

TABLE 6 -continued

| mutant | Amino acid sequence in (XXX) | SEQ ID NO: | F primer | 1st R primer | 2nd R primer | 3rd R primer |
|---|---|---|---|---|---|---|
| C1m12 | VTACNTFC | 21 | T7ex5 | m12-a | wt-b | — |
| C1m13 | VTACKTFC | 22 | T7ex5 | m13-a | m13-b | — |
| C1m14 | VCACDCFC | 23 | T7ex5 | m14-a | m14-b | — |
| C1m15 | VCACNCFC | 24 | T7ex5 | m15-a | m15-b | — |
| C1m16 | VCACKCFC | 25 | T7ex5 | m16-a | m16-b | — |
| C1m17 | VCATITFT | 26 | T7ex5 | m17-a | m3-b | — |
| C1m18 | VTACITFT | 27 | T7ex5 | m18-a | m3-b | — |
| C1m19 | VTATITFT | 28 | T7ex5 | m19-a | m19-b | — |
| C1m20 | VTATITFC | 29 | T7ex5 | m20-a | wt-b | — |
| C1m21 | CFCICACV | 30 | T7ex5 | m21-a | m21-b | — |
| C1m22 | DTACITFC | 31 | T7ex5 | m22-a | wt-b | — |
| C1m23 | NTACITFC | 32 | T7ex5 | m23-a | wt-b | — |
| C1m24 | KTACITFC | 33 | T7ex5 | m24-a | wt-b | — |
| C1m25 | VTACETFC | 34 | T7ex5 | m25-a | m25-b | — |
| C1m26 | VTACOTFC | 35 | T7ex5 | m26-a | m26-b | — |
| C1m27 | VTACHTFC | 36 | T7ex5 | m27-a | wt-b | — |
| C1m28 | VTACRTFC | 37 | T7ex5 | m28-a | wt-b | — |
| C1m29 | VTACPTFC | 38 | T7ex5 | m29-a | m29-b | — |
| C1m30 | VFALIMFC | 39 | T7ex5 | m30-a | m30-b | — |
| C1m31 | VFALIMCC | 40 | T7ex5 | m31-a | m31-b | — |
| C1m32 | VFALICCC | 41 | T7ex5 | m32-a | m32-b | — |
| C1m33 | VCACRCFC | 42 | T7ex5 | m33-a | m33-b | — |
| C1m34 | RTACITFC | 43 | T7ex5 | m34-a | wt-b | — |
| C1m35 | VFALCCCC | 44 | T7ex5 | m35-a | m35-b | — |
| C1m36 | RCDCDCRC | 45 | T7ex5 | m36-a | m36-b | — |
| C1m37 | VCACICFCVCACVC | 46 | T7ex5 | m37-a | m37-b | m10-c |
| C1m38 | VCACICFCVCACVCIC | 47 | T7ex5 | m37-a | m38-b | m38-c |

TABLE 7

| | | | | | |
|---|---|---|---|---|---|
| c1m39VTATDTFT | 48 | T7ex5 | m39-a | m3-b | — |
| C1m40VSASDSFS | 49 | T7ex5 | m40-a | m40-b | — |
| C1m41VTATITFTVTIT | 50 | T7ex5 | m41-a | m41-b | m10-c |
| C1m42RCRCICFCVCACVC | 51 | T7ex5 | m42-a | m37-b | m10-c |
| C1m43VCACICRCRCACVC | 52 | T7ex5 | m43-a | m43-b | m10-c |

TABLE 7 -continued

| | | | | | |
|---|---|---|---|---|---|
| C1m44VCACICFCVCRCRC | 53 | T7ex5 | m44-a | m44-b | m10-c |
| C1m45VTATICFC | 54 | T7ex5 | m45-a | m45-b | — |
| C1m46VCATITFC | 55 | T7ex5 | m46-a | wt-b | — |
| C1m47VCACITFT | 56 | T7ex5 | m47-a | m3-b | — |
| C1m48VCATICFT | 57 | T7ex5 | m48-a | m19-b | — |

TABLE 7-2

| mutant | Amino acid sequence in (XXX) | SEQ ID NO: | F primer | 1st R primer | 2nd R primer | 3rd R primer | 4th R primer |
|---|---|---|---|---|---|---|---|
| m049 | VC | | T7ex5.F22 | m49 | m10-c | — | — |
| m050 | VCAC | | T7ex5.F22 | m50 | m10-c | — | — |
| m051 | VCACICFCVCACVCICYCFCIC VCACICFCVCVCFCYCACYCICFCA | | T7ex5.F22 | m51-a | m51-b | — | — |
| m052 | CVCICYCFCIC | | T7ex5.F22 | m52-a | m52-b | m51-b | — |
| m053 | RTDTDTRT | | T7ex5.F22 | m53-a | m53-b | — | — |
| m054 | RSDSDSRS | | T7ex5.F22 | m54-a | m54-b | — | — |
| m055 | CCCCCC | | T7ex5.F22 | m55 | m35-N-b | — | — |
| m056 | TTTTTT | | T7ex5.F22 | m56 | m1-b | — | — |
| m057 | SSSSSS | | T7ex5.F22 | m57-c | m57-d | — | — |
| m058 | VFATITFT | | T7ex5.F22 | m58 | m3-b | — | — |
| m059 | CFATITFT | | T7ex5.F22 | m59 | m3-b | — | — |
| m068 | VFALCCCC | | T7ex5.F22 | m68 | m10-c | — | — |
| m119 | VT | | T7ex5.F22 | m119 | m10-c | — | — |
| m196 | VTAC | | T7ex5.F22 | m196 | m10-c | — | — |
| m197 | VTACITFCVTAC | | T7ex5.F22 | m197 | m10-c | — | — |
| m198 | VTACITFCVTACVSIC | | T7ex5.F22 | m198-a | m198-b | m10-c | — |
| m199 | VTACITFCVTACVSICYTFCIT VTACITFCVTACVSICYTFCITFCAT | | T7ex5.F22 | m199-a | m199-b | m10-c | — |
| m200 | VCISYCFTIC | | T7ex5.F22 | m199-a | m200-a | m200-b | m10-c |
| m201 | VTACITFCVTACVTIC | | T7ex5.F22 | m198-a | m201 | m10-c | — |
| m202 | VTACITFCVTACVTICYTFCIT VTACITFCVTACVTICYTFCITFCAT | | T7ex5.F22 | m202-a | m202-b | m10-c | — |
| m203 | VCITYCFTIC | | T7ex5.F22 | m202-a | m203-a | m203-b | m10-c |

The corresponding sequence numbers of Table 7-2 from top to bottom are SEQ ID NOS: 180-200, respectively.

[3-2-2] Peptides Other than Those Having AYDGVEPS (SEQ ID NO: 5) as Recognition Sequence 2

Similarly, PCR was conducted twice or three times with PatEpre2 as a template and DNA of a peptide having, as a C-terminus sequence, a sequence other than AYDGVEPS (SEQ ID NO: 5) was also prepared.

MNKKNILPQQGQPVIRLTAGQLSSQLAELSEEAL-GDAGLEAS(XXX)(YYY) (SEQ ID NO: 203)

MNKKNILPQQGQPVIRLTAGQLSSQLAELSEEALGDAGLEAS (XXX)

(YYY)

The (XXX) represents a cassette domain and the (YYY) represents a recognition sequence 2.

TABLE 8

| | (XXX) Sequence | SEQ ID NO: | (YYY) Sequence | SEQ ID NO: |
|---|---|---|---|---|
| wt-dgv | VTACITFC | 60 | AYDGV | 6 |
| m3-dgv | VTATITFT | 12 | AYDGV | 6 |

TABLE 8-continued

| | (XXX) Sequence | SEQ ID NO: | (YYY) Sequence | SEQ ID NO: |
|---|---|---|---|---|
| m5-dgv | VSASISFS | 14 | AYDGV | 6 |
| m11-dgv | VTACDTFC | 20 | AYDGV | 6 |
| m12-dgv | VTACNTFC | 21 | AYDGV | 6 |
| m13-dgv | VTACKTFC | 22 | AYDGV | 6 |
| m31-dgv | VFALIMCC | 40 | AYDGV | 6 |
| m32-dgv | VFALICCC | 41 | AYDGV | 6 |
| wt-GS | VTACITFC | 60 | AYDGVGSGSGS | 7 |
| m3-GS | VTATITFT | 12 | AYDGVGSGSGS | 7 |
| m4-GS | VCACICFC | 13 | AYDGVGSGSGS | 7 |
| m5-GS | VSASISFS | 14 | AYDGVGSGSGS | 7 |
| m11-GS | VTACDTFC | 20 | AYDGVGSGSGS | 7 |
| m12-GS | VTACNTFC | 21 | AYDGVGSGSGS | 7 |

TABLE 8-continued

| (XXX) Sequence | SEQ ID NO: | (YYY) Sequence | SEQ ID NO: |
|---|---|---|---|
| m13-GS | VTACKTFC | 22 | AYDGVGSGSGS | 7 |
| m20-GS | VTATITFC | 29 | AYDGVGSGSGS | 7 |
| m32-GS | VFALICCC | 41 | AYDGVGSGSGS | 7 |
| m3-GG | VTATITFT | 12 | AYDGVGGGGGG | 8 |
| m5-GG | VSASISFS | 14 | AYDGVGGGGGG | 8 |
| m11-GG | VTACDTFC | 20 | AYDGVGGGGGG | 8 |
| m12-GG | VTACNTFC | 21 | AYDGVGGGGGG | 8 |
| m13-GG | VTACKTFC | 22 | AYDGVGGGGGG | 8 |
| m32-GG | VFALICCC | 41 | AYDGVGGGGGG | 8 |
| wt-EGS | VTACITFC | 60 | AYDGVEGSGSGS | 9 |
| m11-EGS | VTACDTFC | 20 | AYDGVEGSGSGS | 9 |

Primers used for DNA preparation were shown below. The sequence of the primers was shown in the primer list which will be shown later.

TABLE 9

| | F primer | 1st R primer | 2nd R primer | 3rd R primer |
|---|---|---|---|---|
| wt-dgv | T7ex5 | wt-a | wt-aydgv | — |
| m3-dgv | T7ex5 | m3-a | m3-b | mT-aydgv |
| m5-dgv | T7ex5 | m5-a | m5-b | mS-aydgv |
| m11-dgv | T7ex5 | m11-a | m11-b | mC-aydgv |
| m12-dgv | T7ex5 | m12-a | m12-b | mC-aydgv |
| m13-dgv | T7ex5 | m13-a | m13-b | mC-aydgv |
| m31-dgv | T7ex5 | m31-a | m31-b | mC-aydgv |
| m32-dgv | T7ex5 | m32-a | m32-b | mC-aydgv |
| wt-GS | T7ex5 | wt-a | wt-aydgv | wt-GS |
| m3-GS | T7ex5 | m3-a | m3-b | mT-GS |
| m4-GS | T7ex5 | m4-a | m4-b | wt-GS |
| m5-GS | T7ex5 | m5-a | m5-b | mS-GS |
| m11-GS | T7ex5 | m11-a | m11-b | wt-GS |
| m12-GS | T7ex5 | m12-a | m12-b | wt-GS |
| m13-GS | T7ex5 | m13-a | m13-b | wt-GS |
| m20-GS | T7ex5 | m20-a | m20-b | wt-GS |
| m32-GS | T7ex5 | m32-a | m32-b | wt-GS |
| m3-GG | T7ex5 | m3-a | m3-b | mT-GG |
| m5-GG | T7ex5 | m5-a | m5-b | mCS-GG |
| m11-GG | T7ex5 | m11-a | m11-b | mCS-GG |
| m12-GG | T7ex5 | m12-a | m12-b | mCS-GG |
| m13-GG | T7ex5 | m13-a | m13-b | mCS-GG |
| m32-GG | T7ex5 | m32-a | m32-b | mCS-GG |
| wt-EGS | T7ex5 | wt-a | wt-EGS1 | GS3an2 |
| m11-EGS | T7ex5 | m11-a | wt-EGS1 | GS3an2 |

[4] PatD Enzyme Reaction

After the DNA prepared in 3-2 was transcribed and translated in a cell-free protein expression system of 2.5 µl scale in accordance with the method of Kawakami, et al. (Kawakami et al., Chemistry & Biology 15, 32-42 (2008)) and the solution conditions were adjusted by adding 40 mM Tris-HCl (pH 8.0), 8 mM DTT, 4 mM $MgCl_2$, and 0.8 mM ATP (each, final concentration), recombinant PatD was added.

The reaction was conducted under two conditions as described below.

TABLE 10

| | A | B |
|---|---|---|
| PatD final concentration | 0.6 | 6 |
| Reaction temperature [° C.] | 34 | 25 |
| Reaction time [h] | 2 | 16 |

[5] Mass Spectrometry Analysis of Peptide by Using MALDI-TOF-MS

The mass of the peptide was measured using MALDI-TOF-MS by using sinapinic acid as a matrix and whether a mass change occurred or not by the addition of PatD was checked. The number of azoline rings introduced can be found from the mass change.

Figure 2:
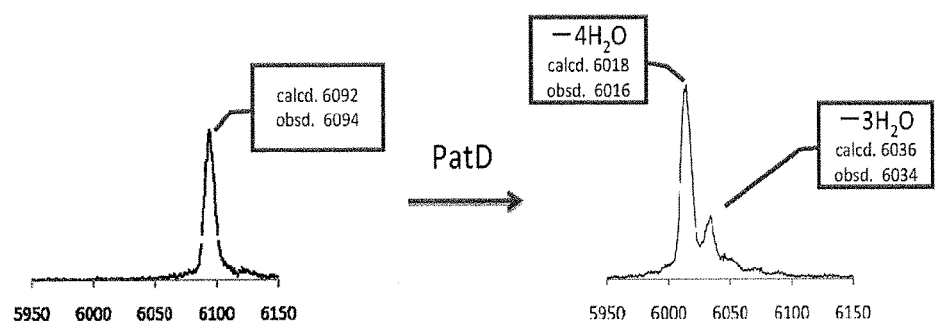
FIG. 2 shows the results of mass spectrometry analysis before and after introduction of an azoline backbone by using PatD into a precursor peptide having the same sequence of a cassette domain as that of natural PatE.

The results of mass spectroscopy at the time when C1wt whose amino acid sequence in the cassette domain was the same as that of wild type PatE was modified with PatD are shown in FIG. 2. As a result, a change in molecular weight showing formation of four azoline rings was observed.

Figure 3:
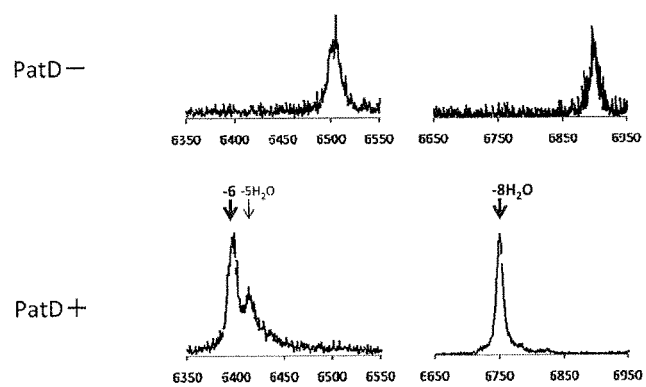
FIG. 3 shows the results of mass spectrometry analysis before and after introduction of an azoline backbone by using PatD into a precursor peptide having a cassette domain composed of 12 amino acids or 16 amino acids. The corresponding sequence numbers of FIG. 3 are:
GLEAS=SEQ ID NO: 3,
AYDGVEPS=SEQ ID NO: 5,
VTACITFCVTIC=SEQ ID NO: 19, and
VCACICFCVCACVCIC=SEQ ID NO: 47.

The results of C1m10 whose cassette domain was composed of 12 amino acids (in the formula (I), n=6) and C1m38 whose cassette domain was composed of 16 amino acids (in the formula (I), n=8) are shown in FIG. 3. It has been confirmed that 6 and 8 azoline rings were introduced into C1m10 and C1m38, respectively.

Figure 4:
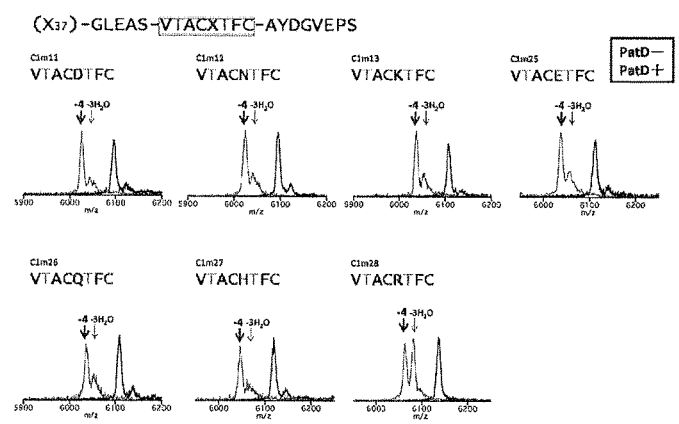
FIG. 4 shows the results of mass spectrometry analysis before and after introduction of an azoline backbone by using PatD into a precursor peptide having, in Xaa1 thereof, a hydrophilic amino acid residue. The corresponding sequence numbers of FIG. 4 are:
GLEAS=SEQ ID NO: 3,
AYDGVEPS=SEQ ID NO: 5,
VTACDTFC=SEQ ID NO: 20,
VTACNTFC=SEQ ID NO: 21,
VTACKTFC=SEQ ID NO: 22,
VTACETFC=SEQ ID NO: 34,
VTACQTFC=SEQ ID NO: 35,
VTACHTFC=SEQ ID NO: 36, and
VTACRTFC=SEQ ID NO: 37.

Other typical results are shown in FIG. 4. As shown in FIG. 4, it has been confirmed that even a sequence having hydrophilic residues in addition to Cys, Ser, or Thr, which has conventionally been considered unsuitable as a substrate of PatD, was modified by PatD.

The substrate tolerance of PatD confirmed based on the results of such a test is shown in FIG. 5. As shown in this figure, a variety of sequences including a sequence which has been considered unsuitable as a substrate of PatD were modified by PatD; and PatD was found to have sufficient substrate tolerance for the synthesis of an azoline compound library.

[6] Glu-C Enzyme Reaction

After the PatD enzyme reaction, 0.5 µg of Glu-C (Roche) was added to 5.0 µl of the reaction solution. The resulting mixture was incubated at 25° C. for 2 hours to cleave the peptide. The mass spectrometry analysis of the modified peptide which had been obtained as a result of such a test and from which the leader sequence had been cleaved are shown in FIG. 6.

[7] Mass Spectroscopy after Glu-C Enzyme Reaction

With α-CHCA as a matrix, the mass of the peptide was measured using MALDI-TOF-MS and formation of a peptide from which the leader sequence had been cleaved was confirmed.

An example of the results is shown in FIG. 6. Formation of a peptide from which the leader sequence has been cleaved has been confirmed.

[8] Synthesis of Library

DNA of PatEpre2 having a non-translation region suited for construction of a library was prepared. The underlined portion is a DNA encoding GLEAS (SEQ ID NO: 3), the recognition sequence 1. The sequence from position 46 to position 151 of SEQ ID NO: 61 is a code region of the leader sequence.

(SEQ ID NO: 61)
TAATACGACTCACTATAGGGTTAACTTTAAGAAGGAGATATACATATGA

ACAAGAAAAACATCCTGCCCCAACAAGGTCAACCGGTTATCCGCTTAAC

CGCAGGACAGTTGAGCTCGCAACTCGCCGAACTGTCTGAAGAAGCACTG

GGCG<u>ACGCGGGGTTGGAGGCAAGC</u>

With PatEpre2 as a template, two libraries as described below were constructed by conducting PCR twice or three times by using a primer containing a random base sequence.

[8-1] (XC)$_n$ Library

A double-stranded DNA having the following sequence was prepared. (n=3 to 8)

(SEQ ID NO: 62)
TAATACGACTCACTATAGGGTTAACTTTAAGAAGGAGATATACATATGA

ACAAGAAAAACATCCTGCCCCAACAAGGTCAACCGGTTATCCGCTTAAC

CGCAGGACAGTTGAGCTCGCAACTCGCCGAACTGTCTGAAGAAGCACTG

GGCGACGCGGGGTTGGAGGCAAGC(NNKTGT)nGCGTACGATGGCGTTG

GT

Translation of this DNA results in synthesis of the following peptide:

(SEQ ID NO: 63)
MNKKNILPQQGQPVIRLTAGQLSSQLAELSEEALGDAGLEAS(XC)$_n$AY

DGVGSGSGS

[8-2] (X—C/S/T)$_n$ Library

A double-stranded DNA having the following sequence was prepared. (n=3 to 6)

(SEQ ID NO: 64)
TAATACGACTCACTATAGGGTTAACTTTAAGAAGGAGATATACATATGA

ACAAGAAAAACATCCTGCCCCAACAAGGTCAACCGGTTATCCGCTTAAC

CGCAGGACAGTTGAGCTCGCAACTCGCCGAACTGTCTGAAGAAGCACTG

GGCGACGCGGGGTTGGAGGCAAGC(NNKWST)nGCGTACGATGGCGTTG

GT

Translation of this DNA results in synthesis of the following peptide.

(SEQ ID NO: 65)
MNKKNILPQQGQPVIRLTAGQLSSQLAELSEEALGDAGLEA (XC/S/T)nAYDGVGSGSGS

The primers used for the construction of individual libraries are shown below. The sequences of the primers are shown in the primer list shown below.

TABLE 11

| library | F primer | 1st R primer | 2nd R primer |
|---------|----------|--------------|--------------|
| XC3 | T7g10M | XC3pool | PatEpool.ex |
| XC4 | T7g10M | XC4pool | PatEpool.ex |
| XC5 | T7g10M | XC5pool | PatEpool.ex |
| XC6 | T7g10M | XC6pool | PatEpool.ex |
| XC7 | T7g10M | XC7pool | PatEpool.ex |
| XC8 | T7g10M | XC8pool | PatEpool.ex |
| XCST3 | T7g10M | XCST3pool | PatEpool.ex |
| XCST4 | T7g10M | XCST4pool | PatEpool.ex |
| XCST5 | T7g10M | XCST5pool | PatEpool.ex |
| XCST6 | T7g10M | XCST6pool | PatEpool.ex |

[9] Study on Leader Sequence (1)

Tests were conducted in a similar manner to that described above in [1] to [8] in order to study the necessity of a leader sequence: by removing a leader sequence from a substrate peptide; by adding a leader sequence obtained by translational synthesis as a peptide separate from a substrate peptide and adding it to a reaction system; or by adding a leader sequence obtained by chemical synthesis to give a final concentration of 1 uM, 10 uM, or 50 uM. The cassette sequence was comprised of 8 amino acids (VTACITFC (SEQ ID NO:

The results are shown in FIG. 7. It has been found that the leader sequence is not essential for the substrate of an enzyme because although a modification efficiency with the enzyme increases when the leader sequence has been fused to a substrate peptide, the substrate peptide was 1-fold dehydrated even without the leader sequence. As long as the leader sequence is present in the reaction system, the substrate peptide is completely (4-fold) dehydrated even if it has not been fused to the substrate peptide, from which it has been confirmed that the substrate peptide is modified sufficiently. This suggests that the leader sequence is not necessary for the substrate specificity but the structure of the leader sequence contributes to the activation of an enzyme and has an influence on the reaction efficiency.

[10] Study on Leader Sequence (2)

In a similar manner to that employed above in [1] to [8], a portion of a leader sequence was deleted as shown in FIG. 8 and FIG. 19 and enzyme activity by PatD was confirmed.

As shown in FIG. 8 and FIG. 19, it has been found that the entire length of the leader sequence is not essential for modification of a substrate peptide with PatD. It has also been confirmed that the C-terminus part of the leader sequence is important for the modification with PatD and a substrate peptide having, for example, about 6 amino acids is subjected to sufficient modification by PatD if it contains the C-terminal of the leader sequence.

[11] Study on Leader Sequence (3)

In a similar manner to that described above in [1] to [8], the entirety of the leader sequence was substituted with a completely different peptide sequence as shown in FIG. 18 and enzyme activity by PatD was studied.

As shown in FIG. 18, it has been confirmed that a leader sequence necessary for modification of a substrate with PatD is not limited to the leader sequence of PatE, but, for example, a partial sequence of human actin, the leader sequence of the precursor peptide of Lacticin 481, or a sequence obtained by shuffling the leader sequence of PatE can also lead to efficient modification by PatD.

[12] Study on Leader Sequence (4)

In a similar manner to that employed above in [1] to [8], the enzyme activity by PatD was confirmed by introducing point mutation into some amino acids of the leader sequence as shown in FIG. 20.

As shown in FIG. 20, it has been confirmed that the 28th Glu, 29th Leu, 31st Glu, 32nd Glu, and 34th Leu of the leader sequence of PatE are important for modification with PatD.

[13] Study on Recognition Sequence

In a similar manner to that employed above in [1] to [8], enzyme activity by PatD was studied by deleting a recognition sequence, by changing the sequence, or by adding another sequence as shown in FIG. 9 or FIG. 21.

As shown in FIG. 9 or FIG. 21, the substrate peptide was completely (4-fold) dehydrated even if it had no recognition sequence 2. When the recognition sequence 1 was removed, dehydration reaction involved the loss of only two water molecules. It has been confirmed that the recognition sequence 1 is also not essential for enzyme activity. Further, even when the recognition sequence was replaced by GGGGG (SEQ ID NO: 173), QQQQQ (SEQ ID NO: 174), LLLLL (SEQ ID NO: 175), or PPPPP (SEQ ID NO: 176), the peptide was sufficiently modified (dehydration of 4 molecules). Also when GGGGG (SEQ ID NO: 173) was inserted between the leader sequence and the recognition sequence, the peptide was sufficiently modified (4-fold and 5-fold dehydration was observed). Even when an additional sequence was placed downstream of the recognition sequence 2, the resulting peptide was subjected to sufficient modification.

unsuitable as a substrate of PatD such as isomer of Thr, substituted Ser, and a diamino acid are modified by PatD and converted into corresponding azoline ring backbones.

[15] Study on Another Substrate

Substrates having the following sequences were synthesized, respectively and modification with PatD was confirmed. The results are shown in the following table. Typical results are shown in FIG. 16 and FIG. 17.

TABLE 11-2

| Leader sequences | Recognition sequence 1 | Cassette sequence | Recognition Sequence 2 | Dehydrated molecules |
|---|---|---|---|---|
| fMNKKNILPQQGQPVIRLTAGQLSSQLAELSEEALGDA | GLEAS | LCGCTSYCYTVS | AYDGVGSGSGS | 2 to 4 |
| fMNKKNILPQQGQPVIRLTAGQLSSQLAELSEEALGDA | GLEAS | SCNSISMSSTPS | AYDGVGSGSGS | 3 to 5 |
| fMNKKNILPQQGQPVIRLTAGQLSSQLAELSEEALGDA | GLEAS | CTLSNTPSSTLT | AYDGVGSGSGS | 3 to 5 |
| fMNKKNILPQQGQPVIRLTAGQLSSQLAELSEEALGDA | GLEAS | LSLSNTFTESES | AYDGVGSGSGS | 1 to 3 |
| fMNKKNILPQQGQPVIRLTAGQLSSQLAELSEEALGDA | GLEAS | SSLCITPSSTQT | AYDGVGSGSGS | 2 to 5 |
| fMNKKNILPQQGQPVIRLTAGQLSSQLAELSEEALGDA | GLEAS | LCGCTSYCYTVS | AYDGV | 2 |
| fMNKKNILPQQGQPVIRLTAGQLSSQLAELSEEALGDA | GLEAS | SCNSISMSSTPS | AYDGV | 2 to 4 |
| fMNKKNILPQQGQPVIRLTAGQLSSQLAELSEEALGDA | GLEAS | SSLCITPSSTQT | AYDGV | 2 to 4 |
| fMNKKNILPQQGQPVIRLTAGQLSSQLAELSEEALGDA | GLEAS | VXAX (X=iPrSer) | AYDGVEPS | 1 or 2 |
| fMNKKNILPQQGQPVIRLTAGQLSSQLAELSEEALGDA | GLEAS | VXAX (X=PhSer) | AYDGVEPS | 1 or 2 |
| fMNKKNILPQQGQPVIRLTAGQLSSQLAELSEEALGDA | GLEAS | VXAXIXFX (X=iPrSer) | AYDGVEPS | 1 to 4 |
| fMNKKNILPQQGQPVIRLTAGQLSSQLAELSEEALGDA | GLEAS | VXAXIXFX (X=PhSer) | AYDGVEPS | 1 to 4 |
| fMLAELSEEALGDA | GLEAS | VXAX (X=Dap) | A | 1 or 2 |
| fMLAELSEEALGDA | GLEAS | VXAX (X=PhSer) | A | 1 or 2 |
| fMLAELSEEALGDA | GGGGG | VXAX (X=Dap) | A | 1 |
| fMLAELSEEALGDA | GGGGG | VXAX (X=PhSer) | A | 1 |
| fMNKKNILPQQGQPVIRLTAGQLSSQLAELSEEALGDA | GLEAS | VXAX (X=Dap) | AYDGVEPS | 2 |
| fMNKKNILPQQGQPVIRLTAGQLSSQLAELSEEALGDA | GLEAS | VXAXIXFX (X=Dap) | AYDGVEPS | 3 or 4 |
| Ac-LAELSEEALGDA | GLEAS | VXAXIXFX (X=Dap) | A | 3 or 4 |
| Ac-LAELSEEALGDA | GGGGG | VXAXIXFX (X=Dap) | A | 4 |

These results have suggested that the modification efficiency with PatD becomes higher when the recognition sequence 1 is present, but no particular limitation is imposed on its sequence and the presence or absence of the recognition sequence 2 has almost no influence on the modification efficiency with PatD. They have also suggested that the addition of a sequence to the downstream of the recognition sequence 2 has almost no influence on the modification efficiency.

[14] Study on Modification Efficiency, with PatD, of a Substrate Having, in the Cassette Sequence Thereof, a Non-Natural Amino Acid As shown in FIG. 10A, a substrate having, in the cassette sequence thereof, a non-natural amino acid was prepared by ribosomal synthesis and the resulting substrate was modified by PatD. Amino acids used are shown in FIG. 10B. Typical results are shown in FIG. 11. As shown in FIG. 11, it has been confirmed that substances conventionally considered The corresponding sequence numbers of Table 11-2 from top to bottom are SEQ ID NOS: 204-223, respectively.

[16] Screening Using mRNA Display Method

Compounds that bound to matrix metalloproteinase (MMP) 12 were screened in accordance with an mRNA display method by using the azoline compound library obtained using the above-mentioned method.

[16-1] Purification of MMP12

MMP12 was expressed in *Escherichia coli* as a construct having, at the C-terminus thereof, a 6×His tag and an Avi tag. Purification was conducted by making use of the His tag.

Since the Avi tag was biotinylated with BirA expressed by birA incorporated in the same plasmid, it was added for immobilization of MMP12 with streptavidin beads upon mRNA display.

[16-2] Construction of mRNA Library

The DNA library obtained in [8] was transcribed using T7 RNA polymerase to obtain an mRNA corresponding to the library.

[16-3] mRNA Display

A cycle from "Ligation with puromycin linker" to "amplification of sequence information of peptide thus recovered" described below was repeated and peptides binding to MMP12 were selected from the azoline-containing compound library.

[16-3-1] Ligation with Puromycin Linker

The puromycin linker represented by the below-described sequence was annealed with the above-mentioned mRNA library and ligated to each other via a T4 RNA ligase. (SPC18 represents PEG having C and O in the total number of 18)

```
                                         (SEQ ID NO: 224)
pdCTCCCGCCCCCCGTCC(SPC18)5CC(Pu)
```

[16-3-2] Translation

The mRNA library to which the puromycin linker had been ligated was translated and a peptide library was synthesized. Puromycin reacts to the C-terminus of the peptide thus synthesized, by which the mRNA and the peptide are connected to each other.

[16-3-3] Modification by PatD

The peptide library tagged with mRNA was subjected to post-translational modification with PatD to introduce azoline rings in the cassette sequence.

[16-3-4] Reverse Transcription

The mRNA bound to the peptide was reverse transcribed and (azoline-modified peptide)-mRNA-DNA complexes were synthesized.

[16-3-5] Cleavage by Protease Glu-C

Glu-C was added and the leader sequence was cleaved.

[16-3-6] Selection of Azoline-Modified Peptide that Binds to MMP12

MMP12 immobilized onto streptavidin beads was mixed with the azoline-containing compound library prepared above and the mixture was incubated at 4° C. for 30 minutes. The supernatant was removed and the residual beads were washed with a buffer. A PCR solution was added to the beads, the mixture was heated at 95° C. for 5 minutes, the peptide was eluted from the beads, and the supernatant was recovered.

[16-3-7] Amplification of Sequence Information of Azoline-Modified Peptide Thus Recovered The DNA contained in the (azoline-modified peptide)-mRNA-DNA complex which had bound to MMP12 and been recovered was amplified by PCR. The DNA thus obtained was transcribed into a corresponding mRNA.

[16-3-8] Identification of the Sequence of Azoline-Containing Compound Selected

The above-mentioned series of operations was repeated. When a change in the recovery ratio of DNA stopped, TA cloning was conducted using the amplified DNA and the sequence of the resulting azoline-containing compound was identified.

[16-3-9] Evaluation of Binding Ability of Azoline-Containing Compound Selected

A series of operations was conducted by using not mRNA from the mRNA library but mRNA of the selected peptide in accordance with a scheme of mRNA display and whether the selected azoline-containing compound binds to MMP12-immobilised beads was studied. In addition, such operations were conducted under the condition wherein post-translational modification with PatD is performed or the condition wherein the modification is not performed. The results have suggested that the sequences thus obtained bind to MMP12 when they have been modified with PatD and that, in these sequences, the azoline backbone contributes to binding to MMP12.

The outline of the mRNA display method is shown in FIG. 12.

The results of selection are shown in FIG. 13.

The sequences of five azoline-containing compounds A to E selected based on the results of selection were analyzed (not including data) and evaluation results of the binding ability to MMP12 are shown in FIG. 14.

A list of base sequences of the primers used is shown below.

TABLE 12

| primer | Base sequence | SEQ ID No: |
|---|---|---|
| T7ex5 | GGCGTAATACGACTCACTATAG | 66 |
| wt-a | ATCGTACGCACAAAACGTGATACACGCCGTAACGCTTGCCTCCAACCCC | 67 |
| wt-b | CGAAGCTTAAGATGGCTCAACGCCATCGTACGCACAAAACGTG | 68 |
| m1-a | CGCCATCGTACGCCGTGATACACGCCGTAACGCTTGCCTCCAACCCC | 69 |
| m1-b | CGAAGCTTAAGATGGCTCAACGCCATCGTACGCCGTG | 70 |
| m2-a | CGCGGTAACACAAAACGTGATACACGCCGTAACGCTTGCCTCCAACCCC | 71 |
| m2-b | CGAAGCTTAAGATGGCTCAACGCCATCGTACGCGGTAACACAAAACGTG | 72 |
| m3-a | ATCGTACGCGGTAAACGTGATGGTCGCCGTAACGCTTGCCTCCAACCCC | 73 |
| m3-b | CGAAGCTTAAGATGGCTCAACGCCATCGTACGCGGTAAACGTG | 74 |
| m4-a | TCGTACGCACAAAACAGATACACGCACAAACGCTTGCCTCCAACCCC | 75 |
| m4-b | CGAAGCTTAAGATGGCTCAACGCCATCGTACGCACAAAACAGATAC | 76 |
| m5-a | ATCGTACGCAGAAAAAGAGATAGACGCAGAAACGCTTGCCTCCAACCCC | 77 |

TABLE 12 -continued

| primer | Base sequence | SEQ ID No: |
|---|---|---|
| m5-b | CGAAGCTTAAGATGGCTCAACGCCATCGTACGCAGAAAAAGAGATAG | 78 |
| m6-a | ATCGTACGCACAAAACGTGATGTCCGCCGTAACGCTTGCCTCCAACCCC | 79 |
| m7-a | ATCGTACGCACAAAACGTGATATTCGCCGTAACGCTTGCCTCCAACCCC | 80 |
| m8-a | ATCGTACGCACAAAACGTGATCTTCGCCGTAACGCTTGCCTCCAACCCC | 81 |
| m9-a | ATCGTACGCAACGGTTGCACAAATGGTAAAACAGCTTGCCTCCAACCCC | 82 |
| m9-b | CGAAGCTTAAGATGGCTCAACGCCATCGTACGCAACGGTTGC | 83 |
| m10-a | AACACAAAACGTGATACACGCCGTAACGCTTGCCTCCAACCCC | 84 |
| m10-b | TCAACGCCATCGTACGCACAAATGGTAACACAAAACGTGATACACGC | 85 |
| m10-c | CGAAGCTTAAGATGGCTCAACGCCATCGTACGC | 86 |
| m11-a | ATCGTACGCACAAAACGTGTCACACGCCGTAACGCTTGCCTCCAACCCC | 87 |
| m12-a | ATCGTACGCACAAAACGTGTTACACGCCGTAACGCTTGCCTCCAACCCC | 88 |
| m13-a | CGTACGCACAAAACGTCTTACACGCCGTAACGCTTGCCTCCAACCCC | 89 |
| m13-b | CGAAGCTTAAGATGGCTCAACGCCATCGTACGCACAAAACGTCTTAC | 90 |
| m14-a | ATCGTACGCACAAAAACAGTCACACGCACAAACGCTTGCCTCCAACCCC | 91 |
| m14-b | CGAAGCTTAAGATGGTCAACGCCATCGTACGCACAAAAACAGTC | 92 |
| m15-a | CGTACGCACAAAAACAATTACACGCACAAACGCTTGCCTCCAACCCC | 93 |
| m15-b | CGAAGCTTAAGATGGCTCAACGCCATCGTACGCACAAAAACAATTACAC | 94 |
| m16-a | TCGTACGCACAAAAACACTTACACGCACAAACGCTTGCCTCCAACCCC | 95 |
| m16-b | CGAAGCTTAAGATGGCTCAACGCCATCGTACGCACAAAAACACTTAC | 96 |
| m17-a | ATCGTACGCGGTAAACGTGATGGTCGCACAAACGCTTGCCTCCAACCCC | 97 |
| m18-a | ATCGTACGCGGTAAACGTGATACACGCCGTAACGCTTGCCTCCAACCCC | 98 |
| m19-a | CGTACGCGGTAAAACAGATGGTCGCCGTAACGCTTGCCTCCAACCCC | 99 |
| m19-b | CGAAGCTTAAGATGGCTCAACGCCATCGTACGCGGTAAAACAGATG | 100 |
| m20-a | ATCGTACGCACAAAACGTGATGGTCGCCGTAACGCTTGCCTCCAACCCC | 101 |
| m21-a | CGTACGCAACACATGCACAAATACAAAAACAGCTTGCCTCCAACCCC | 102 |
| m21-b | CGAAGCTTAAGATGGCTCAACGCCATCGTACGCAACACATGCAC | 103 |
| m22-a | ATCGTACGCACAAAACGTGATACACGCCGTGTCGCTTGCCTCCAACCCC | 104 |
| m23-a | ATCGTACGCACAAAACGTGATACACGCCGTATTGCTTGCCTCCAACCCC | 105 |
| m24-a | ATCGTACGCACAAAACGTGATACACGCCGTCTTGCTTGCCTCCAACCCC | 106 |
| m25-a | GTACGCACAAAACGTTTCACACGCCGTAACGCTTGCCTCCAACCCC | 107 |
| m25-b | CGAAGCTTAAGATGGCTCAACGCCATCGTACGCACAAAACGTTTCAC | 108 |
| m26-a | GTACGCACAAAACGTTTGACACGCCGTAACGCTTGCCTCCAACCCC | 109 |
| m26-b | CGAAGCTTAAGATGGCTCAACGCCATCGTACGCACAAAACGTTTGAC | 110 |

TABLE 13

| | | |
|---|---|---|
| m27-a | ATCGTACGCACAAAACGTGTGACACGCCGTAACGCTTGCCTCCAACCCC | 111 |
| m28-a | ATCGTACGCACAAAACGTGCGACACGCCGTAACGCTTGCCTCCAACCCC | 112 |
| m29-a | GTACGCACAAAACGTCGGACACGCCGTAACGCTTGCCTCCAACCCC | 113 |
| m29-b | CGAAGCTTAAGATGGCTCAACGCCATCGTACGCACAAAACGTCGG | 114 |
| m30-a | ATCGTACGCACAAAACATGATCAGCGCAAAAACGCTTGCCTCCAACCCC | 115 |
| m30-b | CGAAGCTTAAGATGGCTCAACGCCATCGTACGCACAAAACATGATC | 116 |
| m31-a | CGTACGCACAACACATGATCAGCGCAAAAACGCTTGCCTCCAACCCC | 117 |
| m31-b | CGAAGCTTAAGATGGCTCAACGCCATCGTACGCACAACACATGATC | 118 |
| m32-a | CGTACGCACAACAACAGATCAGCGCAAAAACGCTTGCCTCCAACCCC | 119 |
| m32-b | CGAAGCTTAAGATGGCTCAACGCCATCGTACGCACAACAACAGATC | 120 |
| m33-a | ATCGTACGCACAAAAACAACGACACGCACAAACGCTTGCCTCCAACCCC | 121 |
| m33-b | CGAAGCTTAAGATGGCTCAACGCCATCGTACGCACAAAAACAACG | 122 |
| m34-a | ATCGTACGCACAAAACGTGATACACGCCGTACGGCTTGCCTCCAACCCC | 123 |
| m35-a | CGTACGCACAACAACAACACAGCGCAAAAACGCTTGCCTCCAACCCC | 124 |
| m35-b | CGAAGCTTAAGATGGCTCAACGCCATCGTACGCACAACAACAACAC | 125 |
| m36-a | ATCGTACGCACAACGACAGTCACAGTCACAACGGCTTGCCTCCAACCCC | 126 |
| m36-b | CGAAGCTTAAGATGGCTCAACGCCATCGTACGCACAACGACAG | 127 |
| m37-a | CGCACAAACACAAAACAGATACACGCACAAACGCTTGCCTCCAACCCC | 128 |
| m37-b | TCAACGCCATCGTACGCACAAACACACGCACAAACACAAAACAGAT | 129 |
| m38-b | CGCCATCGTACGCACAGATACAAACACACGCACAAACACAAAAACAGAT | 130 |
| m38-c | CGAAGCTTAAGATGGCTCAACGCCATCGTACGCACAG | 131 |
| m39-a | ATCGTACGCGGTAAACGTGTCGGTCGCCGTAACGCTTGCCTCCAACCCC | 132 |
| m40-a | CGTACGCAGAAAAAGAGTCAGACGCAGAAACGCTTGCCTCCAACCCC | 133 |
| m40-b | CGAAGCTTAAGATGGCTCAACGCCATCGTACGCAGAAAAAGAGTCAG | 134 |
| m41-a | CGGTAAACGTGATGGTCGCCGTAACGCTTGCCTCCAACCCC | 135 |
| m41-b | TCAACGCCATCGTACGCGGTAATGGTAACGGTAAACGTGATGGTCG | 136 |
| m42-a | CGCACAAACACAAAAACAGATACAACGACAACGGCTTGCCTCCAACCCC | 137 |
| m43-a | CACAACGACAACGACAGATACACGCACAAACGCTTGCCTCCAACCCC | 138 |
| m43-b | TCAACGCCATCGTACGCACAAACACACGCACAACGACAACGACAGATAC | 139 |
| m44-a | CGGCAAACGCAAAAGCAGATACACGCACAAACGCTTGCCTCCAACCCC | 140 |
| m44-b | TCAACGCCATCGTACGCACAACGACAACGGCAAACGCAAAAGCAG | 141 |
| m45-a | ATCGTACGCACAAAAGCAGATGGTCGCCGTAACGCTTGCCTCCAACCCC | 142 |
| m45-b | CGAAGCTTAAGATGGCTCAACGCCATCGTACGCACAAAAGCAG | 143 |
| m46-a | ATCGTACGCACAAAACGTGATGGTCGCACAAACGCTTGCCTCCAACCCC | 144 |
| m47-a | ATCGTACGCGGTAAACGTGATACACGCACAAACGCTTGCCTCCAACCCC | 145 |
| m48-a | CGTACGCGGTAAAACAGATGGTCGCACAAACGCTTGCCTCCAACCCC | 146 |
| pre-lon a | GGGTTAACTTTAACAAGGAGAAAAACATGAACAAGAAAAACATCCTGCC | 147 |
| pre-lon b | GGCGTAATACGACTCACTATAGGGTTAACTTTAACAAGGAGAAAAAC | 148 |
| pre-lon c | GCTTGCCTCCAACCCC | 149 |
| wt-aydgv | CGAAGCTTAAACGCCATCGTACGCACAAAACGTGATAC | 150 |

TABLE 13-continued

| | | SEQ ID NO: |
|---|---|---|
| mC-aydgv | CGAAGCTTAAACGCCATCGTACGCAC | 151 |
| mT-aydgv | CGAAGCTTAAACGCCATCGTACGCG | 152 |
| mS-aydgv | CGAAGCTTAAACGCCATCGTACGCAG | 153 |
| wt-GS | CGAAGCTTAGCTGCCGCTGCCGCTGCCAACGCCATCGTACGCAC | 154 |
| mT-GS | CGAAGCTTAGCTGCCGCTGCCGCTGCCAACGCCATCGTACGCG | 155 |
| mS-GS | CGAAGCTTAGCTGCCGCTGCCGCTGCCAACGCCATCGTACGCAG | 156 |
| mT-GG | CGAAGCTTACCCGCCCCCGCCCCCGCCAACGCCATCGTACGCG | 157 |
| mCS-GG | CGAAGCTTACCCGCCCCCGCCCCCGCCAACGCCATCGTACGCA | 158 |

TABLE 13-2

| primer | Base sequence | SEQ ID NO: |
|---|---|---|
| m49 | TCAACGCCATCGTACGCACAAACGCTTGCCTCCAACCCC | |
| m50 | TCAACGCCATCGTACGCACATGCACAAACGCTTGCCTCCAACCCC | |
| m51-a | ACAATAACAAATGCAAACACATGCACAAACGCAGAAGCAGATACATGCACAAACGCTTGCCTCCAACCCC | |
| m51-b | CGAAGCTTAAGATGGCTCAACGCCATCGTACGCACAAATACAAAAACAATAACAAATGCAAACACATGC | |
| m52-a | CACAGTAGCAAAAACACACAAACGCAGAAGCAGATACATGCACAAACGCTTGCCTCCAACCCC | |
| m52-b | ACAATAACAAATGCAAACACATGCACAAAAACAAATACAGTAGCAAGCACAGTAGCAAAAACACACAC | |
| m53-a | CGTACGCGGTACGGGTGTCGGTGTCGGTACGGCTTGCCTCCAACCCC | |
| m53-b | CGAAGCTTAAGATGGCTCAACGCCATCGTACGCGGTACGGG | |
| m54-a | ATCGTACGCAGAACGAGAGTCAGAGTCAGAACGGCTTGCCTCCAACCCC | |
| m54-b | CGAAGCTTAAGATGGCTCAACGCCATCGTACGCAGAACGAGAG | |
| m55 | GTACGCGCAACAACAGCAGCAACAGCTTGCCTCCAACCCC | |
| m56 | GCCATCGTACGCCGTGGTGGTCGTCGTGGTGCTTGCCTCCAACCCC | |
| m57-c | CATCGTACGCAGATGATGAAGAAGATGAGCTTGCCTCCAACCCC | |
| m57-d | CGAAGCTTAAGATGGCTCAACGCCATCGTACGCAGATGATGAAG | |
| m58 | ATCGTACGCGGTAAACGTGATGGTCGCAAAAACGCTTGCCTCCAACCCC | |
| m59 | ATCGTACGCGGTAAACGTGATGGTCGCAAAACAGCTTGCCTCCAACCCC | |
| m68 | TCAACGCCATCGTACGCGCAACAACAGCATAACGCAAAACGCTTGCCTCCAACCCC | |
| n119 | TCAACGCCATCGTACGCGGTAACGCTTGCCTCCAACCCC | |
| m196 | TCAACGCCATCGTACGCACACGCCGTAACGCTTGCCTCCAACCCC | |
| m197 | TCAACGCCATCGTACGCACACGCCGTAACACAAAACGTGATACACGCCGTAACGCTTGCCTCCAACCCC | |
| m198-a | GCCGTAACACAAAACGTGATACACGCCGTAACGCTTGCCTCCAACCCC | |
| m198-b | TCAACGCCATCGTACGCACAAATAGAAACACACGCCGTAACACAAAACGTG | |
| m199-a | TGTAACAAATAGAAACACACGCCGTAACACAAAACGTGATACACGCCGTAACGCTTGCCTCCAACCCC | |
| m199-b | TCAACGCCATCGTACGCGGTAATACAGAAGGTGTAACAAATAGAAACACACGC | |

TABLE 13-3

| | |
|---|---|
| m200-a | AAGAAATACAAACGGTTGCACAAAAGGTAATACAGAAGGTGTAACAAATAGAAACACACGC |
| m200-b | TCAACGCCATCGTACGCACAAATGGTGAAACAGTAAGAAATACAAACGGTTGCAC |
| m201 | TCAACGCCATCGTACGCACAAATGGTAACACACGCCGTAACACAAAACGTG |
| m202-a | TGTAACAAATGGTAACACACGCCGTAACACAAAACGTGATACACGCCGTAACGCTTGCCTCCAACCCC |
| m2027b | TCAACGCCATCGTACGCGGTAATACAGAAGGTGTAACAAATGGTAACACACG |
| m203-a | AAGTAATACAAACGGTTGCACAAAAGGTAATACAGAAGGTGTAACAAATGGTAACACACG |
| m203-b | TCAACGCCATCGTACGCACAAATGGTGAAACAGTAAGTAATACAAACGGTTGCAC |
| m35-N-b | CGAAGCTTAAGATGGCTCAACGCCATCGTACGCGCAACAACAGC |

The corresponding sequence numbers of Table 13-3 from top to bottom are SEQ ID NOS: 225-256, respectively.

TABLE 14

| | | |
|---|---|---|
| wt-EGS1 | CCGCTGCCGCTACCCTCAACGCCATCGTACGCACAAAACGTG | 159 |
| GS3an2 | TTTCCGCCCCCGTCCTAGCTGCCGCTGCCGCTACC | 160 |
| T7g10M | TAATACGACTCACTATAGGGTTAACTTTAAGAAGGAGATATACATATG | 161 |
| XC3pool | ACCAACGCCATCGTACGCACAMNNACAMNNACAMNNGCTTGCCTCCAACCCCG | 162 |
| XC4pool | ACCAACGCCATCGTACGCACAMNNACAMNNACAMNNACAMNNGCTTGCCTCCAACCCCG | 163 |
| XC5pool | ACCAACGCCATCGTACGCACAMNNACAMNNACAMNNACAMNNACAMNNG CTTGCCTCCAACCCCG | 164 |
| XC6pool | ACCAACGCCATCGTACGCACAMNNACAMNNACAMNNACAMNNACAMNNACAMNNGCTTGCCTCCAACCCCG | 165 |
| XC7pool | ACCAACGCCATCGTACGCACAMNNACAMNNACAMNNACAMNNACAMNNACAMNNACAMNNGCTTGCCTCCAACCCCG | 166 |
| XC8pool | ACCAACGCCATCGTACGCACAMNNACAMNNACAMNNACAMNNACAMNNACAMNNACAMNNGCTTGCCTCCAACCCCG | 167 |
| XCST3pool | ACCAACGCCATCGTACGCASWMNNASWMNNASWMNNGCTTGCCTCCAACCCCG | 168 |
| XCST4pool | ACCAACGCCATCGTACGCASWMNNASWMNNASWMNNASWMNNGCTTGCCTCCAACCCCG | 169 |
| XCST5pool | ACCAACGCCATCGTACGCASWMNNASWMNNASWMNNASWMNNASWMNNGCTTGCCTCCAACCCCG | 170 |
| XCST6pool | ACCAACGCCATCGTACGCASWMNNASWMNNASWMNNASWMNNASWMNNASWMNNGCTTGCCTCCAACCCCG | 171 |
| PatEpool.ex | TTTCCGCCCCCGTCCTAGCTGCCGCTGCCGCTACCAACGCCATCGTACGC | 172 |

Sequence Listing Free Text

SEQ ID NO: 1 represents the amino acid sequence of the leader sequence of PatE.

SEQ ID NOS: 2 and 3 are examples of the recognition sequence 1 by an azoline backbone-introducing enzyme, respectively.

SEQ ID NOS: 4 to 9 are examples of the recognition sequence 2 by an azoline backbone-introducing enzyme, respectively.

SEQ ID NOS: 10-57 are amino acid sequences confirmed newly to become a substrate of an azoline backbone-introducing enzyme.

SEQ ID NO: 58 is the base sequence of a nucleic acid encoding PatE.

SEQ ID NO: 59 is the base sequence of a nucleic acid encoding PatEpre.

SEQ ID NO: 60 is the amino acid sequence of the cassette domain of wild type PatE.

SEQ ID NO: 61 is the base sequence of a nucleic acid encoding PatEpre2.

SEQ ID NO: 62 is the base sequence of a nucleic acid encoding the peptide portion of each compound of $(XC)_n$ library.

SEQ ID NO: 63 is an amino acid sequence of the peptide portion of each compound of $(XC)_n$ library.

SEQ ID NO: 64 is the base sequence of a nucleic acid encoding the peptide portion of each compound of $(X-C/S/T)_n$ library.

SEQ ID NO: 65 is the amino acid sequence of the peptide portion of each compound of $(X-C/S/T)_n$ library.

SEQ ID NOS: 66 to 172 are the base sequences of primers used in Examples of the present application.

SEQUENCE LISTING

```
<160> NUMBER OF SEQ ID NOS: 376

<210> SEQ ID NO 1
<211> LENGTH: 37
<212> TYPE: PRT
<213> ORGANISM: Prochloron didemni

<400> SEQUENCE: 1

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala
        35

<210> SEQ ID NO 2
<211> LENGTH: 5
<212> TYPE: PRT
<213> ORGANISM: Artificial Sequence
<220> FEATURE:
<223> OTHER INFORMATION: An example of Recognition Sequence 1 based on
      Prochloron didemni.
<220> FEATURE:
<221> NAME/KEY: MISC_FEATURE
<222> LOCATION: (2)..(2)
<223> OTHER INFORMATION: Xaa stands for Ala, Leu or Val.
<220> FEATURE:
<221> NAME/KEY: MISC_FEATURE
<222> LOCATION: (3)..(3)
<223> OTHER INFORMATION: Xaa stands for Gly, Glu or Asp.
<220> FEATURE:
<221> NAME/KEY: MISC_FEATURE
<222> LOCATION: (4)..(4)
<223> OTHER INFORMATION: Xaa stands for Ala or Pro.
<220> FEATURE:
<221> NAME/KEY: MISC_FEATURE
<222> LOCATION: (5)..(5)
<223> OTHER INFORMATION: Xaa stands for Ser, Thr or Cys.

<400> SEQUENCE: 2

Gly Xaa Xaa Xaa Xaa
1               5

<210> SEQ ID NO 3
<211> LENGTH: 5
<212> TYPE: PRT
<213> ORGANISM: Artificial Sequence
<220> FEATURE:
<223> OTHER INFORMATION: An example of Recognition Sequence 1 based on
      Prochloron didemni.

<400> SEQUENCE: 3

Gly Leu Glu Ala Ser
1               5
```

-continued

```
<210> SEQ ID NO 4
<211> LENGTH: 5
<212> TYPE: PRT
<213> ORGANISM: Artificial Sequence
<220> FEATURE:
<223> OTHER INFORMATION: An example of Recognition Sequence 2 based on
      Prochloron didemni.
<220> FEATURE:
<221> NAME/KEY: MISC_FEATURE
<222> LOCATION: (1)..(1)
<223> OTHER INFORMATION: Xaa stands for Ala or Ser.
<220> FEATURE:
<221> NAME/KEY: MISC_FEATURE
<222> LOCATION: (3)..(3)
<223> OTHER INFORMATION: Xaa stands for Asp or Glu.
<220> FEATURE:
<221> NAME/KEY: MISC_FEATURE
<222> LOCATION: (5)..(5)
<223> OTHER INFORMATION: Xaa stands for Ala, Leu or Val.

<400> SEQUENCE: 4

Xaa Tyr Xaa Gly Xaa
1               5

<210> SEQ ID NO 5
<211> LENGTH: 8
<212> TYPE: PRT
<213> ORGANISM: Artificial Sequence
<220> FEATURE:
<223> OTHER INFORMATION: An example of Recognition Sequence 2 based on
      Prochloron didemni.

<400> SEQUENCE: 5

Ala Tyr Asp Gly Val Glu Pro Ser
1               5

<210> SEQ ID NO 6
<211> LENGTH: 5
<212> TYPE: PRT
<213> ORGANISM: Artificial Sequence
<220> FEATURE:
<223> OTHER INFORMATION: An example of Recognition Sequence 2 based on
      Prochloron didemni.

<400> SEQUENCE: 6

Ala Tyr Asp Gly Val
1               5

<210> SEQ ID NO 7
<211> LENGTH: 11
<212> TYPE: PRT
<213> ORGANISM: Artificial Sequence
<220> FEATURE:
<223> OTHER INFORMATION: An example of Recognition Sequence 2 based on
      Prochloron didemni.

<400> SEQUENCE: 7

Ala Tyr Asp Gly Val Gly Ser Gly Ser Gly Ser
1               5                   10

<210> SEQ ID NO 8
<211> LENGTH: 11
<212> TYPE: PRT
<213> ORGANISM: Artificial Sequence
<220> FEATURE:
<223> OTHER INFORMATION: An example of Recognition Sequence 2 based on
      Prochloron didemni.
```

```
<400> SEQUENCE: 8

Ala Tyr Asp Gly Val Gly Gly Gly Gly Gly
1               5                   10

<210> SEQ ID NO 9
<211> LENGTH: 12
<212> TYPE: PRT
<213> ORGANISM: Artificial Sequence
<220> FEATURE:
<223> OTHER INFORMATION: An example of Recognition Sequence 2 based on
      Prochloron didemni.
<400> SEQUENCE: 9

Ala Tyr Asp Gly Val Glu Gly Ser Gly Ser Gly Ser
1               5                   10

<210> SEQ ID NO 10
<211> LENGTH: 6
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 10

Val Thr Ala Cys Ile Thr
1               5

<210> SEQ ID NO 11
<211> LENGTH: 10
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 11

Val Thr Ala Cys Ile Thr Phe Cys Val Thr
1               5                   10

<210> SEQ ID NO 12
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 12

Val Thr Ala Thr Ile Thr Phe Thr
1               5

<210> SEQ ID NO 13
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 13

Val Cys Ala Cys Ile Cys Phe Cys
1               5
```

```
<210> SEQ ID NO 14
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 14

Val Ser Ala Ser Ile Ser Phe Ser
1               5

<210> SEQ ID NO 15
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 15

Val Thr Ala Asp Ile Thr Phe Cys
1               5

<210> SEQ ID NO 16
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 16

Val Thr Ala Asn Ile Thr Phe Cys
1               5

<210> SEQ ID NO 17
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 17

Val Thr Ala Lys Ile Thr Phe Cys
1               5

<210> SEQ ID NO 18
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 18

Cys Phe Thr Ile Cys Ala Thr Val
1               5

<210> SEQ ID NO 19
<211> LENGTH: 12
<212> TYPE: PRT
<213> ORGANISM: Artificial Sequence
```

```
<220> FEATURE:
<223> OTHER INFORMATION: An example of newly identified substrate
      sequence of azoline ring introducing enzyme based on Prochloron
      didemni.

<400> SEQUENCE: 19

Val Thr Ala Cys Ile Thr Phe Cys Val Thr Ile Cys
1               5                   10

<210> SEQ ID NO 20
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 20

Val Thr Ala Cys Asp Thr Phe Cys
1               5

<210> SEQ ID NO 21
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 21

Val Thr Ala Cys Asn Thr Phe Cys
1               5

<210> SEQ ID NO 22
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 22

Val Thr Ala Cys Lys Thr Phe Cys
1               5

<210> SEQ ID NO 23
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 23

Val Cys Ala Cys Asp Cys Phe Cys
1               5

<210> SEQ ID NO 24
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.
```

```
<400> SEQUENCE: 24

Val Cys Ala Cys Asn Cys Phe Cys
1               5

<210> SEQ ID NO 25
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 25

Val Cys Ala Cys Lys Cys Phe Cys
1               5

<210> SEQ ID NO 26
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 26

Val Cys Ala Thr Ile Thr Phe Thr
1               5

<210> SEQ ID NO 27
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 27

Val Thr Ala Cys Ile Thr Phe Thr
1               5

<210> SEQ ID NO 28
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 28

Val Thr Ala Thr Ile Cys Phe Thr
1               5

<210> SEQ ID NO 29
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 29

Val Thr Ala Thr Ile Thr Phe Cys
```

-continued

```
1               5

<210> SEQ ID NO 30
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 30

Cys Phe Cys Ile Cys Ala Cys Val
1               5

<210> SEQ ID NO 31
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 31

Asp Thr Ala Cys Ile Thr Phe Cys
1               5

<210> SEQ ID NO 32
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 32

Asn Thr Ala Cys Ile Thr Phe Cys
1               5

<210> SEQ ID NO 33
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 33

Lys Thr Ala Cys Ile Thr Phe Cys
1               5

<210> SEQ ID NO 34
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 34

Val Thr Ala Cys Glu Thr Phe Cys
1               5

<210> SEQ ID NO 35
```

```
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 35

Val Thr Ala Cys Gln Thr Phe Cys
1               5

<210> SEQ ID NO 36
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 36

Val Thr Ala Cys His Thr Phe Cys
1               5

<210> SEQ ID NO 37
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 37

Val Thr Ala Cys Arg Thr Phe Cys
1               5

<210> SEQ ID NO 38
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 38

Val Thr Ala Cys Pro Thr Phe Cys
1               5

<210> SEQ ID NO 39
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 39

Val Phe Ala Leu Ile Met Phe Cys
1               5

<210> SEQ ID NO 40
<211> LENGTH: 8
<212> TYPE: PRT
<213> ORGANISM: Artificial Sequence
<220> FEATURE:
```

```
<223> OTHER INFORMATION: An example of newly identified substrate
      sequence of azoline ring introducing enzyme based on Prochloron
      didemni.

<400> SEQUENCE: 40

Val Phe Ala Leu Ile Met Cys Cys
1               5

<210> SEQ ID NO 41
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 41

Val Phe Ala Leu Ile Cys Cys Cys
1               5

<210> SEQ ID NO 42
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 42

Val Cys Ala Cys Arg Cys Phe Cys
1               5

<210> SEQ ID NO 43
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 43

Arg Thr Ala Cys Ile Thr Phe Cys
1               5

<210> SEQ ID NO 44
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 44

Val Phe Ala Leu Cys Cys Cys Cys
1               5

<210> SEQ ID NO 45
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.
```

```
<400> SEQUENCE: 45

Arg Cys Asp Cys Asp Cys Arg Cys
1               5

<210> SEQ ID NO 46
<211> LENGTH: 14
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 46

Val Cys Ala Cys Ile Cys Phe Cys Val Cys Ala Cys Val Cys
1               5                   10

<210> SEQ ID NO 47
<211> LENGTH: 16
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 47

Val Cys Ala Cys Ile Cys Phe Cys Val Cys Ala Cys Val Cys Ile Cys
1               5                   10                  15

<210> SEQ ID NO 48
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 48

Val Thr Ala Thr Asp Thr Phe Thr
1               5

<210> SEQ ID NO 49
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 49

Val Ser Ala Ser Asp Ser Phe Ser
1               5

<210> SEQ ID NO 50
<211> LENGTH: 12
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 50

Val Thr Ala Thr Ile Thr Phe Thr Val Thr Ile Thr
1               5                   10
```

<210> SEQ ID NO 51
<211> LENGTH: 14
<212> TYPE: PRT
<213> ORGANISM: Artificial Sequence
<220> FEATURE:
<223> OTHER INFORMATION: An example of newly identified substrate sequence of azoline ring introducing enzyme based on Prochloron didemni.

<400> SEQUENCE: 51

Arg Cys Arg Cys Ile Cys Phe Cys Val Cys Ala Cys Val Cys
1               5                   10

<210> SEQ ID NO 52
<211> LENGTH: 14
<212> TYPE: PRT
<213> ORGANISM: Artificial Sequence
<220> FEATURE:
<223> OTHER INFORMATION: An example of newly identified substrate sequence of azoline ring introducing enzyme based on Prochloron didemni.

<400> SEQUENCE: 52

Val Cys Ala Cys Ile Cys Arg Cys Arg Cys Ala Cys Val Cys
1               5                   10

<210> SEQ ID NO 53
<211> LENGTH: 14
<212> TYPE: PRT
<213> ORGANISM: Artificial Sequence
<220> FEATURE:
<223> OTHER INFORMATION: An example of newly identified substrate sequence of azoline ring introducing enzyme based on Prochloron didemni.

<400> SEQUENCE: 53

Val Cys Ala Cys Ile Cys Phe Cys Val Cys Arg Cys Arg Cys
1               5                   10

<210> SEQ ID NO 54
<211> LENGTH: 8
<212> TYPE: PRT
<213> ORGANISM: Artificial Sequence
<220> FEATURE:
<223> OTHER INFORMATION: An example of newly identified substrate sequence of azoline ring introducing enzyme based on Prochloron didemni.

<400> SEQUENCE: 54

Val Thr Ala Thr Ile Cys Phe Cys
1               5

<210> SEQ ID NO 55
<211> LENGTH: 8
<212> TYPE: PRT
<213> ORGANISM: Artificial Sequence
<220> FEATURE:
<223> OTHER INFORMATION: An example of newly identified substrate sequence of azoline ring introducing enzyme based on Prochloron didemni.

<400> SEQUENCE: 55

Val Cys Ala Thr Ile Thr Phe Cys
1               5

<210> SEQ ID NO 56
<211> LENGTH: 8

```
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 56

Val Cys Ala Cys Ile Thr Phe Thr
1               5

<210> SEQ ID NO 57
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 57

Val Cys Ala Thr Ile Cys Phe Thr
1               5

<210> SEQ ID NO 58
<211> LENGTH: 216
<212> TYPE: PRT
<213> ORGANISM: Prochloron didemni
<220> FEATURE:
<221> NAME/KEY: misc_feature
<223> OTHER INFORMATION: DNA sequence coding PatE
<220> FEATURE:
<221> NAME/KEY: misc_feature
<223> OTHER INFORMATION: DNA sequence encoding PatE

<400> SEQUENCE: 58

Ala Thr Gly Ala Ala Cys Ala Ala Gly Ala Ala Ala Ala Cys Ala
1               5                   10                  15

Thr Cys Cys Thr Gly Cys Cys Cys Ala Ala Cys Ala Ala Gly Gly
                20                  25                  30

Thr Cys Ala Ala Cys Cys Gly Gly Thr Thr Ala Thr Cys Cys Gly Cys
            35                  40                  45

Thr Thr Ala Ala Cys Cys Gly Cys Ala Gly Gly Ala Cys Ala Gly Thr
        50                  55                  60

Thr Gly Ala Gly Cys Thr Cys Cys Ala Ala Cys Thr Cys Gly Cys
65                  70                  75                  80

Cys Gly Ala Ala Cys Thr Gly Thr Cys Thr Gly Ala Ala Gly Ala Ala
                85                  90                  95

Gly Cys Ala Cys Thr Gly Gly Gly Cys Gly Ala Cys Gly Cys Gly Gly
            100                 105                 110

Gly Gly Thr Thr Gly Gly Ala Gly Gly Cys Ala Ala Gly Cys Gly Thr
        115                 120                 125

Thr Ala Cys Gly Gly Cys Gly Thr Gly Thr Ala Thr Cys Ala Cys Gly
    130                 135                 140

Thr Thr Thr Thr Gly Thr Gly Cys Gly Thr Ala Cys Gly Ala Thr Gly
145                 150                 155                 160

Gly Cys Gly Thr Thr Gly Ala Gly Cys Cys Ala Thr Cys Thr Ala Thr
                165                 170                 175

Thr Ala Cys Gly Gly Thr Cys Thr Gly Cys Ala Thr Thr Ala Gly Thr
            180                 185                 190

Gly Thr Cys Thr Gly Cys Gly Cys Cys Thr Ala Thr Gly Ala Thr Gly
        195                 200                 205
```

Gly Gly Gly Ala Gly Thr Ala Ala
    210             215

<210> SEQ ID NO 59
<211> LENGTH: 173
<212> TYPE: DNA
<213> ORGANISM: Artificial Sequence
<220> FEATURE:
<223> OTHER INFORMATION: DNA sequence encoding PatEpre based on
      Prochloron didemni.

<400> SEQUENCE: 59
ggcgtaatac gactcactat agggttaact ttaacaagga gaaaaacatg aacaagaaaa    60
acatcctgcc ccaacaaggt caaccggtta tccgcttaac cgcaggacag ttgagctcgc   120
aactcgccga actgtctgaa gaagcactgg gcgacgcggg gttggaggca agc          173

<210> SEQ ID NO 60
<211> LENGTH: 8
<212> TYPE: PRT
<213> ORGANISM: Prochloron didemni
<220> FEATURE:
<221> NAME/KEY: misc_feature
<223> OTHER INFORMATION: Amino acid sequence of cassette region of
      wild type PatE

<400> SEQUENCE: 60

Val Thr Ala Cys Ile Thr Phe Cys
1               5

<210> SEQ ID NO 61
<211> LENGTH: 171
<212> TYPE: DNA
<213> ORGANISM: Artificial Sequence
<220> FEATURE:
<223> OTHER INFORMATION: DNA sequence encoding PatEpre2 based on
      Prochloron didemni.

<400> SEQUENCE: 61
taatacgact cactataggg ttaactttaa gaaggagata tacatatgaa caagaaaaac    60
atcctgcccc aacaaggtca accggttatc cgcttaaccg caggacagtt gagctcgcaa   120
ctcgccgaac tgtctgaaga agcactgggc gacgcggggt tggaggcaag c            171

<210> SEQ ID NO 62
<211> LENGTH: 195
<212> TYPE: DNA
<213> ORGANISM: Artificial Sequence
<220> FEATURE:
<223> OTHER INFORMATION: DNA sequence encoding (XC)n Library based on
      Prochloron didemni.
<220> FEATURE:
<221> NAME/KEY: misc_feature
<222> LOCATION: (172)..(173)
<223> OTHER INFORMATION: n stands for any base.
<220> FEATURE:
<221> NAME/KEY: misc_feature
<222> LOCATION: (174)..(174)
<223> OTHER INFORMATION: n stands for G or T.
<220> FEATURE:
<221> NAME/KEY: misc_feature
<222> LOCATION: (172)..(177)
<223> OTHER INFORMATION: This sequence may be repeated 1 to 20 times.

<400> SEQUENCE: 62
taatacgact cactataggg ttaactttaa gaaggagata tacatatgaa caagaaaaac    60
atcctgcccc aacaaggtca accggttatc cgcttaaccg caggacagtt gagctcgcaa   120
ctcgccgaac tgtctgaaga agcactgggc gacgcggggt tggaggcaag cnnntgtgcg    180
tacgatggcg ttggt                                                     195

<210> SEQ ID NO 63
<211> LENGTH: 55
<212> TYPE: PRT
<213> ORGANISM: Artificial Sequence
<220> FEATURE:
<223> OTHER INFORMATION: Amino Acid Sequence of (XC)n Library based on
      Prochloron didemni.
<220> FEATURE:
<221> NAME/KEY: MISC_FEATURE
<222> LOCATION: (43)..(43)
<223> OTHER INFORMATION: Xaa stands for any amino acid.
<220> FEATURE:
<221> NAME/KEY: MISC_FEATURE
<222> LOCATION: (43)..(44)
<223> OTHER INFORMATION: This sequence may be repeated 1 to 20 times.

<400> SEQUENCE: 63

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Xaa Cys Ala Tyr Asp Gly
        35                  40                  45

Val Gly Ser Gly Ser Gly Ser
    50                  55

<210> SEQ ID NO 64
<211> LENGTH: 195
<212> TYPE: DNA
<213> ORGANISM: Artificial Sequence
<220> FEATURE:
<223> OTHER INFORMATION: DNA sequence encoding (X-C/S/T)n Library based
      on Prochloron didemni.
<220> FEATURE:
<221> NAME/KEY: misc_feature
<222> LOCATION: (172)..(173)
<223> OTHER INFORMATION: n stands for any base.
<220> FEATURE:
<221> NAME/KEY: misc_feature
<222> LOCATION: (174)..(174)
<223> OTHER INFORMATION: n stands for G or T.
<220> FEATURE:
<221> NAME/KEY: misc_feature
<222> LOCATION: (175)..(175)
<223> OTHER INFORMATION: n stands for A or T.
<220> FEATURE:
<221> NAME/KEY: misc_feature
<222> LOCATION: (176)..(176)
<223> OTHER INFORMATION: n stands for C or G.
<220> FEATURE:
<221> NAME/KEY: misc_feature
<222> LOCATION: (172)..(177)
<223> OTHER INFORMATION: This sequence may be repeated 1 to 20 times.

<400> SEQUENCE: 64
taatacgact cactataggg ttaactttaa gaaggagata tacatatgaa caagaaaaac    60
atcctgcccc aacaaggtca accggttatc cgcttaaccg caggacagtt gagctcgcaa   120
ctcgccgaac tgtctgaaga agcactgggc gacgcggggt tggaggcaag cnnnnntgcg   180
tacgatggcg ttggt                                                    195

<210> SEQ ID NO 65
<211> LENGTH: 54
<212> TYPE: PRT

```
<213> ORGANISM: Artificial Sequence
<220> FEATURE:
<223> OTHER INFORMATION: Amino acid sequence of (X-C/S/T)n Library
      based on Prochloron didemni.
<220> FEATURE:
<221> NAME/KEY: MISC_FEATURE
<222> LOCATION: (42)..(42)
<223> OTHER INFORMATION: Xaa stands for any amino acid.
<220> FEATURE:
<221> NAME/KEY: MISC_FEATURE
<222> LOCATION: (43)..(43)
<223> OTHER INFORMATION: Xaa stands for Cys, Ser or Thr.
<220> FEATURE:
<221> NAME/KEY: MISC_FEATURE
<222> LOCATION: (42)..(43)
<223> OTHER INFORMATION: This sequence may be repeated 1 to 20 times.

<400> SEQUENCE: 65

Met Asn Lys Lys Asn Ile Leu Pro Gln Gln Gly Gln Pro Val Ile Arg
 1               5                  10                  15

Leu Thr Ala Gly Gln Leu Ser Ser Gln Leu Ala Glu Leu Ser Glu Glu
             20                  25                  30

Ala Leu Gly Asp Ala Gly Leu Glu Ala Xaa Xaa Ala Tyr Asp Gly Val
         35                  40                  45

Gly Ser Gly Ser Gly Ser
         50

<210> SEQ ID NO 66
<211> LENGTH: 22
<212> TYPE: DNA
<213> ORGANISM: Artificial Sequence
<220> FEATURE:
<223> OTHER INFORMATION: DNA sequence of primer T7ex5 based on
      Prochloron didemni.

<400> SEQUENCE: 66
ggcgtaatac gactcactat ag                                           22

<210> SEQ ID NO 67
<211> LENGTH: 49
<212> TYPE: DNA
<213> ORGANISM: Artificial Sequence
<220> FEATURE:
<223> OTHER INFORMATION: DNA sequence of primer wt-a based on
      Prochloron didemni.

<400> SEQUENCE: 67
atcgtacgca caaaacgtga tacacgccgt aacgcttgcc tccaacccc              49

<210> SEQ ID NO 68
<211> LENGTH: 43
<212> TYPE: DNA
<213> ORGANISM: Artificial Sequence
<220> FEATURE:
<223> OTHER INFORMATION: DNA sequence of primer wt-b based on
      Prochloron didemni.

<400> SEQUENCE: 68
cgaagcttaa gatggctcaa cgccatcgta cgcacaaaac gtg                    43

<210> SEQ ID NO 69
<211> LENGTH: 47
<212> TYPE: DNA
<213> ORGANISM: Artificial Sequence
<220> FEATURE:
<223> OTHER INFORMATION: DNA sequence of primer m1-a based on
      Prochloron didemni.
```

```
<400> SEQUENCE: 69
cgccatcgta cgccgtgata cacgccgtaa cgcttgcctc caacccc                47

<210> SEQ ID NO 70
<211> LENGTH: 37
<212> TYPE: DNA
<213> ORGANISM: Artificial Sequence
<220> FEATURE:
<223> OTHER INFORMATION: DNA sequence of primer m1-b based on
      Prochloron didemni.

<400> SEQUENCE: 70
cgaagcttaa gatggctcaa cgccatcgta cgccgtg                           37

<210> SEQ ID NO 71
<211> LENGTH: 49
<212> TYPE: DNA
<213> ORGANISM: Artificial Sequence
<220> FEATURE:
<223> OTHER INFORMATION: DNA sequence of primer m2-a based on
      Prochloron didemni.

<400> SEQUENCE: 71
cgcggtaaca caaaacgtga tacacgccgt aacgcttgcc tccaacccc              49

<210> SEQ ID NO 72
<211> LENGTH: 49
<212> TYPE: DNA
<213> ORGANISM: Artificial Sequence
<220> FEATURE:
<223> OTHER INFORMATION: DNA sequence of primer m2-b based on
      Prochloron didemni.

<400> SEQUENCE: 72
cgaagcttaa gatggctcaa cgccatcgta cgcggtaaca caaaacgtg              49

<210> SEQ ID NO 73
<211> LENGTH: 49
<212> TYPE: DNA
<213> ORGANISM: Artificial Sequence
<220> FEATURE:
<223> OTHER INFORMATION: DNA sequence of primer m3-a based on
      Prochloron didemni.

<400> SEQUENCE: 73
atcgtacgcg gtaaacgtga tggtcgccgt aacgcttgcc tccaacccc              49

<210> SEQ ID NO 74
<211> LENGTH: 43
<212> TYPE: DNA
<213> ORGANISM: Artificial Sequence
<220> FEATURE:
<223> OTHER INFORMATION: DNA sequence of primer m3-b based on
      Prochloron didemni.

<400> SEQUENCE: 74
cgaagcttaa gatggctcaa cgccatcgta cgcggtaaac gtg                    43

<210> SEQ ID NO 75
<211> LENGTH: 48
<212> TYPE: DNA
<213> ORGANISM: Artificial Sequence
<220> FEATURE:
<223> OTHER INFORMATION: DNA sequence of primer m4-a based on
      Prochloron didemni.

<400> SEQUENCE: 75
```
tcgtacgcac aaaaacagat acacgcacaa acgcttgcct ccaacccc        48

<210> SEQ ID NO 76
<211> LENGTH: 47
<212> TYPE: DNA
<213> ORGANISM: Artificial Sequence
<220> FEATURE:
<223> OTHER INFORMATION: DNA sequence of primer m4-b based on
      Prochloron didemni.

<400> SEQUENCE: 76
cgaagcttaa gatggctcaa cgccatcgta cgcacaaaaa cagatac          47

<210> SEQ ID NO 77
<211> LENGTH: 49
<212> TYPE: DNA
<213> ORGANISM: Artificial Sequence
<220> FEATURE:
<223> OTHER INFORMATION: DNA sequence of primer m5-a based on
      Prochloron didemni.

<400> SEQUENCE: 77
atcgtacgca gaaaaagaga tagacgcaga aacgcttgcc tccaacccc        49

<210> SEQ ID NO 78
<211> LENGTH: 47
<212> TYPE: DNA
<213> ORGANISM: Artificial Sequence
<220> FEATURE:
<223> OTHER INFORMATION: DNA sequence of primer m5-b based on
      Prochloron didemni.

<400> SEQUENCE: 78
cgaagcttaa gatggctcaa cgccatcgta cgcagaaaaa gagatag          47

<210> SEQ ID NO 79
<211> LENGTH: 49
<212> TYPE: DNA
<213> ORGANISM: Artificial Sequence
<220> FEATURE:
<223> OTHER INFORMATION: DNA sequence of primer m6-a based on
      Prochloron didemni.

<400> SEQUENCE: 79
atcgtacgca caaaacgtga tgtccgccgt aacgcttgcc tccaacccc        49

<210> SEQ ID NO 80
<211> LENGTH: 49
<212> TYPE: DNA
<213> ORGANISM: Artificial Sequence
<220> FEATURE:
<223> OTHER INFORMATION: DNA sequence of primer m7-a based on
      Prochloron didemni.

<400> SEQUENCE: 80
atcgtacgca caaaacgtga tattcgccgt aacgcttgcc tccaacccc        49

<210> SEQ ID NO 81
<211> LENGTH: 49
<212> TYPE: DNA
<213> ORGANISM: Artificial Sequence
<220> FEATURE:
<223> OTHER INFORMATION: DNA sequence of primer m8-a based on
      Prochloron didemni.

<400> SEQUENCE: 81
atcgtacgca caaaacgtga tcttcgccgt aacgcttgcc tccaacccc        49

<210> SEQ ID NO 82
<211> LENGTH: 49
<212> TYPE: DNA
<213> ORGANISM: Artificial Sequence
<220> FEATURE:
<223> OTHER INFORMATION: DNA sequence of primer m9-a based on
      Prochloron didemni.

<400> SEQUENCE: 82
atcgtacgca acggttgcac aaatggtaaa acagcttgcc tccaacccc        49

<210> SEQ ID NO 83
<211> LENGTH: 42
<212> TYPE: DNA
<213> ORGANISM: Artificial Sequence
<220> FEATURE:
<223> OTHER INFORMATION: DNA sequence of primer m9-b based on
      Prochloron didemni.

<400> SEQUENCE: 83
cgaagcttaa gatggctcaa cgccatcgta cgcaacggtt gc               42

<210> SEQ ID NO 84
<211> LENGTH: 43
<212> TYPE: DNA
<213> ORGANISM: Artificial Sequence
<220> FEATURE:
<223> OTHER INFORMATION: DNA sequence of primer m10-a based on
      Prochloron didemni.

<400> SEQUENCE: 84
aacacaaaac gtgatacacg ccgtaacgct tgcctccaac ccc              43

<210> SEQ ID NO 85
<211> LENGTH: 47
<212> TYPE: DNA
<213> ORGANISM: Artificial Sequence
<220> FEATURE:
<223> OTHER INFORMATION: DNA sequence of primer m10-b based on
      Prochloron didemni.

<400> SEQUENCE: 85
tcaacgccat cgtacgcaca aatggtaaca caaaacgtga tacacgc          47

<210> SEQ ID NO 86
<211> LENGTH: 33
<212> TYPE: DNA
<213> ORGANISM: Artificial Sequence
<220> FEATURE:
<223> OTHER INFORMATION: DNA sequence of primer m10-c based on
      Prochloron didemni.

<400> SEQUENCE: 86
cgaagcttaa gatggctcaa cgccatcgta cgc                         33

<210> SEQ ID NO 87
<211> LENGTH: 49
<212> TYPE: DNA
<213> ORGANISM: Artificial Sequence
<220> FEATURE:
<223> OTHER INFORMATION: DNA sequence of primer m11-a based on
      Prochloron didemni.

<400> SEQUENCE: 87
atcgtacgca caaaacgtgt cacacgccgt aacgcttgcc tccaacccc        49

```
<210> SEQ ID NO 88
<211> LENGTH: 49
<212> TYPE: DNA
<213> ORGANISM: Artificial Sequence
<220> FEATURE:
<223> OTHER INFORMATION: DNA sequence of primer m12-a based on
      Prochloron didemni.

<400> SEQUENCE: 88
atcgtacgca caaaacgtgt tacacgccgt aacgcttgcc tccaacccc              49

<210> SEQ ID NO 89
<211> LENGTH: 47
<212> TYPE: DNA
<213> ORGANISM: Artificial Sequence
<220> FEATURE:
<223> OTHER INFORMATION: DNA sequence of primer m13-a based on
      Prochloron didemni.

<400> SEQUENCE: 89
cgtacgcaca aaacgtctta cacgccgtaa cgcttgcctc caacccc                47

<210> SEQ ID NO 90
<211> LENGTH: 47
<212> TYPE: DNA
<213> ORGANISM: Artificial Sequence
<220> FEATURE:
<223> OTHER INFORMATION: DNA sequence of primer m13-b based on
      Prochloron didemni.

<400> SEQUENCE: 90
cgaagcttaa gatggctcaa cgccatcgta cgcacaaaac gtcttac                47

<210> SEQ ID NO 91
<211> LENGTH: 49
<212> TYPE: DNA
<213> ORGANISM: Artificial Sequence
<220> FEATURE:
<223> OTHER INFORMATION: DNA sequence of primer m14-a based on
      Prochloron didemni.

<400> SEQUENCE: 91
atcgtacgca caaaaacagt cacacgcaca aacgcttgcc tccaacccc              49

<210> SEQ ID NO 92
<211> LENGTH: 45
<212> TYPE: DNA
<213> ORGANISM: Artificial Sequence
<220> FEATURE:
<223> OTHER INFORMATION: DNA sequence of primer m14-b based on
      Prochloron didemni.

<400> SEQUENCE: 92
cgaagcttaa gatggctcaa cgccatcgta cgcacaaaaa cagtc                  45

<210> SEQ ID NO 93
<211> LENGTH: 47
<212> TYPE: DNA
<213> ORGANISM: Artificial Sequence
<220> FEATURE:
<223> OTHER INFORMATION: DNA sequence of primer m15-a based on
      Prochloron didemni.

<400> SEQUENCE: 93
cgtacgcaca aaacaatta cacgcacaaa cgcttgcctc caacccc                 47
```

<210> SEQ ID NO 94
<211> LENGTH: 49
<212> TYPE: DNA
<213> ORGANISM: Artificial Sequence
<220> FEATURE:
<223> OTHER INFORMATION: DNA sequence of primer m15-b based on
      Prochloron didemni.

<400> SEQUENCE: 94
cgaagcttaa gatggctcaa cgccatcgta cgcacaaaaa caattacac           49

<210> SEQ ID NO 95
<211> LENGTH: 48
<212> TYPE: DNA
<213> ORGANISM: Artificial Sequence
<220> FEATURE:
<223> OTHER INFORMATION: DNA sequence of primer m16-a based on
      Prochloron didemni.

<400> SEQUENCE: 95
tcgtacgcac aaaaacactt acacgcacaa acgcttgcct ccaacccc            48

<210> SEQ ID NO 96
<211> LENGTH: 47
<212> TYPE: DNA
<213> ORGANISM: Artificial Sequence
<220> FEATURE:
<223> OTHER INFORMATION: DNA sequence of primer m16-b based on
      Prochloron didemni.

<400> SEQUENCE: 96
cgaagcttaa gatggctcaa cgccatcgta cgcacaaaaa cacttac             47

<210> SEQ ID NO 97
<211> LENGTH: 49
<212> TYPE: DNA
<213> ORGANISM: Artificial Sequence
<220> FEATURE:
<223> OTHER INFORMATION: DNA sequence of primer m17-a based on
      Prochloron didemni.

<400> SEQUENCE: 97
atcgtacgcg gtaaacgtga tggtcgcaca aacgcttgcc tccaacccc           49

<210> SEQ ID NO 98
<211> LENGTH: 49
<212> TYPE: DNA
<213> ORGANISM: Artificial Sequence
<220> FEATURE:
<223> OTHER INFORMATION: DNA sequence of primer m18-a based on
      Prochloron didemni.

<400> SEQUENCE: 98
atcgtacgcg gtaaacgtga tacacgccgt aacgcttgcc tccaacccc           49

<210> SEQ ID NO 99
<211> LENGTH: 47
<212> TYPE: DNA
<213> ORGANISM: Artificial Sequence
<220> FEATURE:
<223> OTHER INFORMATION: DNA sequence of primer m19-a based on
      Prochloron didemni.

<400> SEQUENCE: 99
cgtacgcggt aaaacagatg gtcgccgtaa cgcttgcctc caacccc             47

```
<210> SEQ ID NO 100
<211> LENGTH: 46
<212> TYPE: DNA
<213> ORGANISM: Artificial Sequence
<220> FEATURE:
<223> OTHER INFORMATION: DNA sequence of primer m19-b based on
      Prochloron didemni.

<400> SEQUENCE: 100
cgaagcttaa gatggctcaa cgccatcgta cgcggtaaaa cagatg           46

<210> SEQ ID NO 101
<211> LENGTH: 49
<212> TYPE: DNA
<213> ORGANISM: Artificial Sequence
<220> FEATURE:
<223> OTHER INFORMATION: DNA sequence of primer m20-a based on
      Prochloron didemni.

<400> SEQUENCE: 101
atcgtacgca caaaacgtga tggtcgccgt aacgcttgcc tccaacccc        49

<210> SEQ ID NO 102
<211> LENGTH: 47
<212> TYPE: DNA
<213> ORGANISM: Artificial Sequence
<220> FEATURE:
<223> OTHER INFORMATION: DNA sequence of primer m21-a based on
      Prochloron didemni.

<400> SEQUENCE: 102
cgtacgcaac acatgcacaa atacaaaaac agcttgcctc caacccc          47

<210> SEQ ID NO 103
<211> LENGTH: 44
<212> TYPE: DNA
<213> ORGANISM: Artificial Sequence
<220> FEATURE:
<223> OTHER INFORMATION: DNA sequence of primer m21-b based on
      Prochloron didemni.

<400> SEQUENCE: 103
cgaagcttaa gatggctcaa cgccatcgta cgcaacacat gcac             44

<210> SEQ ID NO 104
<211> LENGTH: 49
<212> TYPE: DNA
<213> ORGANISM: Artificial Sequence
<220> FEATURE:
<223> OTHER INFORMATION: DNA sequence of primer m22-a based on
      Prochloron didemni.

<400> SEQUENCE: 104
atcgtacgca caaaacgtga tacacgccgt gtcgcttgcc tccaacccc        49

<210> SEQ ID NO 105
<211> LENGTH: 49
<212> TYPE: DNA
<213> ORGANISM: Artificial Sequence
<220> FEATURE:
<223> OTHER INFORMATION: DNA sequence of primer m23-a based on
      Prochloron didemni.

<400> SEQUENCE: 105
atcgtacgca caaaacgtga tacacgccgt attgcttgcc tccaacccc        49

<210> SEQ ID NO 106
```

```
<210> SEQ ID NO 106
<211> LENGTH: 49
<212> TYPE: DNA
<213> ORGANISM: Artificial Sequence
<220> FEATURE:
<223> OTHER INFORMATION: DNA sequence of primer m24-a based on
      Prochloron didemni.

<400> SEQUENCE: 106
atcgtacgca caaaacgtga tacacgccgt cttgcttgcc tccaacccc         49

<210> SEQ ID NO 107
<211> LENGTH: 46
<212> TYPE: DNA
<213> ORGANISM: Artificial Sequence
<220> FEATURE:
<223> OTHER INFORMATION: DNA sequence of primer m25-a based on
      Prochloron didemni.

<400> SEQUENCE: 107
gtacgcacaa aacgtttcac acgccgtaac gcttgcctcc aacccc            46

<210> SEQ ID NO 108
<211> LENGTH: 47
<212> TYPE: DNA
<213> ORGANISM: Artificial Sequence
<220> FEATURE:
<223> OTHER INFORMATION: DNA sequence of primer m25-b based on
      Prochloron didemni.

<400> SEQUENCE: 108
cgaagcttaa gatggctcaa cgccatcgta cgcacaaaac gtttcac           47

<210> SEQ ID NO 109
<211> LENGTH: 46
<212> TYPE: DNA
<213> ORGANISM: Artificial Sequence
<220> FEATURE:
<223> OTHER INFORMATION: DNA sequence of primer m26-a based on
      Prochloron didemni.

<400> SEQUENCE: 109
gtacgcacaa aacgtttgac acgccgtaac gcttgcctcc aacccc            46

<210> SEQ ID NO 110
<211> LENGTH: 47
<212> TYPE: DNA
<213> ORGANISM: Artificial Sequence
<220> FEATURE:
<223> OTHER INFORMATION: DNA sequence of primer m26-b based on
      Prochloron didemni.

<400> SEQUENCE: 110
cgaagcttaa gatggctcaa cgccatcgta cgcacaaaac gtttgac           47

<210> SEQ ID NO 111
<211> LENGTH: 49
<212> TYPE: DNA
<213> ORGANISM: Artificial Sequence
<220> FEATURE:
<223> OTHER INFORMATION: DNA sequence of primer m27-a based on
      Prochloron didemni.

<400> SEQUENCE: 111
atcgtacgca caaaacgtgt gacacgccgt aacgcttgcc tccaacccc         49

<210> SEQ ID NO 112
<211> LENGTH: 49
```

<212> TYPE: DNA
<213> ORGANISM: Artificial Sequence
<220> FEATURE:
<223> OTHER INFORMATION: DNA sequence of primer m28-a based on
      Prochloron didemni.

<400> SEQUENCE: 112
atcgtacgca caaaacgtgc gacacgccgt aacgcttgcc tccaacccc                49

<210> SEQ ID NO 113
<211> LENGTH: 46
<212> TYPE: DNA
<213> ORGANISM: Artificial Sequence
<220> FEATURE:
<223> OTHER INFORMATION: DNA sequence of primer m29-a based on
      Prochloron didemni.

<400> SEQUENCE: 113
gtacgcacaa aacgtcggac acgccgtaac gcttgcctcc aacccc                   46

<210> SEQ ID NO 114
<211> LENGTH: 45
<212> TYPE: DNA
<213> ORGANISM: Artificial Sequence
<220> FEATURE:
<223> OTHER INFORMATION: DNA sequence of primer m29-b based on
      Prochloron didemni.

<400> SEQUENCE: 114
cgaagcttaa gatggctcaa cgccatcgta cgcacaaaac gtcgg                    45

<210> SEQ ID NO 115
<211> LENGTH: 49
<212> TYPE: DNA
<213> ORGANISM: Artificial Sequence
<220> FEATURE:
<223> OTHER INFORMATION: DNA sequence of primer m30-a based on
      Prochloron didemni.

<400> SEQUENCE: 115
atcgtacgca caaaacatga tcagcgcaaa aacgcttgcc tccaacccc                49

<210> SEQ ID NO 116
<211> LENGTH: 46
<212> TYPE: DNA
<213> ORGANISM: Artificial Sequence
<220> FEATURE:
<223> OTHER INFORMATION: DNA sequence of primer m30-b based on
      Prochloron didemni.

<400> SEQUENCE: 116
cgaagcttaa gatggctcaa cgccatcgta cgcacaaaac atgatc                   46

<210> SEQ ID NO 117
<211> LENGTH: 47
<212> TYPE: DNA
<213> ORGANISM: Artificial Sequence
<220> FEATURE:
<223> OTHER INFORMATION: DNA sequence of primer m31-a based on
      Prochloron didemni.

<400> SEQUENCE: 117
cgtacgcaca acacatgatc agcgcaaaaa cgcttgcctc caacccc                  47

<210> SEQ ID NO 118
<211> LENGTH: 46
<212> TYPE: DNA

```
<213> ORGANISM: Artificial Sequence
<220> FEATURE:
<223> OTHER INFORMATION: DNA sequence of primer m31-b based on
      Prochloron didemni.

<400> SEQUENCE: 118
cgaagcttaa gatggctcaa cgccatcgta cgcacaacac atgatc            46

<210> SEQ ID NO 119
<211> LENGTH: 47
<212> TYPE: DNA
<213> ORGANISM: Artificial Sequence
<220> FEATURE:
<223> OTHER INFORMATION: DNA sequence of primer m32-a based on
      Prochloron didemni.

<400> SEQUENCE: 119
cgtacgcaca acaacagatc agcgcaaaaa cgcttgcctc caacccc           47

<210> SEQ ID NO 120
<211> LENGTH: 46
<212> TYPE: DNA
<213> ORGANISM: Artificial Sequence
<220> FEATURE:
<223> OTHER INFORMATION: DNA sequence of primer m32-b based on
      Prochloron didemni.

<400> SEQUENCE: 120
cgaagcttaa gatggctcaa cgccatcgta cgcacaacaa cagatc            46

<210> SEQ ID NO 121
<211> LENGTH: 49
<212> TYPE: DNA
<213> ORGANISM: Artificial Sequence
<220> FEATURE:
<223> OTHER INFORMATION: DNA sequence of primer m33-a based on
      Prochloron didemni.

<400> SEQUENCE: 121
atcgtacgca caaaacaac gacacgcaca aacgcttgcc tccaacccc           49

<210> SEQ ID NO 122
<211> LENGTH: 45
<212> TYPE: DNA
<213> ORGANISM: Artificial Sequence
<220> FEATURE:
<223> OTHER INFORMATION: DNA sequence of primer m33-b based on
      Prochloron didemni.

<400> SEQUENCE: 122
cgaagcttaa gatggctcaa cgccatcgta cgcacaaaaa caacg             45

<210> SEQ ID NO 123
<211> LENGTH: 49
<212> TYPE: DNA
<213> ORGANISM: Artificial Sequence
<220> FEATURE:
<223> OTHER INFORMATION: DNA sequence of primer m34-a based on
      Prochloron didemni.

<400> SEQUENCE: 123
atcgtacgca caaaacgtga tacacgccgt acggcttgcc tccaacccc         49

<210> SEQ ID NO 124
<211> LENGTH: 47
<212> TYPE: DNA
<213> ORGANISM: Artificial Sequence
```

```
<220> FEATURE:
<223> OTHER INFORMATION: DNA sequence of primer m35-a based on
      Prochloron didemni.

<400> SEQUENCE: 124
cgtacgcaca acaacaacac agcgcaaaaa cgcttgcctc caacccc              47

<210> SEQ ID NO 125
<211> LENGTH: 46
<212> TYPE: DNA
<213> ORGANISM: Artificial Sequence
<220> FEATURE:
<223> OTHER INFORMATION: DNA sequence of primer m35-b based on
      Prochloron didemni.

<400> SEQUENCE: 125
cgaagcttaa gatggctcaa cgccatcgta cgcacaacaa caacac              46

<210> SEQ ID NO 126
<211> LENGTH: 49
<212> TYPE: DNA
<213> ORGANISM: Artificial Sequence
<220> FEATURE:
<223> OTHER INFORMATION: DNA sequence of primer m36-a based on
      Prochloron didemni.

<400> SEQUENCE: 126
atcgtacgca caacgacagt cacagtcaca acggcttgcc tccaacccc           49

<210> SEQ ID NO 127
<211> LENGTH: 43
<212> TYPE: DNA
<213> ORGANISM: Artificial Sequence
<220> FEATURE:
<223> OTHER INFORMATION: DNA sequence of primer m36-b based on
      Prochloron didemni.

<400> SEQUENCE: 127
cgaagcttaa gatggctcaa cgccatcgta cgcacaacga cag                 43

<210> SEQ ID NO 128
<211> LENGTH: 49
<212> TYPE: DNA
<213> ORGANISM: Artificial Sequence
<220> FEATURE:
<223> OTHER INFORMATION: DNA sequence of primer m37-a based on
      Prochloron didemni.

<400> SEQUENCE: 128
cgcacaaaca caaaaacaga tacacgcaca aacgcttgcc tccaacccc           49

<210> SEQ ID NO 129
<211> LENGTH: 47
<212> TYPE: DNA
<213> ORGANISM: Artificial Sequence
<220> FEATURE:
<223> OTHER INFORMATION: DNA sequence of primer m37-b based on
      Prochloron didemni.

<400> SEQUENCE: 129
tcaacgccat cgtacgcaca aacacacgca caaacacaaa aacagat             47

<210> SEQ ID NO 130
<211> LENGTH: 49
<212> TYPE: DNA
<213> ORGANISM: Artificial Sequence
<220> FEATURE:
```

<223> OTHER INFORMATION: DNA sequence of primer m38-b based on
      Prochloron didemni.

<400> SEQUENCE: 130
cgccatcgta cgcacagata caaacacacg cacaaacaca aaaacagat                49

<210> SEQ ID NO 131
<211> LENGTH: 37
<212> TYPE: DNA
<213> ORGANISM: Artificial Sequence
<220> FEATURE:
<223> OTHER INFORMATION: DNA sequence of primer m38-c based on
      Prochloron didemni.

<400> SEQUENCE: 131
cgaagcttaa gatggctcaa cgccatcgta cgcacag                             37

<210> SEQ ID NO 132
<211> LENGTH: 49
<212> TYPE: DNA
<213> ORGANISM: Artificial Sequence
<220> FEATURE:
<223> OTHER INFORMATION: DNA sequence of primer m39-a based on
      Prochloron didemni.

<400> SEQUENCE: 132
atcgtacgcg gtaaacgtgt cggtcgccgt aacgcttgcc tccaacccc                49

<210> SEQ ID NO 133
<211> LENGTH: 47
<212> TYPE: DNA
<213> ORGANISM: Artificial Sequence
<220> FEATURE:
<223> OTHER INFORMATION: DNA sequence of primer m40-a based on
      Prochloron didemni.

<400> SEQUENCE: 133
cgtacgcaga aaaagagtca gacgcagaaa cgcttgcctc caacccc                  47

<210> SEQ ID NO 134
<211> LENGTH: 47
<212> TYPE: DNA
<213> ORGANISM: Artificial Sequence
<220> FEATURE:
<223> OTHER INFORMATION: DNA sequence of primer m40-b based on
      Prochloron didemni.

<400> SEQUENCE: 134
cgaagcttaa gatggctcaa cgccatcgta cgcagaaaaa gagtcag                  47

<210> SEQ ID NO 135
<211> LENGTH: 41
<212> TYPE: DNA
<213> ORGANISM: Artificial Sequence
<220> FEATURE:
<223> OTHER INFORMATION: DNA sequence of primer m41-a based on
      Prochloron didemni.

<400> SEQUENCE: 135
cggtaaacgt gatggtcgcc gtaacgcttg cctccaaccc c                        41

<210> SEQ ID NO 136
<211> LENGTH: 46
<212> TYPE: DNA
<213> ORGANISM: Artificial Sequence
<220> FEATURE:
<223> OTHER INFORMATION: DNA sequence of primer m41-b based on Prochloron didemni.

<400> SEQUENCE: 136
tcaacgccat cgtacgcggt aatggtaacg gtaaacgtga tggtcg               46

<210> SEQ ID NO 137
<211> LENGTH: 49
<212> TYPE: DNA
<213> ORGANISM: Artificial Sequence
<220> FEATURE:
<223> OTHER INFORMATION: DNA sequence of primer m42-a based on
      Prochloron didemni.

<400> SEQUENCE: 137
cgcacaaaca caaaaacaga tacaacgaca acggcttgcc tccaacccc            49

<210> SEQ ID NO 138
<211> LENGTH: 47
<212> TYPE: DNA
<213> ORGANISM: Artificial Sequence
<220> FEATURE:
<223> OTHER INFORMATION: DNA sequence of primer m43-a based on
      Prochloron didemni.

<400> SEQUENCE: 138
cacaacgaca acgacagata cacgcacaaa cgcttgcctc caacccc              47

<210> SEQ ID NO 139
<211> LENGTH: 49
<212> TYPE: DNA
<213> ORGANISM: Artificial Sequence
<220> FEATURE:
<223> OTHER INFORMATION: DNA sequence of primer m44-b based on
      Prochloron didemni.

<400> SEQUENCE: 139
tcaacgccat cgtacgcaca aacacacgca caacgacaac gacagatac            49

<210> SEQ ID NO 140
<211> LENGTH: 48
<212> TYPE: DNA
<213> ORGANISM: Artificial Sequence
<220> FEATURE:
<223> OTHER INFORMATION: DNA sequence of primer m44-a based on
      Prochloron didemni.

<400> SEQUENCE: 140
cggcaaacgc aaaagcagat acacgcacaa acgcttgcct ccaacccc             48

<210> SEQ ID NO 141
<211> LENGTH: 45
<212> TYPE: DNA
<213> ORGANISM: Artificial Sequence
<220> FEATURE:
<223> OTHER INFORMATION: DNA sequence of primer m44-b based on
      Prochloron didemni.

<400> SEQUENCE: 141
tcaacgccat cgtacgcaca acgacaacgg caaacgcaaa agcag                45

<210> SEQ ID NO 142
<211> LENGTH: 49
<212> TYPE: DNA
<213> ORGANISM: Artificial Sequence
<220> FEATURE:
<223> OTHER INFORMATION: DNA sequence of primer m45-a based on
      Prochloron didemni.

<400> SEQUENCE: 142
atcgtacgca caaaagcaga tggtcgccgt aacgcttgcc tccaacccc                49

<210> SEQ ID NO 143
<211> LENGTH: 43
<212> TYPE: DNA
<213> ORGANISM: Artificial Sequence
<220> FEATURE:
<223> OTHER INFORMATION: DNA sequence of primer m45-b based on
      Prochloron didemni.

<400> SEQUENCE: 143
cgaagcttaa gatggctcaa cgccatcgta cgcacaaaag cag                     43

<210> SEQ ID NO 144
<211> LENGTH: 49
<212> TYPE: DNA
<213> ORGANISM: Artificial Sequence
<220> FEATURE:
<223> OTHER INFORMATION: DNA sequence of primer m46-a based on
      Prochloron didemni.

<400> SEQUENCE: 144
atcgtacgca caaacgtga tggtcgcaca aacgcttgcc tccaacccc                 49

<210> SEQ ID NO 145
<211> LENGTH: 49
<212> TYPE: DNA
<213> ORGANISM: Artificial Sequence
<220> FEATURE:
<223> OTHER INFORMATION: DNA sequence of primer m47-a based on
      Prochloron didemni.

<400> SEQUENCE: 145
atcgtacgcg gtaaacgtga tacacgcaca aacgcttgcc tccaacccc                49

<210> SEQ ID NO 146
<211> LENGTH: 47
<212> TYPE: DNA
<213> ORGANISM: Artificial Sequence
<220> FEATURE:
<223> OTHER INFORMATION: DNA sequence of primer m48-a based on
      Prochloron didemni.

<400> SEQUENCE: 146
cgtacgcggt aaacagatg gtcgcacaaa cgcttgcctc caacccc                   47

<210> SEQ ID NO 147
<211> LENGTH: 49
<212> TYPE: DNA
<213> ORGANISM: Artificial Sequence
<220> FEATURE:
<223> OTHER INFORMATION: DNA sequence of primer pre-lon a based on
      Prochloron didemni.

<400> SEQUENCE: 147
gggttaactt taacaaggag aaaaacatga acaagaaaaa catcctgcc                49

<210> SEQ ID NO 148
<211> LENGTH: 47
<212> TYPE: DNA
<213> ORGANISM: Artificial Sequence
<220> FEATURE:
<223> OTHER INFORMATION: DNA sequence of primer pre-lon b based on
      Prochloron didemni.

<400> SEQUENCE: 148
ggcgtaatac gactcactat agggttaact ttaacaagga gaaaaac                47

<210> SEQ ID NO 149
<211> LENGTH: 16
<212> TYPE: DNA
<213> ORGANISM: Artificial Sequence
<220> FEATURE:
<223> OTHER INFORMATION: DNA sequence of primer pre-lon c based on
      Prochloron didemni.

<400> SEQUENCE: 149
gcttgcctcc aaccccc                                                 16

<210> SEQ ID NO 150
<211> LENGTH: 38
<212> TYPE: DNA
<213> ORGANISM: Artificial Sequence
<220> FEATURE:
<223> OTHER INFORMATION: DNA sequence of primer wt-aydgv based on
      Prochloron didemni.

<400> SEQUENCE: 150
cgaagcttaa acgccatcgt acgcacaaaa cgtgatac                          38

<210> SEQ ID NO 151
<211> LENGTH: 26
<212> TYPE: DNA
<213> ORGANISM: Artificial Sequence
<220> FEATURE:
<223> OTHER INFORMATION: DNA sequence of primer mC-aydgv based on
      Prochloron didemni.

<400> SEQUENCE: 151
cgaagcttaa acgccatcgt acgcac                                       26

<210> SEQ ID NO 152
<211> LENGTH: 25
<212> TYPE: DNA
<213> ORGANISM: Artificial Sequence
<220> FEATURE:
<223> OTHER INFORMATION: DNA sequence of primer mT-aydgv based on
      Prochloron didemni.

<400> SEQUENCE: 152
cgaagcttaa acgccatcgt acgcg                                        25

<210> SEQ ID NO 153
<211> LENGTH: 26
<212> TYPE: DNA
<213> ORGANISM: Artificial Sequence
<220> FEATURE:
<223> OTHER INFORMATION: DNA sequence of primer mS-aydgv based on
      Prochloron didemni.

<400> SEQUENCE: 153
cgaagcttaa acgccatcgt acgcag                                       26

<210> SEQ ID NO 154
<211> LENGTH: 44
<212> TYPE: DNA
<213> ORGANISM: Artificial Sequence
<220> FEATURE:
<223> OTHER INFORMATION: DNA sequence of primer wt-GS based on
      Prochloron didemni.

<400> SEQUENCE: 154
cgaagcttag ctgccgctgc cgctgccaac gccatcgtac gcac    44

<210> SEQ ID NO 155
<211> LENGTH: 43
<212> TYPE: DNA
<213> ORGANISM: Artificial Sequence
<220> FEATURE:
<223> OTHER INFORMATION: DNA sequence of primer mT-GS based on
      Prochloron didemni.

<400> SEQUENCE: 155
cgaagcttag ctgccgctgc cgctgccaac gccatcgtac gcg    43

<210> SEQ ID NO 156
<211> LENGTH: 44
<212> TYPE: DNA
<213> ORGANISM: Artificial Sequence
<220> FEATURE:
<223> OTHER INFORMATION: DNA sequence of primer mS-GS based on
      Prochloron didemni.

<400> SEQUENCE: 156
cgaagcttag ctgccgctgc cgctgccaac gccatcgtac gcag    44

<210> SEQ ID NO 157
<211> LENGTH: 43
<212> TYPE: DNA
<213> ORGANISM: Artificial Sequence
<220> FEATURE:
<223> OTHER INFORMATION: DNA sequence of primer mT-GG based on
      Prochloron didemni.

<400> SEQUENCE: 157
cgaagcttac ccgcccccgc ccccgccaac gccatcgtac gcg    43

<210> SEQ ID NO 158
<211> LENGTH: 43
<212> TYPE: DNA
<213> ORGANISM: Artificial Sequence
<220> FEATURE:
<223> OTHER INFORMATION: DNA sequence of primer mCS-GG based on
      Prochloron didemni.

<400> SEQUENCE: 158
cgaagcttac ccgcccccgc ccccgccaac gccatcgtac gca    43

<210> SEQ ID NO 159
<211> LENGTH: 42
<212> TYPE: DNA
<213> ORGANISM: Artificial Sequence
<220> FEATURE:
<223> OTHER INFORMATION: DNA sequence of primer wt-EGS1 based on
      Prochloron didemni.

<400> SEQUENCE: 159
ccgctgccgc taccctcaac gccatcgtac gcacaaaacg tg    42

<210> SEQ ID NO 160
<211> LENGTH: 36
<212> TYPE: DNA
<213> ORGANISM: Artificial Sequence
<220> FEATURE:
<223> OTHER INFORMATION: DNA sequence of primer GS3an2 based on
      Prochloron didemni.

<400> SEQUENCE: 160

```
tttccgcccc ccgtcctagc tgccgctgcc gctacc                              36
```

<210> SEQ ID NO 161
<211> LENGTH: 48
<212> TYPE: DNA
<213> ORGANISM: Artificial Sequence
<220> FEATURE:
<223> OTHER INFORMATION: DNA sequence of primer T7g10M based on
      Prochloron didemni.

<400> SEQUENCE: 161

```
taatacgact cactataggg ttaactttaa gaaggagata tacatatg                 48
```

<210> SEQ ID NO 162
<211> LENGTH: 53
<212> TYPE: DNA
<213> ORGANISM: Artificial Sequence
<220> FEATURE:
<223> OTHER INFORMATION: DNA sequence of primer XC3pool based on
      Prochloron didemni.
<220> FEATURE:
<221> NAME/KEY: misc_feature
<222> LOCATION: (23)..(23)
<223> OTHER INFORMATION: n stands for any base.
<220> FEATURE:
<221> NAME/KEY: misc_feature
<222> LOCATION: (24)..(24)
<223> OTHER INFORMATION: n stands for any base.
<220> FEATURE:
<221> NAME/KEY: misc_feature
<222> LOCATION: (29)..(29)
<223> OTHER INFORMATION: n stands for any base.
<220> FEATURE:
<221> NAME/KEY: misc_feature
<222> LOCATION: (30)..(30)
<223> OTHER INFORMATION: n stands for any base.
<220> FEATURE:
<221> NAME/KEY: misc_feature
<222> LOCATION: (35)..(35)
<223> OTHER INFORMATION: n stands for any base.
<220> FEATURE:
<221> NAME/KEY: misc_feature
<222> LOCATION: (36)..(36)
<223> OTHER INFORMATION: n stands for any base.

<400> SEQUENCE: 162

```
accaacgcca tcgtacgcac amnnacamnn acamnngctt gcctccaacc ccg           53
```

<210> SEQ ID NO 163
<211> LENGTH: 59
<212> TYPE: DNA
<213> ORGANISM: Artificial Sequence
<220> FEATURE:
<223> OTHER INFORMATION: DNA sequence of primer XC4pool based on
      Prochloron didemni.
<220> FEATURE:
<221> NAME/KEY: misc_feature
<222> LOCATION: (23)..(23)
<223> OTHER INFORMATION: n stands for any base.
<220> FEATURE:
<221> NAME/KEY: misc_feature
<222> LOCATION: (24)..(24)
<223> OTHER INFORMATION: n stands for any base.
<220> FEATURE:
<221> NAME/KEY: misc_feature
<222> LOCATION: (29)..(29)
<223> OTHER INFORMATION: n stands for any base.
<220> FEATURE:
<221> NAME/KEY: misc_feature
<222> LOCATION: (30)..(30)
<223> OTHER INFORMATION: n stands for any base.
<220> FEATURE:
<221> NAME/KEY: misc_feature
<222> LOCATION: (35)..(35)

<223> OTHER INFORMATION: n stands for any base.
<220> FEATURE:
<221> NAME/KEY: misc_feature
<222> LOCATION: (36)..(36)
<223> OTHER INFORMATION: n stands for any base.
<220> FEATURE:
<221> NAME/KEY: misc_feature
<222> LOCATION: (41)..(41)
<223> OTHER INFORMATION: n stands for any base.
<220> FEATURE:
<221> NAME/KEY: misc_feature
<222> LOCATION: (42)..(42)
<223> OTHER INFORMATION: n stands for any base.

<400> SEQUENCE: 163
accaacgcca tcgtacgcac amnnacamnn acamnnacam nngcttgcct ccaaccccg    59

<210> SEQ ID NO 164
<211> LENGTH: 65
<212> TYPE: DNA
<213> ORGANISM: Artificial Sequence
<220> FEATURE:
<223> OTHER INFORMATION: DNA sequence of primer XC5pool based on
      Prochloron didemni.
<220> FEATURE:
<221> NAME/KEY: misc_feature
<222> LOCATION: (23)..(23)
<223> OTHER INFORMATION: n stands for any base.
<220> FEATURE:
<221> NAME/KEY: misc_feature
<222> LOCATION: (24)..(24)
<223> OTHER INFORMATION: n stands for any base.
<220> FEATURE:
<221> NAME/KEY: misc_feature
<222> LOCATION: (29)..(29)
<223> OTHER INFORMATION: n stands for any base.
<220> FEATURE:
<221> NAME/KEY: misc_feature
<222> LOCATION: (30)..(30)
<223> OTHER INFORMATION: n stands for any base.
<220> FEATURE:
<221> NAME/KEY: misc_feature
<222> LOCATION: (35)..(35)
<223> OTHER INFORMATION: n stands for any base.
<220> FEATURE:
<221> NAME/KEY: misc_feature
<222> LOCATION: (36)..(36)
<223> OTHER INFORMATION: n stands for any base.
<220> FEATURE:
<221> NAME/KEY: misc_feature
<222> LOCATION: (41)..(41)
<223> OTHER INFORMATION: n stands for any base.
<220> FEATURE:
<221> NAME/KEY: misc_feature
<222> LOCATION: (42)..(42)
<223> OTHER INFORMATION: n stands for any base.
<220> FEATURE:
<221> NAME/KEY: misc_feature
<222> LOCATION: (47)..(47)
<223> OTHER INFORMATION: n stands for any base.
<220> FEATURE:
<221> NAME/KEY: misc_feature
<222> LOCATION: (48)..(48)
<223> OTHER INFORMATION: n stands for any base.

<400> SEQUENCE: 164
accaacgcca tcgtacgcac amnnacamnn acamnnacam nnacamnngc ttgcctccaa    60
ccccg                                                                65

<210> SEQ ID NO 165
<211> LENGTH: 71
<212> TYPE: DNA
<213> ORGANISM: Artificial Sequence
<220> FEATURE:

```
<223> OTHER INFORMATION: DNA sequence of primer XC6pool based on
      Prochloron didemni.
<220> FEATURE:
<221> NAME/KEY: misc_feature
<222> LOCATION: (23)..(23)
<223> OTHER INFORMATION: n stands for any base.
<220> FEATURE:
<221> NAME/KEY: misc_feature
<222> LOCATION: (24)..(24)
<223> OTHER INFORMATION: n stands for any base.
<220> FEATURE:
<221> NAME/KEY: misc_feature
<222> LOCATION: (29)..(29)
<223> OTHER INFORMATION: n stands for any base.
<220> FEATURE:
<221> NAME/KEY: misc_feature
<222> LOCATION: (30)..(30)
<223> OTHER INFORMATION: n stands for any base.
<220> FEATURE:
<221> NAME/KEY: misc_feature
<222> LOCATION: (35)..(35)
<223> OTHER INFORMATION: n stands for any base.
<220> FEATURE:
<221> NAME/KEY: misc_feature
<222> LOCATION: (36)..(36)
<223> OTHER INFORMATION: n stands for any base.
<220> FEATURE:
<221> NAME/KEY: misc_feature
<222> LOCATION: (41)..(41)
<223> OTHER INFORMATION: n stands for any base.
<220> FEATURE:
<221> NAME/KEY: misc_feature
<222> LOCATION: (42)..(42)
<223> OTHER INFORMATION: n stands for any base.
<220> FEATURE:
<221> NAME/KEY: misc_feature
<222> LOCATION: (47)..(47)
<223> OTHER INFORMATION: n stands for any base.
<220> FEATURE:
<221> NAME/KEY: misc_feature
<222> LOCATION: (48)..(48)
<223> OTHER INFORMATION: n stands for any base.
<220> FEATURE:
<221> NAME/KEY: misc_feature
<222> LOCATION: (53)..(53)
<223> OTHER INFORMATION: n stands for any base.
<220> FEATURE:
<221> NAME/KEY: misc_feature
<222> LOCATION: (54)..(54)
<223> OTHER INFORMATION: n stands for any base.

<400> SEQUENCE: 165
accaacgcca tcgtacgcac amnnacamnn acamnnacam nnacamnnac amnngcttgc      60
ctccaacccc g                                                          71

<210> SEQ ID NO 166
<211> LENGTH: 77
<212> TYPE: DNA
<213> ORGANISM: Artificial Sequence
<220> FEATURE:
<223> OTHER INFORMATION: DNA sequence of primer XC7pool based on
      Prochloron didemni.
<220> FEATURE:
<221> NAME/KEY: misc_feature
<222> LOCATION: (23)..(23)
<223> OTHER INFORMATION: n stands for any base.
<220> FEATURE:
<221> NAME/KEY: misc_feature
<222> LOCATION: (24)..(24)
<223> OTHER INFORMATION: n stands for any base.
<220> FEATURE:
<221> NAME/KEY: misc_feature
<222> LOCATION: (29)..(29)
<223> OTHER INFORMATION: n stands for any base.
<220> FEATURE:
<221> NAME/KEY: misc_feature
```

```
<222> LOCATION: (30)..(30)
<223> OTHER INFORMATION: n stands for any base.
<220> FEATURE:
<221> NAME/KEY: misc_feature
<222> LOCATION: (35)..(35)
<223> OTHER INFORMATION: n stands for any base.
<220> FEATURE:
<221> NAME/KEY: misc_feature
<222> LOCATION: (36)..(36)
<223> OTHER INFORMATION: n stands for any base.
<220> FEATURE:
<221> NAME/KEY: misc_feature
<222> LOCATION: (41)..(41)
<223> OTHER INFORMATION: n stands for any base.
<220> FEATURE:
<221> NAME/KEY: misc_feature
<222> LOCATION: (42)..(42)
<223> OTHER INFORMATION: n stands for any base.
<220> FEATURE:
<221> NAME/KEY: misc_feature
<222> LOCATION: (47)..(47)
<223> OTHER INFORMATION: n stands for any base.
<220> FEATURE:
<221> NAME/KEY: misc_feature
<222> LOCATION: (48)..(48)
<223> OTHER INFORMATION: n stands for any base.
<220> FEATURE:
<221> NAME/KEY: misc_feature
<222> LOCATION: (53)..(53)
<223> OTHER INFORMATION: n stands for any base.
<220> FEATURE:
<221> NAME/KEY: misc_feature
<222> LOCATION: (54)..(54)
<223> OTHER INFORMATION: n stands for any base.
<220> FEATURE:
<221> NAME/KEY: misc_feature
<222> LOCATION: (59)..(59)
<223> OTHER INFORMATION: n stands for any base.
<220> FEATURE:
<221> NAME/KEY: misc_feature
<222> LOCATION: (60)..(60)
<223> OTHER INFORMATION: n stands for any base.

<400> SEQUENCE: 166
accaacgcca tcgtacgcac amnnacamnn acamnnacam nnacamnnac amnnacamnn    60
gcttgcctcc aaccccg                                                  77

<210> SEQ ID NO 167
<211> LENGTH: 83
<212> TYPE: DNA
<213> ORGANISM: Artificial Sequence
<220> FEATURE:
<223> OTHER INFORMATION: DNA sequence of primer XC8pool based on
      Prochloron didemni.
<220> FEATURE:
<221> NAME/KEY: misc_feature
<222> LOCATION: (23)..(23)
<223> OTHER INFORMATION: n stands for any base.
<220> FEATURE:
<221> NAME/KEY: misc_feature
<222> LOCATION: (24)..(24)
<223> OTHER INFORMATION: n stands for any base.
<220> FEATURE:
<221> NAME/KEY: misc_feature
<222> LOCATION: (29)..(29)
<223> OTHER INFORMATION: n stands for any base.
<220> FEATURE:
<221> NAME/KEY: misc_feature
<222> LOCATION: (30)..(30)
<223> OTHER INFORMATION: n stands for any base.
<220> FEATURE:
<221> NAME/KEY: misc_feature
<222> LOCATION: (35)..(35)
<223> OTHER INFORMATION: n stands for any base.
<220> FEATURE:
<221> NAME/KEY: misc_feature
```

```
<222> LOCATION: (36)..(36)
<223> OTHER INFORMATION: n stands for any base.
<220> FEATURE:
<221> NAME/KEY: misc_feature
<222> LOCATION: (41)..(41)
<223> OTHER INFORMATION: n stands for any base.
<220> FEATURE:
<221> NAME/KEY: misc_feature
<222> LOCATION: (42)..(42)
<223> OTHER INFORMATION: n stands for any base.
<220> FEATURE:
<221> NAME/KEY: misc_feature
<222> LOCATION: (47)..(47)
<223> OTHER INFORMATION: n stands for any base.
<220> FEATURE:
<221> NAME/KEY: misc_feature
<222> LOCATION: (48)..(48)
<223> OTHER INFORMATION: n stands for any base.
<220> FEATURE:
<221> NAME/KEY: misc_feature
<222> LOCATION: (53)..(53)
<223> OTHER INFORMATION: n stands for any base.
<220> FEATURE:
<221> NAME/KEY: misc_feature
<222> LOCATION: (54)..(54)
<223> OTHER INFORMATION: n stands for any base.
<220> FEATURE:
<221> NAME/KEY: misc_feature
<222> LOCATION: (59)..(59)
<223> OTHER INFORMATION: n stands for any base.
<220> FEATURE:
<221> NAME/KEY: misc_feature
<222> LOCATION: (60)..(60)
<223> OTHER INFORMATION: n stands for any base.
<220> FEATURE:
<221> NAME/KEY: misc_feature
<222> LOCATION: (65)..(65)
<223> OTHER INFORMATION: n stands for any base.
<220> FEATURE:
<221> NAME/KEY: misc_feature
<222> LOCATION: (66)..(66)
<223> OTHER INFORMATION: n stands for any base.

<400> SEQUENCE: 167
accaacgcca tcgtacgcac amnnacamnn acamnnacam nnacamnnac amnnacamnn    60
acamnngctt gcctccaacc ccg                                           83

<210> SEQ ID NO 168
<211> LENGTH: 53
<212> TYPE: DNA
<213> ORGANISM: Artificial Sequence
<220> FEATURE:
<223> OTHER INFORMATION: DNA sequence of primer XCST3pool based on
      Prochloron didemni.
<220> FEATURE:
<221> NAME/KEY: misc_feature
<222> LOCATION: (23)..(23)
<223> OTHER INFORMATION: n stands for any base.
<220> FEATURE:
<221> NAME/KEY: misc_feature
<222> LOCATION: (24)..(24)
<223> OTHER INFORMATION: n stands for any base.
<220> FEATURE:
<221> NAME/KEY: misc_feature
<222> LOCATION: (29)..(29)
<223> OTHER INFORMATION: n stands for any base.
<220> FEATURE:
<221> NAME/KEY: misc_feature
<222> LOCATION: (30)..(30)
<223> OTHER INFORMATION: n stands for any base.
<220> FEATURE:
<221> NAME/KEY: misc_feature
<222> LOCATION: (35)..(35)
<223> OTHER INFORMATION: n stands for any base.
<220> FEATURE:
<221> NAME/KEY: misc_feature
```

<222> LOCATION: (36)..(36)
<223> OTHER INFORMATION: n stands for any base.

<400> SEQUENCE: 168
accaacgcca tcgtacgcas wmnnaswmnn aswmnngctt gcctccaacc ccg            53

<210> SEQ ID NO 169
<211> LENGTH: 59
<212> TYPE: DNA
<213> ORGANISM: Artificial Sequence
<220> FEATURE:
<223> OTHER INFORMATION: DNA sequence of primer XCST4pool based on
      Prochloron didemni.
<220> FEATURE:
<221> NAME/KEY: misc_feature
<222> LOCATION: (23)..(23)
<223> OTHER INFORMATION: n stands for any base.
<220> FEATURE:
<221> NAME/KEY: misc_feature
<222> LOCATION: (24)..(24)
<223> OTHER INFORMATION: n stands for any base.
<220> FEATURE:
<221> NAME/KEY: misc_feature
<222> LOCATION: (29)..(29)
<223> OTHER INFORMATION: n stands for any base.
<220> FEATURE:
<221> NAME/KEY: misc_feature
<222> LOCATION: (30)..(30)
<223> OTHER INFORMATION: n stands for any base.
<220> FEATURE:
<221> NAME/KEY: misc_feature
<222> LOCATION: (35)..(35)
<223> OTHER INFORMATION: n stands for any base.
<220> FEATURE:
<221> NAME/KEY: misc_feature
<222> LOCATION: (36)..(36)
<223> OTHER INFORMATION: n stands for any base.
<220> FEATURE:
<221> NAME/KEY: misc_feature
<222> LOCATION: (41)..(41)
<223> OTHER INFORMATION: n stands for any base.
<220> FEATURE:
<221> NAME/KEY: misc_feature
<222> LOCATION: (42)..(42)
<223> OTHER INFORMATION: n stands for any base.

<400> SEQUENCE: 169
accaacgcca tcgtacgcas wmnnaswmnn aswmnnaswm nngcttgcct ccaacccccg     59

<210> SEQ ID NO 170
<211> LENGTH: 65
<212> TYPE: DNA
<213> ORGANISM: Artificial Sequence
<220> FEATURE:
<223> OTHER INFORMATION: DNA sequence of primer XCST5pool based on
      Prochloron didemni.
<220> FEATURE:
<221> NAME/KEY: misc_feature
<222> LOCATION: (23)..(23)
<223> OTHER INFORMATION: n stands for any base.
<220> FEATURE:
<221> NAME/KEY: misc_feature
<222> LOCATION: (24)..(24)
<223> OTHER INFORMATION: n stands for any base.
<220> FEATURE:
<221> NAME/KEY: misc_feature
<222> LOCATION: (29)..(29)
<223> OTHER INFORMATION: n stands for any base.
<220> FEATURE:
<221> NAME/KEY: misc_feature
<222> LOCATION: (30)..(30)
<223> OTHER INFORMATION: n stands for any base.
<220> FEATURE:
<221> NAME/KEY: misc_feature
<222> LOCATION: (35)..(35)

```
<223> OTHER INFORMATION: n stands for any base.
<220> FEATURE:
<221> NAME/KEY: misc_feature
<222> LOCATION: (36)..(36)
<223> OTHER INFORMATION: n stands for any base.
<220> FEATURE:
<221> NAME/KEY: misc_feature
<222> LOCATION: (41)..(41)
<223> OTHER INFORMATION: n stands for any base.
<220> FEATURE:
<221> NAME/KEY: misc_feature
<222> LOCATION: (42)..(42)
<223> OTHER INFORMATION: n stands for any base.
<220> FEATURE:
<221> NAME/KEY: misc_feature
<222> LOCATION: (47)..(47)
<223> OTHER INFORMATION: n stands for any base.
<220> FEATURE:
<221> NAME/KEY: misc_feature
<222> LOCATION: (48)..(48)
<223> OTHER INFORMATION: n stands for any base.

<400> SEQUENCE: 170
accaacgcca tcgtacgcas wmnnaswmnn aswmnnaswm nnaswmnngc ttgcctccaa    60
ccccg                                                               65

<210> SEQ ID NO 171
<211> LENGTH: 71
<212> TYPE: DNA
<213> ORGANISM: Artificial Sequence
<220> FEATURE:
<223> OTHER INFORMATION: DNA sequence of primer XCST6pool based on
      Prochloron didemni.
<220> FEATURE:
<221> NAME/KEY: misc_feature
<222> LOCATION: (23)..(23)
<223> OTHER INFORMATION: n stands for any base.
<220> FEATURE:
<221> NAME/KEY: misc_feature
<222> LOCATION: (24)..(24)
<223> OTHER INFORMATION: n stands for any base.
<220> FEATURE:
<221> NAME/KEY: misc_feature
<222> LOCATION: (29)..(29)
<223> OTHER INFORMATION: n stands for any base.
<220> FEATURE:
<221> NAME/KEY: misc_feature
<222> LOCATION: (30)..(30)
<223> OTHER INFORMATION: n stands for any base.
<220> FEATURE:
<221> NAME/KEY: misc_feature
<222> LOCATION: (35)..(35)
<223> OTHER INFORMATION: n stands for any base.
<220> FEATURE:
<221> NAME/KEY: misc_feature
<222> LOCATION: (36)..(36)
<223> OTHER INFORMATION: n stands for any base.
<220> FEATURE:
<221> NAME/KEY: misc_feature
<222> LOCATION: (41)..(41)
<223> OTHER INFORMATION: n stands for any base.
<220> FEATURE:
<221> NAME/KEY: misc_feature
<222> LOCATION: (42)..(42)
<223> OTHER INFORMATION: n stands for any base.
<220> FEATURE:
<221> NAME/KEY: misc_feature
<222> LOCATION: (47)..(47)
<223> OTHER INFORMATION: n stands for any base.
<220> FEATURE:
<221> NAME/KEY: misc_feature
<222> LOCATION: (48)..(48)
<223> OTHER INFORMATION: n stands for any base.
<220> FEATURE:
<221> NAME/KEY: misc_feature
<222> LOCATION: (53)..(53)
```

```
<223> OTHER INFORMATION: n stands for any base.
<220> FEATURE:
<221> NAME/KEY: misc_feature
<222> LOCATION: (54)..(54)
<223> OTHER INFORMATION: n stands for any base.

<400> SEQUENCE: 171
accaacgcca tcgtacgcas wmnnaswmnn aswmnnaswm nnaswmnnas wmnngcttgc      60
ctccaacccc g                                                           71

<210> SEQ ID NO 172
<211> LENGTH: 51
<212> TYPE: DNA
<213> ORGANISM: Artificial Sequence
<220> FEATURE:
<223> OTHER INFORMATION: DNA sequence of primer PatEpool.ex based on
      Prochloron didemni.

<400> SEQUENCE: 172
tttccgcccc ccgtcctagc tgccgctgcc gctaccaacg ccatcgtacg c               51

<210> SEQ ID NO 173
<211> LENGTH: 5
<212> TYPE: PRT
<213> ORGANISM: Artificial Sequence
<220> FEATURE:
<223> OTHER INFORMATION: An example of Recognition Sequence 1 based on
      Prochloron didemni.

<400> SEQUENCE: 173

Gly Gly Gly Gly Gly
1               5

<210> SEQ ID NO 174
<211> LENGTH: 5
<212> TYPE: PRT
<213> ORGANISM: Artificial Sequence
<220> FEATURE:
<223> OTHER INFORMATION: An example of Recognition Sequence 1 based on
      Prochloron didemni.

<400> SEQUENCE: 174

Gln Gln Gln Gln Gln
1               5

<210> SEQ ID NO 175
<211> LENGTH: 5
<212> TYPE: PRT
<213> ORGANISM: Artificial Sequence
<220> FEATURE:
<223> OTHER INFORMATION: An example of Recognition Sequence 1 based on
      Prochloron didemni.

<400> SEQUENCE: 175

Leu Leu Leu Leu Leu
1               5

<210> SEQ ID NO 176
<211> LENGTH: 5
<212> TYPE: PRT
<213> ORGANISM: Artificial Sequence
<220> FEATURE:
<223> OTHER INFORMATION: An example of Recognition Sequence 1 based on
      Prochloron didemni.

<400> SEQUENCE: 176

Pro Pro Pro Pro Pro
```

-continued

```
<210> SEQ ID NO 177
<211> LENGTH: 24
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 177

Met Lys Glu Gln Asn Ser Phe Asn Leu Leu Gln Glu Val Thr Glu Ser
1               5                   10                  15

Glu Leu Asp Leu Ile Leu Gly Ala
            20

<210> SEQ ID NO 178
<211> LENGTH: 25
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 178

Met Ile Leu Ala Ser Leu Ser Thr Phe Gln Gln Met Trp Ile Ser Lys
1               5                   10                  15

Gln Glu Tyr Asp Glu Ala Gly Asp Ala
            20                  25

<210> SEQ ID NO 179
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 179

Met Glu Leu Gln Leu Arg Pro Ser Gly Leu Glu Lys Lys Gln Ala Pro
1               5                   10                  15

Ile Ser Glu Leu Asn Ile Ala Gln Thr Gln Gly Gly Asp Ser Gln Val
            20                  25                  30

Leu Ala Leu Asn Ala
        35

<210> SEQ ID NO 180
<211> LENGTH: 2
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 180

Val Cys
1

<210> SEQ ID NO 181
<211> LENGTH: 4
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
``` didemni.

<400> SEQUENCE: 181

Val Cys Ala Cys
1

<210> SEQ ID NO 182
<211> LENGTH: 22
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 182

Val Cys Ala Cys Ile Cys Phe Cys Val Cys Ala Cys Val Cys Ile Cys
1               5                   10                  15

Tyr Cys Phe Cys Ile Cys
            20

<210> SEQ ID NO 183
<211> LENGTH: 36
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 183

Val Cys Ala Cys Ile Cys Phe Cys Val Cys Val Cys Phe Cys Tyr Cys
1               5                   10                  15

Ala Cys Tyr Cys Ile Cys Phe Cys Ala Cys Val Cys Ile Cys Tyr Cys
            20                  25                  30

Phe Cys Ile Cys
        35

<210> SEQ ID NO 184
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 184

Arg Thr Asp Thr Asp Thr Arg Thr
1               5

<210> SEQ ID NO 185
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 185

Arg Ser Asp Ser Asp Ser Arg Ser
1               5

<210> SEQ ID NO 186
<211> LENGTH: 6

```
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 186

Cys Cys Cys Cys Cys Cys
1               5

<210> SEQ ID NO 187
<211> LENGTH: 6
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 187

Thr Thr Thr Thr Thr Thr
1               5

<210> SEQ ID NO 188
<211> LENGTH: 6
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 188

Ser Ser Ser Ser Ser Ser
1               5

<210> SEQ ID NO 189
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 189

Val Phe Ala Thr Ile Thr Phe Thr
1               5

<210> SEQ ID NO 190
<211> LENGTH: 8
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 190

Cys Phe Ala Thr Ile Thr Phe Thr
1               5

<210> SEQ ID NO 191
<211> LENGTH: 8
<212> TYPE: PRT
<213> ORGANISM: Artificial Sequence
<220> FEATURE:
<223> OTHER INFORMATION: An example of newly identified substrate
``` sequence of azoline ring introducing enzyme based on Prochloron didemni.

<400> SEQUENCE: 191

Val Phe Ala Leu Cys Cys Cys Cys
1               5

<210> SEQ ID NO 192
<211> LENGTH: 2
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 192

Val Thr
1

<210> SEQ ID NO 193
<211> LENGTH: 4
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 193

Val Thr Ala Cys
1

<210> SEQ ID NO 194
<211> LENGTH: 12
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 194

Val Thr Ala Cys Ile Thr Phe Cys Val Thr Ala Cys
1               5                   10

<210> SEQ ID NO 195
<211> LENGTH: 16
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 195

Val Thr Ala Cys Ile Thr Phe Cys Val Thr Ala Cys Val Ser Ile Cys
1               5                   10                  15

<210> SEQ ID NO 196
<211> LENGTH: 22
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 196

```
Val Thr Ala Cys Ile Thr Phe Cys Val Thr Ala Cys Val Ser Ile Cys
1               5                   10                  15

Tyr Thr Phe Cys Ile Thr
            20
```

<210> SEQ ID NO 197
<211> LENGTH: 36
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 197

```
Val Thr Ala Cys Ile Thr Phe Cys Val Thr Ala Cys Val Ser Ile Cys
1               5                   10                  15

Tyr Thr Phe Cys Ile Thr Phe Cys Ala Thr Val Cys Ile Ser Tyr Cys
            20                  25                  30

Phe Thr Ile Cys
            35
```

<210> SEQ ID NO 198
<211> LENGTH: 16
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 198

```
Val Thr Ala Cys Ile Thr Phe Cys Val Thr Ala Cys Val Thr Ile Cys
1               5                   10                  15
```

<210> SEQ ID NO 199
<211> LENGTH: 22
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 199

```
Val Thr Ala Cys Ile Thr Phe Cys Val Thr Ala Cys Val Thr Ile Cys
1               5                   10                  15

Tyr Thr Phe Cys Ile Thr
            20
```

<210> SEQ ID NO 200
<211> LENGTH: 36
<212> TYPE: PRT
<213> ORGANISM: Artificial Sequence
<220> FEATURE:
<223> OTHER INFORMATION: An example of newly identified substrate
      sequence of azoline ring introducing enzyme based on Prochloron
      didemni.

<400> SEQUENCE: 200

```
Val Thr Ala Cys Ile Thr Phe Cys Val Thr Ala Cys Val Thr Ile Cys
1               5                   10                  15

Tyr Thr Phe Cys Ile Thr Phe Cys Ala Thr Val Cys Ile Thr Tyr Cys
            20                  25                  30
```

```
Phe Thr Ile Cys
        35

<210> SEQ ID NO 201
<211> LENGTH: 42
<212> TYPE: PRT
<213> ORGANISM: Artificial Sequence
<220> FEATURE:
<223> OTHER INFORMATION: Amino acid sequence of a peptide encoded by
      PatEpre based on Prochloron didemni.

<400> SEQUENCE: 201

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser
        35                  40

<210> SEQ ID NO 202
<211> LENGTH: 51
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MISC_FEATURE
<222> LOCATION: (43)..(43)
<223> OTHER INFORMATION: Xaa stands for a Cassette region consisting of
      more than one amino acid.

<400> SEQUENCE: 202

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Xaa Ala Tyr Asp Gly Val
        35                  40                  45

Glu Pro Ser
    50

<210> SEQ ID NO 203
<211> LENGTH: 44
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MISC_FEATURE
<222> LOCATION: (43)..(43)
<223> OTHER INFORMATION: Xaa stands for a Cassette region consisting of
      more than one amino acid.
<220> FEATURE:
<221> NAME/KEY: MISC_FEATURE
<222> LOCATION: (44)..(44)
<223> OTHER INFORMATION: Xaa stands for a Recognition Sequence 2
      consisting of more than one amino acid.

<400> SEQUENCE: 203

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Xaa Xaa
```

```
                35                  40

<210> SEQ ID NO 204
<211> LENGTH: 65
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION

<400> SEQUENCE: 204

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Leu Cys Gly Cys Thr Ser
        35                  40                  45

Tyr Cys Tyr Thr Val Ser Ala Tyr Asp Gly Val Gly Ser Gly Ser Gly
    50                  55                  60

Ser
65

<210> SEQ ID NO 205
<211> LENGTH: 65
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION

<400> SEQUENCE: 205

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Ser Cys Asn Ser Ile Ser
        35                  40                  45

Met Ser Ser Thr Pro Ser Ala Tyr Asp Gly Val Gly Ser Gly Ser Gly
    50                  55                  60

Ser
65

<210> SEQ ID NO 206
<211> LENGTH: 65
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION

<400> SEQUENCE: 206

Met Asn Lys Lys Asn Ile Leu Pro Gln Gln Gly Gln Pro Val Ile Arg
1               5                   10                  15
```

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Cys Thr Leu Ser Asn Thr
            35                  40                  45

Pro Ser Ser Thr Leu Thr Ala Tyr Asp Gly Val Gly Ser Gly Ser Gly
        50                  55                  60

Ser
65

<210> SEQ ID NO 207
<211> LENGTH: 65
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION

<400> SEQUENCE: 207

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Leu Ser Leu Ser Asn Thr
            35                  40                  45

Phe Thr Glu Ser Glu Ser Ala Tyr Asp Gly Val Gly Ser Gly Ser Gly
        50                  55                  60

Ser
65

<210> SEQ ID NO 208
<211> LENGTH: 65
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION

<400> SEQUENCE: 208

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Ser Ser Leu Cys Ile Thr
            35                  40                  45

Pro Ser Ser Thr Gln Thr Ala Tyr Asp Gly Val Gly Ser Gly Ser Gly
        50                  55                  60

Ser
65

<210> SEQ ID NO 209
<211> LENGTH: 59
<212> TYPE: PRT
<213> ORGANISM: Artificial Sequence
<220> FEATURE:

<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION

<400> SEQUENCE: 209

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Leu Cys Gly Cys Thr Ser
        35                  40                  45

Tyr Cys Tyr Thr Val Ser Ala Tyr Asp Gly Val
    50                  55

<210> SEQ ID NO 210
<211> LENGTH: 59
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION

<400> SEQUENCE: 210

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Ser Cys Asn Ser Ile Ser
        35                  40                  45

Met Ser Ser Thr Pro Ser Ala Tyr Asp Gly Val
    50                  55

<210> SEQ ID NO 211
<211> LENGTH: 59
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION

<400> SEQUENCE: 211

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Ser Ser Leu Cys Ile Thr
        35                  40                  45

Pro Ser Ser Thr Gln Thr Ala Tyr Asp Gly Val
    50                  55

<210> SEQ ID NO 212
<211> LENGTH: 54
<212> TYPE: PRT

<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MISC_FEATURE
<222> LOCATION: (44)..(44)
<223> OTHER INFORMATION: Xaa stands for iPrSer
<220> FEATURE:
<221> NAME/KEY: MISC_FEATURE
<222> LOCATION: (46)..(46)
<223> OTHER INFORMATION: Xaa stands for iPrSer.

<400> SEQUENCE: 212

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Val Xaa Ala Xaa Ala Tyr
        35                  40                  45

Asp Gly Val Glu Pro Ser
    50

<210> SEQ ID NO 213
<211> LENGTH: 54
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MISC_FEATURE
<222> LOCATION: (44)..(44)
<223> OTHER INFORMATION: Xaa stands for PhSer.
<220> FEATURE:
<221> NAME/KEY: MISC_FEATURE
<222> LOCATION: (46)..(46)
<223> OTHER INFORMATION: Xaa stands for PhSer.

<400> SEQUENCE: 213

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Val Xaa Ala Xaa Ala Tyr
        35                  40                  45

Asp Gly Val Glu Pro Ser
    50

<210> SEQ ID NO 214
<211> LENGTH: 58
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION
<220> FEATURE:

<221> NAME/KEY: MISC_FEATURE
<222> LOCATION: (44)..(44)
<223> OTHER INFORMATION: Xaa stands for iPrSer.
<220> FEATURE:
<221> NAME/KEY: MISC_FEATURE
<222> LOCATION: (46)..(46)
<223> OTHER INFORMATION: Xaa stands for iPrSer.
<220> FEATURE:
<221> NAME/KEY: MISC_FEATURE
<222> LOCATION: (48)..(48)
<223> OTHER INFORMATION: Xaa stands for iPrSer.
<220> FEATURE:
<221> NAME/KEY: MISC_FEATURE
<222> LOCATION: (50)..(50)
<223> OTHER INFORMATION: Xaa stands for iPrSer.

<400> SEQUENCE: 214

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Val Xaa Ala Xaa Ile Xaa
        35                  40                  45

Phe Xaa Ala Tyr Asp Gly Val Glu Pro Ser
    50                  55

<210> SEQ ID NO 215
<211> LENGTH: 58
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MISC_FEATURE
<222> LOCATION: (44)..(44)
<223> OTHER INFORMATION: Xaa stands for PhSer.
<220> FEATURE:
<221> NAME/KEY: MISC_FEATURE
<222> LOCATION: (46)..(46)
<223> OTHER INFORMATION: Xaa stands for PhSer.
<220> FEATURE:
<221> NAME/KEY: MISC_FEATURE
<222> LOCATION: (48)..(48)
<223> OTHER INFORMATION: Xaa stands for PhSer.
<220> FEATURE:
<221> NAME/KEY: MISC_FEATURE
<222> LOCATION: (50)..(50)
<223> OTHER INFORMATION: Xaa stands for PhSer.

<400> SEQUENCE: 215

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Val Xaa Ala Xaa Ile Xaa
        35                  40                  45

Phe Xaa Ala Tyr Asp Gly Val Glu Pro Ser
    50                  55

<210> SEQ ID NO 216
<211> LENGTH: 23
<212> TYPE: PRT
<213> ORGANISM: Artificial Sequence
<220> FEATURE:

```
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MISC_FEATURE
<222> LOCATION: (20)..(20)
<223> OTHER INFORMATION: Xaa stands for Dap.
<220> FEATURE:
<221> NAME/KEY: MISC_FEATURE
<222> LOCATION: (22)..(22)
<223> OTHER INFORMATION: Xaa stands for Dap.

<400> SEQUENCE: 216

Met Leu Ala Glu Leu Ser Glu Glu Ala Leu Gly Asp Ala Gly Leu Glu
1               5                   10                  15

Ala Ser Val Xaa Ala Xaa Ala
            20

<210> SEQ ID NO 217
<211> LENGTH: 23
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MISC_FEATURE
<222> LOCATION: (20)..(20)
<223> OTHER INFORMATION: Xaa stands for PhSer.
<220> FEATURE:
<221> NAME/KEY: MISC_FEATURE
<222> LOCATION: (22)..(22)
<223> OTHER INFORMATION: Xaa stands for PhSer.

<400> SEQUENCE: 217

Met Leu Ala Glu Leu Ser Glu Glu Ala Leu Gly Asp Ala Gly Leu Glu
1               5                   10                  15

Ala Ser Val Xaa Ala Xaa Ala
            20

<210> SEQ ID NO 218
<211> LENGTH: 23
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MISC_FEATURE
<222> LOCATION: (20)..(20)
<223> OTHER INFORMATION: Xaa stands for Dap.
<220> FEATURE:
<221> NAME/KEY: MISC_FEATURE
<222> LOCATION: (22)..(22)
<223> OTHER INFORMATION: Xaa stands for Dap.

<400> SEQUENCE: 218

Met Leu Ala Glu Leu Ser Glu Glu Ala Leu Gly Asp Ala Gly Gly Gly
1               5                   10                  15

Gly Gly Val Xaa Ala Xaa Ala
```

```
<210> SEQ ID NO 219
<211> LENGTH: 23
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MISC_FEATURE
<222> LOCATION: (20)..(20)
<223> OTHER INFORMATION: Xaa stands for PhSer.
<220> FEATURE:
<221> NAME/KEY: MISC_FEATURE
<222> LOCATION: (22)..(22)
<223> OTHER INFORMATION: Xaa stands for PhSer.

<400> SEQUENCE: 219

Met Leu Ala Glu Leu Ser Glu Glu Ala Leu Gly Asp Ala Gly Gly Gly
1               5                   10                  15

Gly Gly Val Xaa Ala Xaa Ala
            20

<210> SEQ ID NO 220
<211> LENGTH: 54
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MISC_FEATURE
<222> LOCATION: (44)..(44)
<223> OTHER INFORMATION: Xaa stands for Dap.
<220> FEATURE:
<221> NAME/KEY: MISC_FEATURE
<222> LOCATION: (46)..(46)
<223> OTHER INFORMATION: Xaa stands for Dap.

<400> SEQUENCE: 220

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala Gly Leu Glu Ala Ser Val Xaa Ala Xaa Ala Tyr
        35                  40                  45

Asp Gly Val Glu Pro Ser
    50

<210> SEQ ID NO 221
<211> LENGTH: 58
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: FORMYLATION
<220> FEATURE:
```

```
<221> NAME/KEY: MISC_FEATURE
<222> LOCATION: (44)..(44)
<223> OTHER INFORMATION: Xaa stands for Dap.
<220> FEATURE:
<221> NAME/KEY: MISC_FEATURE
<222> LOCATION: (46)..(46)
<223> OTHER INFORMATION: Xaa stands for Dap.
<220> FEATURE:
<221> NAME/KEY: MISC_FEATURE
<222> LOCATION: (48)..(48)
<223> OTHER INFORMATION: Xaa stands for Dap.
<220> FEATURE:
<221> NAME/KEY: MISC_FEATURE
<222> LOCATION: (50)..(50)
<223> OTHER INFORMATION: Xaa stands for Dap.

<400> SEQUENCE: 221

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
                20                  25                  30

Ala Leu Gly Asp Ala Gly Leu Glu Ala Ser Val Xaa Ala Xaa Ile Xaa
            35                  40                  45

Phe Xaa Ala Tyr Asp Gly Val Glu Pro Ser
    50                  55

<210> SEQ ID NO 222
<211> LENGTH: 26
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (19)..(19)
<223> OTHER INFORMATION: Xaa stands for Dap.
<220> FEATURE:
<221> NAME/KEY: MISC_FEATURE
<222> LOCATION: (21)..(21)
<223> OTHER INFORMATION: Xaa stands for Dap.
<220> FEATURE:
<221> NAME/KEY: MISC_FEATURE
<222> LOCATION: (23)..(23)
<223> OTHER INFORMATION: Xaa stands for Dap.
<220> FEATURE:
<221> NAME/KEY: MISC_FEATURE
<222> LOCATION: (25)..(25)
<223> OTHER INFORMATION: Xaa stands for Dap.

<400> SEQUENCE: 222

Leu Ala Glu Leu Ser Glu Glu Ala Leu Gly Asp Ala Gly Leu Glu Ala
1               5                   10                  15

Ser Val Xaa Ala Xaa Ile Xaa Phe Xaa Ala
                20                  25

<210> SEQ ID NO 223
<211> LENGTH: 26
<212> TYPE: PRT
<213> ORGANISM: Artificial Sequence
<220> FEATURE:
<223> OTHER INFORMATION: Amino acid sequence of an example of substrate
      peptide based on Prochloron didemni.
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MISC_FEATURE
<222> LOCATION: (19)..(19)
<223> OTHER INFORMATION: Xaa stands for Dap.
<220> FEATURE:
<221> NAME/KEY: MISC_FEATURE
<222> LOCATION: (21)..(21)
<223> OTHER INFORMATION: Xaa stands for Dap.
<220> FEATURE:
<221> NAME/KEY: MISC_FEATURE
<222> LOCATION: (23)..(23)
<223> OTHER INFORMATION: Xaa stands for Dap.
<220> FEATURE:
<221> NAME/KEY: MISC_FEATURE
<222> LOCATION: (25)..(25)
<223> OTHER INFORMATION: Xaa stands for Dap.

<400> SEQUENCE: 223

Leu Ala Glu Leu Ser Glu Glu Ala Leu Gly Asp Ala Gly Gly Gly Gly
1               5                   10                  15

Gly Val Xaa Ala Xaa Ile Xaa Phe Xaa Ala
            20                  25

<210> SEQ ID NO 224
<211> LENGTH: 16
<212> TYPE: DNA
<213> ORGANISM: Artificial Sequence
<220> FEATURE:
<223> OTHER INFORMATION: Puromycin Linker based on Prochloron didemni.
<220> FEATURE:
<221> NAME/KEY: misc_feature
<222> LOCATION: (16)..(16)
<223> OTHER INFORMATION: Cytosine residue to which (SPC18)5CC(Pu) is
      linked. SPC18 stands for PEG in which the total number of C and O
      is 18.

<400> SEQUENCE: 224
ctcccgcccc ccgtcc                                                       16

<210> SEQ ID NO 225
<211> LENGTH: 39
<212> TYPE: DNA
<213> ORGANISM: Artificial Sequence
<220> FEATURE:
<223> OTHER INFORMATION: Nucleic acid sequence of primer m49 based on
      Prochloron didemni.

<400> SEQUENCE: 225
tcaacgccat cgtacgcaca aacgcttgcc tccaacccc                              39

<210> SEQ ID NO 226
<211> LENGTH: 45
<212> TYPE: DNA
<213> ORGANISM: Artificial Sequence
<220> FEATURE:
<223> OTHER INFORMATION: Nucleic acid sequence of primer m50 based on
      Prochloron didemni.

<400> SEQUENCE: 226
tcaacgccat cgtacgcaca tgcacaaacg cttgcctcca acccc                       45

<210> SEQ ID NO 227
<211> LENGTH: 70
<212> TYPE: DNA
<213> ORGANISM: Artificial Sequence
<220> FEATURE:
<223> OTHER INFORMATION: Nucleic acid sequence of primer m51-a based on
      Prochloron didemni.

<400> SEQUENCE: 227
```
acaataacaa atgcaaacac atgcacaaac gcagaagcag atacatgcac aaacgcttgc    60
ctccaacccc                                                           70

<210> SEQ ID NO 228
<211> LENGTH: 69
<212> TYPE: DNA
<213> ORGANISM: Artificial Sequence
<220> FEATURE:
<223> OTHER INFORMATION: Nucleic acid sequence of primer m51-b based on
      Prochloron didemni.

<400> SEQUENCE: 228
cgaagcttaa gatggctcaa cgccatcgta cgcacaaata caaaaacaat aacaaatgca    60
aacacatgc                                                            69

<210> SEQ ID NO 229
<211> LENGTH: 65
<212> TYPE: DNA
<213> ORGANISM: Artificial Sequence
<220> FEATURE:
<223> OTHER INFORMATION: Nucleic acid sequence of primer m52-a based on
      Prochloron didemni.

<400> SEQUENCE: 229
cacagtagca aaacacaca caaacgcaga agcagataca tgcacaaacg cttgcctcca    60
acccc                                                                65

<210> SEQ ID NO 230
<211> LENGTH: 68
<212> TYPE: DNA
<213> ORGANISM: Artificial Sequence
<220> FEATURE:
<223> OTHER INFORMATION: Nucleic acid sequence of primer m52-b based on
      Prochloron didemni.

<400> SEQUENCE: 230
acaataacaa atgcaaacac atgcacaaaa acaaatacag tagcaagcac agtagcaaaa    60
acacacac                                                             68

<210> SEQ ID NO 231
<211> LENGTH: 47
<212> TYPE: DNA
<213> ORGANISM: Artificial Sequence
<220> FEATURE:
<223> OTHER INFORMATION: Nucleic acid sequence of primer m53-a based on
      Prochloron didemni.

<400> SEQUENCE: 231
cgtacgcggt acgggtgtcg gtgtcggtac ggcttgcctc caacccc                  47

<210> SEQ ID NO 232
<211> LENGTH: 41
<212> TYPE: DNA
<213> ORGANISM: Artificial Sequence
<220> FEATURE:
<223> OTHER INFORMATION: Nucleic acid sequence of primer m53-b based on
      Prochloron didemni.

<400> SEQUENCE: 232
cgaagcttaa gatggctcaa cgccatcgta cgcggtacgg g                        41

<210> SEQ ID NO 233
<211> LENGTH: 49

```
<212> TYPE: DNA
<213> ORGANISM: Artificial Sequence
<220> FEATURE:
<223> OTHER INFORMATION: Nucleic acid sequence of primer m54-a based on
      Prochloron didemni.

<400> SEQUENCE: 233
atcgtacgca gaacgagagt cagagtcaga acggcttgcc tccaacccc                  49

<210> SEQ ID NO 234
<211> LENGTH: 43
<212> TYPE: DNA
<213> ORGANISM: Artificial Sequence
<220> FEATURE:
<223> OTHER INFORMATION: Nucleic acid sequence of primer m54-b based on
      Prochloron didemni.

<400> SEQUENCE: 234
cgaagcttaa gatggctcaa cgccatcgta cgcagaacga gag                        43

<210> SEQ ID NO 235
<211> LENGTH: 40
<212> TYPE: DNA
<213> ORGANISM: Artificial Sequence
<220> FEATURE:
<223> OTHER INFORMATION: Nucleic acid sequence of primer m55 based on
      Prochloron didemni.

<400> SEQUENCE: 235
gtacgcgcaa caacagcagc aacagcttgc ctccaacccc                            40

<210> SEQ ID NO 236
<211> LENGTH: 46
<212> TYPE: DNA
<213> ORGANISM: Artificial Sequence
<220> FEATURE:
<223> OTHER INFORMATION: Nucleic acid sequence of primer m56 based on
      Prochloron didemni.

<400> SEQUENCE: 236
gccatcgtac gccgtggtgg tcgtcgtggt gcttgcctcc aacccc                     46

<210> SEQ ID NO 237
<211> LENGTH: 44
<212> TYPE: DNA
<213> ORGANISM: Artificial Sequence
<220> FEATURE:
<223> OTHER INFORMATION: Nucleic acid sequence of primer m57-c based on
      Prochloron didemni.

<400> SEQUENCE: 237
catcgtacgc agatgatgaa gaagatgagc ttgcctccaa cccc                       44

<210> SEQ ID NO 238
<211> LENGTH: 44
<212> TYPE: DNA
<213> ORGANISM: Artificial Sequence
<220> FEATURE:
<223> OTHER INFORMATION: Nucleic acid sequence of primer m57-d based on
      Prochloron didemni.

<400> SEQUENCE: 238
cgaagcttaa gatggctcaa cgccatcgta cgcagatgat gaag                       44

<210> SEQ ID NO 239
<211> LENGTH: 49
<212> TYPE: DNA
```

<213> ORGANISM: Artificial Sequence
<220> FEATURE:
<223> OTHER INFORMATION: Nucleic acid sequence of primer m58 based on
      Prochloron didemni.

<400> SEQUENCE: 239
atcgtacgcg gtaaacgtga tggtcgcaaa aacgcttgcc tccaacccc          49

<210> SEQ ID NO 240
<211> LENGTH: 49
<212> TYPE: DNA
<213> ORGANISM: Artificial Sequence
<220> FEATURE:
<223> OTHER INFORMATION: Nucleic acid sequence of primer m59 based on
      Prochloron didemni.

<400> SEQUENCE: 240
atcgtacgcg gtaaacgtga tggtcgcaaa acagcttgcc tccaacccc          49

<210> SEQ ID NO 241
<211> LENGTH: 57
<212> TYPE: DNA
<213> ORGANISM: Artificial Sequence
<220> FEATURE:
<223> OTHER INFORMATION: Nucleic acid sequence of primer m68 based on
      Prochloron didemni.

<400> SEQUENCE: 241
tcaacgccat cgtacgcgca acaacagcat aacgcaaaaa cgcttgcctc caacccc    57

<210> SEQ ID NO 242
<211> LENGTH: 39
<212> TYPE: DNA
<213> ORGANISM: Artificial Sequence
<220> FEATURE:
<223> OTHER INFORMATION: Nucleic acid sequence of primer n119 based on
      Prochloron didemni.

<400> SEQUENCE: 242
tcaacgccat cgtacgcggt aacgcttgcc tccaacccc                     39

<210> SEQ ID NO 243
<211> LENGTH: 45
<212> TYPE: DNA
<213> ORGANISM: Artificial Sequence
<220> FEATURE:
<223> OTHER INFORMATION: Nucleic acid sequence of primer m196 based on
      Prochloron didemni.

<400> SEQUENCE: 243
tcaacgccat cgtacgcaca cgccgtaacg cttgcctcca acccc              45

<210> SEQ ID NO 244
<211> LENGTH: 69
<212> TYPE: DNA
<213> ORGANISM: Artificial Sequence
<220> FEATURE:
<223> OTHER INFORMATION: Nucleic acid sequence of primer m197 based on
      Prochloron didemni.

<400> SEQUENCE: 244
tcaacgccat cgtacgcaca cgccgtaaca caaaacgtga tacacgccgt aacgcttgcc    60
tccaacccc                                                         69

<210> SEQ ID NO 245
<211> LENGTH: 48

-continued

<212> TYPE: DNA
<213> ORGANISM: Artificial Sequence
<220> FEATURE:
<223> OTHER INFORMATION: Nucleic acid sequence of primer m198-a based on
      Prochloron didemni.

<400> SEQUENCE: 245
gccgtaacac aaaacgtgat acacgccgta acgcttgcct ccaacccc                  48

<210> SEQ ID NO 246
<211> LENGTH: 51
<212> TYPE: DNA
<213> ORGANISM: Artificial Sequence
<220> FEATURE:
<223> OTHER INFORMATION: Nucleic acid sequence of primer m198-b based on
      Prochloron didemni.

<400> SEQUENCE: 246
tcaacgccat cgtacgcaca aatagaaaca cacgccgtaa cacaaaacgt g              51

<210> SEQ ID NO 247
<211> LENGTH: 68
<212> TYPE: DNA
<213> ORGANISM: Artificial Sequence
<220> FEATURE:
<223> OTHER INFORMATION: Nucleic acid sequence of primer m199-a based on
      Prochloron didemni.

<400> SEQUENCE: 247
tgtaacaaat agaaacacac gccgtaacac aaaacgtgat acacgccgta acgcttgcct     60
ccaacccc                                                              68

<210> SEQ ID NO 248
<211> LENGTH: 53
<212> TYPE: DNA
<213> ORGANISM: Artificial Sequence
<220> FEATURE:
<223> OTHER INFORMATION: Nucleic acid sequence of primer m199-b based on
      Prochloron didemni.

<400> SEQUENCE: 248
tcaacgccat cgtacgcggt aatacagaag gtgtaacaaa tagaaacaca cgc            53

<210> SEQ ID NO 249
<211> LENGTH: 61
<212> TYPE: DNA
<213> ORGANISM: Artificial Sequence
<220> FEATURE:
<223> OTHER INFORMATION: Nucleic acid sequence of primer m200-a based on
      Prochloron didemni.

<400> SEQUENCE: 249
aagaaataca aacggttgca caaaaggtaa tacagaaggt gtaacaaata gaaacacacg     60
c                                                                     61

<210> SEQ ID NO 250
<211> LENGTH: 55
<212> TYPE: DNA
<213> ORGANISM: Artificial Sequence
<220> FEATURE:
<223> OTHER INFORMATION: Nucleic acid sequence of primer m200-b based on
      Prochloron didemni.

<400> SEQUENCE: 250
tcaacgccat cgtacgcaca aatggtgaaa cagtaagaaa tacaaacggt tgcac          55

<210> SEQ ID NO 251
<211> LENGTH: 51
<212> TYPE: DNA
<213> ORGANISM: Artificial Sequence
<220> FEATURE:
<223> OTHER INFORMATION: Nucleic acid sequence of primer m201 based on
      Prochloron didemni.

<400> SEQUENCE: 251
tcaacgccat cgtacgcaca aatggtaaca cacgccgtaa cacaaaacgt g          51

<210> SEQ ID NO 252
<211> LENGTH: 68
<212> TYPE: DNA
<213> ORGANISM: Artificial Sequence
<220> FEATURE:
<223> OTHER INFORMATION: Nucleic acid sequence of primer m202-a based on
      Prochloron didemni.

<400> SEQUENCE: 252
tgtaacaaat ggtaacacac gccgtaacac aaaacgtgat acacgccgta acgcttgcct    60
ccaacccc                                                             68

<210> SEQ ID NO 253
<211> LENGTH: 52
<212> TYPE: DNA
<213> ORGANISM: Artificial Sequence
<220> FEATURE:
<223> OTHER INFORMATION: Nucleic acid sequence of primer m202-b based on
      Prochloron didemni.

<400> SEQUENCE: 253
tcaacgccat cgtacgcggt aatacagaag gtgtaacaaa tggtaacaca cg           52

<210> SEQ ID NO 254
<211> LENGTH: 60
<212> TYPE: DNA
<213> ORGANISM: Artificial Sequence
<220> FEATURE:
<223> OTHER INFORMATION: Nucleic acid sequence of primer m203-a based on
      Prochloron didemni.

<400> SEQUENCE: 254
aagtaataca acggttgca caaaaggtaa tacagaaggt gtaacaaatg gtaacacacg    60

<210> SEQ ID NO 255
<211> LENGTH: 55
<212> TYPE: DNA
<213> ORGANISM: Artificial Sequence
<220> FEATURE:
<223> OTHER INFORMATION: Nucleic acid sequence of primer m203-b based on
      Prochloron didemni.

<400> SEQUENCE: 255
tcaacgccat cgtacgcaca aatggtgaaa cagtaagtaa tacaaacggt tgcac         55

<210> SEQ ID NO 256
<211> LENGTH: 44
<212> TYPE: DNA
<213> ORGANISM: Artificial Sequence
<220> FEATURE:
<223> OTHER INFORMATION: Nucleic acid sequence of primer m35-N-b based
      on Prochloron didemni.

<400> SEQUENCE: 256
cgaagcttaa gatggctcaa cgccatcgta cgcgcaacaa cagc                     44

```
<210> SEQ ID NO 257
<211> LENGTH: 11
<212> TYPE: PRT
<213> ORGANISM: Artificial Sequence
<220> FEATURE:
<223> OTHER INFORMATION: An example of Recognition Sequence 2 based on
      Prochloron didemni.

<400> SEQUENCE: 257

Ala Tyr Asp Gly Val Glu Pro Ser Arg Arg Arg
1               5                   10

<210> SEQ ID NO 258
<211> LENGTH: 8
<212> TYPE: PRT
<213> ORGANISM: Artificial Sequence
<220> FEATURE:
<223> OTHER INFORMATION: An example of Recognition Sequence 2 based on
      Prochloron didemni.

<400> SEQUENCE: 258

Ala Tyr Asp Gly Val Arg Arg Arg
1               5

<210> SEQ ID NO 259
<211> LENGTH: 6
<212> TYPE: PRT
<213> ORGANISM: Artificial Sequence
<220> FEATURE:
<223> OTHER INFORMATION: An example of Recognition Sequence 2 based on
      Prochloron didemni.

<400> SEQUENCE: 259

Ala Tyr Asp Gly Val Ala
1               5

<210> SEQ ID NO 260
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 260

Met Asn Lys Lys Asn Ile Leu Pro Gln Gln Gly Gln Pro Val Ile Arg
1               5                   10                  15

Leu Thr Ala Gly Gln Leu Ser Ser Gln Ala Ala Glu Leu Ser Glu Glu
            20                  25                  30

Ala Leu Gly Asp Ala
        35

<210> SEQ ID NO 261
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 261

Met Asn Lys Lys Asn Ile Leu Pro Gln Gln Gly Gln Pro Val Ile Arg
1               5                   10                  15

Leu Thr Ala Gly Gln Leu Ser Ser Gln Asn Ala Glu Leu Ser Glu Glu
            20                  25                  30
```

Ala Leu Gly Asp Ala
        35

<210> SEQ ID NO 262
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 262

Met Asn Lys Lys Asn Ile Leu Pro Gln Gln Gly Gln Pro Val Ile Arg
1               5                   10                  15

Leu Thr Ala Gly Gln Leu Ser Ser Gln Leu Gly Glu Leu Ser Glu Glu
            20                  25                  30

Ala Leu Gly Asp Ala
        35

<210> SEQ ID NO 263
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 263

Met Asn Lys Lys Asn Ile Leu Pro Gln Gln Gly Gln Pro Val Ile Arg
1               5                   10                  15

Leu Thr Ala Gly Gln Leu Ser Ser Gln Leu Asn Glu Leu Ser Glu Glu
            20                  25                  30

Ala Leu Gly Asp Ala
        35

<210> SEQ ID NO 264
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 264

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Ala Leu Ser Glu Glu
            20                  25                  30

Ala Leu Gly Asp Ala
        35

<210> SEQ ID NO 265
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 265

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Gln Leu Ser Glu Glu

-continued

```
                20                  25                  30

Ala Leu Gly Asp Ala
        35

<210> SEQ ID NO 266
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 266

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Ala Ser Glu Glu
            20                  25                  30

Ala Leu Gly Asp Ala
        35

<210> SEQ ID NO 267
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 267

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Asn Ser Glu Glu
            20                  25                  30

Ala Leu Gly Asp Ala
        35

<210> SEQ ID NO 268
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 268

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ala Glu Glu
            20                  25                  30

Ala Leu Gly Asp Ala
        35

<210> SEQ ID NO 269
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 269

Met Asn Lys Lys Asn Ile Leu Pro Gln Gln Gly Gln Pro Val Ile Arg
1               5                   10                  15
```

-continued

Leu Thr Ala Gly Gln Leu Ser Ser Gln Leu Ala Glu Leu Ala Glu
            20                  25                  30

Ala Leu Gly Asp Ala
        35

<210> SEQ ID NO 270
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 270

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Gln Glu
            20                  25                  30

Ala Leu Gly Asp Ala
        35

<210> SEQ ID NO 271
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 271

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Ala
            20                  25                  30

Ala Leu Gly Asp Ala
        35

<210> SEQ ID NO 272
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 272

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Gln
            20                  25                  30

Ala Leu Gly Asp Ala
        35

<210> SEQ ID NO 273
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 273

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Gly Leu Gly Asp Ala
        35

<210> SEQ ID NO 274
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 274

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Asn Leu Gly Asp Ala
        35

<210> SEQ ID NO 275
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 275

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Ala Gly Asp Ala
        35

<210> SEQ ID NO 276
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 276

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Asn Gly Asp Ala
        35

<210> SEQ ID NO 277
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 277

Met Asn Lys Lys Asn Ile Leu Pro Gln Gln Gly Gln Pro Val Ile Arg

```
1               5                  10                 15
Leu Thr Ala Gly Gln Leu Ser Ser Gln Leu Ala Glu Leu Ser Glu Glu
                20                  25                  30

Ala Leu Ala Asp Ala
        35

<210> SEQ ID NO 278
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 278

Met Asn Lys Lys Asn Ile Leu Pro Gln Gln Gly Gln Pro Val Ile Arg
1               5                  10                  15

Leu Thr Ala Gly Gln Leu Ser Ser Gln Leu Ala Glu Leu Ser Glu Glu
                20                  25                  30

Ala Leu Gly Ala Ala
        35

<210> SEQ ID NO 279
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 279

Met Asn Lys Lys Asn Ile Leu Pro Gln Gln Gly Gln Pro Val Ile Arg
1               5                  10                  15

Leu Thr Ala Gly Gln Leu Ser Ser Gln Leu Ala Glu Leu Ser Glu Glu
                20                  25                  30

Ala Leu Gly Asn Ala
        35

<210> SEQ ID NO 280
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 280

Met Asn Lys Lys Asn Ile Leu Pro Gln Gln Gly Gln Pro Val Ile Arg
1               5                  10                  15

Leu Thr Ala Gly Gln Leu Ser Ser Gln Leu Ala Glu Leu Ser Glu Glu
                20                  25                  30

Ala Leu Gly Asp Gly
        35

<210> SEQ ID NO 281
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 281
```

```
Met Asn Lys Lys Asn Ile Leu Pro Gln Gln Gly Gln Pro Val Ile Arg
1               5                  10                 15

Leu Thr Ala Gly Gln Leu Ser Ser Gln Leu Ala Glu Leu Ser Glu Glu
            20                  25                 30

Ala Leu Gly Asp Asn
        35

<210> SEQ ID NO 282
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 282

Met Asn Lys Lys Asn Ile Leu Pro Gln Gln Gly Gln Pro Val Ile Arg
1               5                  10                 15

Leu Thr Ala Gly Gln Leu Ser Ser Gln Leu Ala Glu Asn Ser Glu Glu
            20                  25                 30

Gly Leu Gly Asp Ala
        35

<210> SEQ ID NO 283
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 283

Met Asn Lys Lys Asn Ile Leu Pro Gln Gln Gly Gln Pro Val Ile Arg
1               5                  10                 15

Leu Thr Ala Gly Gln Leu Ser Ser Gln Leu Ala Glu Asn Ser Glu Glu
            20                  25                 30

Asn Leu Gly Asp Ala
        35

<210> SEQ ID NO 284
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 284

Met Asn Lys Lys Asn Ile Leu Pro Gln Gln Gly Gln Pro Val Ile Arg
1               5                  10                 15

Leu Thr Ala Gly Gln Leu Ser Ser Gln Leu Ala Glu Asn Ser Glu Glu
            20                  25                 30

Ala Asn Gly Asp Ala
        35

<210> SEQ ID NO 285
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 285
```

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Gly Asn Gly Asp Ala
        35

<210> SEQ ID NO 286
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 286

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Asn Asn Gly Asp Ala
        35

<210> SEQ ID NO 287
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 287

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Asn Ser Glu Glu
            20                  25                  30

Gly Asn Gly Asp Ala
        35

<210> SEQ ID NO 288
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 288

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Asn Ser Glu Glu
            20                  25                  30

Asn Asn Gly Asp Ala
        35

<210> SEQ ID NO 289
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 289

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Gln Leu Ser Gln Glu
            20                  25                  30

Ala Leu Gly Asp Ala
        35

<210> SEQ ID NO 290
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 290

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Gln Leu Ser Glu Gln
            20                  25                  30

Ala Leu Gly Asp Ala
        35

<210> SEQ ID NO 291
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 291

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Gln Leu Ser Glu Glu
            20                  25                  30

Ala Leu Gly Asn Ala
        35

<210> SEQ ID NO 292
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 292

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Gln Gln
            20                  25                  30

Ala Leu Gly Asp Ala
        35

<210> SEQ ID NO 293
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

-continued

<400> SEQUENCE: 293

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Gln Glu
            20                  25                  30

Ala Leu Gly Asn Ala
        35

<210> SEQ ID NO 294
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 294

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Gln
            20                  25                  30

Ala Leu Gly Asn Ala
        35

<210> SEQ ID NO 295
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 295

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Gln Leu Ser Gln Gln
            20                  25                  30

Ala Leu Gly Asp Ala
        35

<210> SEQ ID NO 296
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 296

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Gln Leu Ser Gln Glu
            20                  25                  30

Ala Leu Gly Asn Ala
        35

<210> SEQ ID NO 297
<211> LENGTH: 37
<212> TYPE: PRT
<213> ORGANISM: Artificial Sequence
<220> FEATURE:
<223> OTHER INFORMATION: An example of Leader Sequence based on Prochloron didemni.

<400> SEQUENCE: 297

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Gln Leu Ser Glu Gln
            20                  25                  30

Ala Leu Gly Asn Ala
        35

<210> SEQ ID NO 298
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 298

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Gln Gln
            20                  25                  30

Ala Leu Gly Asn Ala
        35

<210> SEQ ID NO 299
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 299

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Gln Leu Ser Gln Gln
            20                  25                  30

Ala Leu Gly Asn Ala
        35

<210> SEQ ID NO 300
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 300

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Gln Asn Ser Gln Gln
            20                  25                  30

Ala Asn Gly Asp Ala
        35

<210> SEQ ID NO 301
<211> LENGTH: 37
<212> TYPE: PRT
<213> ORGANISM: Artificial Sequence
<220> FEATURE:

```
<223> OTHER INFORMATION: An example of Leader Sequence based on
      Prochloron didemni.

<400> SEQUENCE: 301

Met Asn Lys Lys Asn Ile Leu Pro Gln Gln Gly Gln Pro Val Ile Arg
1               5                   10                  15

Leu Thr Ala Gly Gln Gly Ser Ser Gln Gly Ala Glu Gly Ser Glu Glu
            20                  25                  30

Gly Leu Gly Asp Ala
        35

<210> SEQ ID NO 302
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 302

Met Asn Lys Lys Asn Ile Leu Pro Gln Gln Gly Gln Pro Val Ile Arg
1               5                   10                  15

Leu Thr Ala Gly Gln Asn Ser Ser Gln Asn Ala Glu Asn Ser Glu Glu
            20                  25                  30

Gly Leu Gly Asp Ala
        35

<210> SEQ ID NO 303
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 303

Met Asn Lys Lys Asn Ile Leu Pro Gln Gln Gly Gln Pro Val Ile Arg
1               5                   10                  15

Leu Thr Ala Gly Gln Asn Ser Ser Gln Asn Ala Glu Asn Ser Glu Glu
            20                  25                  30

Ala Leu Gly Asp Ala
        35

<210> SEQ ID NO 304
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 304

Met Asn Lys Lys Asn Ile Leu Pro Gln Gln Gly Gln Pro Val Ile Arg
1               5                   10                  15

Leu Thr Ala Gly Gln Asn Ser Ser Gln Asn Ala Glu Asn Ala Glu Glu
            20                  25                  30

Ala Leu Gly Asp Ala
        35

<210> SEQ ID NO 305
<211> LENGTH: 37
<212> TYPE: PRT
<213> ORGANISM: Artificial Sequence
```

```
<220> FEATURE:
<223> OTHER INFORMATION: An example of Leader Sequence based on
      Prochloron didemni.

<400> SEQUENCE: 305

Met Asn Lys Lys Asn Ile Leu Pro Gln Gln Gly Gln Pro Val Ile Arg
1               5                   10                  15

Leu Thr Ala Gly Gln Asn Ser Ser Gln Asn Ala Glu Asn Ala Glu Glu
            20                  25                  30

Asn Leu Gly Asp Ala
        35

<210> SEQ ID NO 306
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 306

Met Asn Lys Lys Asn Ile Leu Pro Gln Gln Gly Gln Pro Val Asn Arg
1               5                   10                  15

Leu Thr Asn Gly Gln Asn Ser Ser Gln Asn Ala Glu Leu Ser Glu Glu
            20                  25                  30

Ala Leu Gly Asp Ala
        35

<210> SEQ ID NO 307
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 307

Met Asn Lys Lys Asn Ile Leu Pro Gln Gln Gly Gln Pro Val Asn Arg
1               5                   10                  15

Leu Thr Gly Gly Gln Asn Ser Ser Gln Asn Ala Glu Leu Ser Glu Glu
            20                  25                  30

Ala Leu Gly Asp Ala
        35

<210> SEQ ID NO 308
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 308

Met Asn Lys Lys Asn Ile Leu Pro Gln Gln Gly Gln Pro Val Gly Arg
1               5                   10                  15

Leu Thr Gly Gly Gln Gly Ser Ser Gln Gly Ala Glu Leu Ser Glu Glu
            20                  25                  30

Ala Leu Gly Asp Ala
        35

<210> SEQ ID NO 309
<211> LENGTH: 37
<212> TYPE: PRT
```

<213> ORGANISM: Artificial Sequence
<220> FEATURE:
<223> OTHER INFORMATION: An example of Leader Sequence based on
      Prochloron didemni.

<400> SEQUENCE: 309

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Pro Leu Gly Asp Ala
            35

<210> SEQ ID NO 310
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 310

Met Asn Lys Lys Asn Ile Leu Pro Gln Gln Gly Gln Pro Val Ile Arg
1               5                   10                  15

Leu Thr Ala Gly Gln Leu Ser Ser Gln Leu Pro Glu Leu Ser Glu Glu
            20                  25                  30

Pro Leu Gly Asp Ala
            35

<210> SEQ ID NO 311
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 311

Met Asn Lys Lys Asn Ile Leu Pro Gln Gln Gly Gln Pro Val Ile Arg
1               5                   10                  15

Leu Thr Ala Gly Pro Leu Ser Ser Gln Leu Pro Glu Leu Ser Glu Glu
            20                  25                  30

Pro Leu Gly Asp Ala
            35

<210> SEQ ID NO 312
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 312

Met Asn Lys Lys Asn Ile Leu Pro Gln Gln Gly Gln Pro Val Ile Arg
1               5                   10                  15

Pro Thr Ala Gly Gln Pro Ser Ser Gln Leu Pro Glu Leu Ser Glu Glu
            20                  25                  30

Pro Leu Gly Asp Ala
            35

<210> SEQ ID NO 313
<211> LENGTH: 37

```
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 313

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Pro Asp Ala
            35

<210> SEQ ID NO 314
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 314

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Pro Glu Glu
            20                  25                  30

Ala Leu Gly Asp Ala
            35

<210> SEQ ID NO 315
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 315

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Pro Glu Glu
            20                  25                  30

Ala Leu Pro Asp Ala
            35

<210> SEQ ID NO 316
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 316

Met Asn Lys Lys Asn Ile Leu Pro Gln Gln Gly Gln Pro Val Ile Arg
1               5                   10                  15

Leu Thr Ala Gly Gln Leu Ser Pro Gln Leu Ala Glu Leu Pro Glu Glu
            20                  25                  30

Ala Leu Pro Asp Ala
            35

<210> SEQ ID NO 317
```

```
<211> LENGTH: 37
<212> TYPE: PRT
<213> ORGANISM: Artificial Sequence
<220> FEATURE:
<223> OTHER INFORMATION: An example of Leader Sequence based on
      Prochloron didemni.

<400> SEQUENCE: 317

Met Asn Lys Lys Asn Ile Leu Pro Gln Gln Gly Gln Pro Val Ile Arg
1               5                   10                  15

Leu Pro Ala Gly Gln Leu Ser Pro Gln Leu Ala Glu Leu Pro Glu Glu
            20                  25                  30

Ala Leu Pro Asp Ala
        35

<210> SEQ ID NO 318
<211> LENGTH: 5
<212> TYPE: PRT
<213> ORGANISM: Artificial Sequence
<220> FEATURE:
<223> OTHER INFORMATION: An example of Recognition Sequence based on
      Prochloron didemni.

<400> SEQUENCE: 318

Ala Tyr Asp Gly Glu
1               5

<210> SEQ ID NO 319
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 319
ggtttggaag catctgtaac tgcttgcatc acttttttgcg cttatgatgg tgtggagcca      60
tctataactg tttgcatcag tgtttgcgct tatgatggtg aataa                      105

<210> SEQ ID NO 320
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 320
ggtttggaag catctttaac tgcttgcatc acttttttgcg cttatgatgg tgtggagcca     60
tctataactg tttgcatcag tgtttgcgct tatgatggtg aataa                     105

<210> SEQ ID NO 321
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 321
ggtttggaag catctttaac tacttgcatc acttttttgcg cttatgatgg tgtggagcca    60
tctataactg tttgcatcag tgtttgcgct tatgatggtg aataa                    105

<210> SEQ ID NO 322
<211> LENGTH: 105
<212> TYPE: DNA
<213> ORGANISM: Artificial Sequence
```

<220> FEATURE:
<223> OTHER INFORMATION: DNA sequence based on Prochloron didemni.

<400> SEQUENCE: 322
ggtttggaag catctttaac tgcttgcgtc acttttttgcg cttatgatgg tgtggagcca    60
tctataactg tttgcatcag tgtttgcgct tatgatggtg aataa                    105

<210> SEQ ID NO 323
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 323
ggtttggaag catctttaac tgcttgcatc acttttttgcg cttatgatgg tgtggagcca    60
tctataactg tttgcatcac tgtttgcgct tatgatggtg aataa                    105

<210> SEQ ID NO 324
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 324
ggtttggaag catctttagc tgcttgcatc acttttttgcg cttatgatgg tgtggagcca    60
tctataactg tttgcatcag tgtttgcgct tatgatggtg aataa                    105

<210> SEQ ID NO 325
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 325
ggtttggaag catctttaac tgcttgcatc acttctttgcg cttatgatgg tgtggagcca    60
tctataactg tttgcatcag tgtttgcgct tatgatggtg aataa                    105

<210> SEQ ID NO 326
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 326
ggtttggaag catctttaac tgcttgcatc acttttttgcg cttatgatgg tgtggagcca    60
tctataactg tttgcatcag tgcttgcgct tatgatggtg aataa                    105

<210> SEQ ID NO 327
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 327
ggtttggaag catctttaac tgcttgcatc acttttttgcg cttatgatgg tgtggagcca    60
tctagcactg tttgcttcac tgtttgtgct tatgatggtg aataa                    105

-continued

<210> SEQ ID NO 328
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 328

```
ggtttggaag catctgtaac tgcttgcatc acttttttgcg cttatgatgg tgtggagcca    60
tcatgcacct tatgctgtac cttatgtgct tacgatggtg aataa                    105
```

<210> SEQ ID NO 329
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 329

```
ggtttggaag catctttaac tgcttgcatc acttttttgcg cttatgatgg tgtggagcca    60
tcatgcacct tatgctgtac cttatgtgct tacgatggtg aataa                    105
```

<210> SEQ ID NO 330
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 330

```
ggtttggaag catctgtagc tgcttgcatc acttttttgcg cttatgatgg tgtggagcca    60
tcatgcacct tatgctgtac cttatgtgct tacgatggtg aataa                    105
```

<210> SEQ ID NO 331
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 331

```
ggtttggaag catctgtaac tgcttgcatc acttttttgcg cttatgatgg tgtggagcca    60
tcatgcacct tatgctgtac cttacgtgct tacgatggtg aataa                    105
```

<210> SEQ ID NO 332
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 332

```
ggtttggaag catctgtaac tgcttgcatc gcttttttgcg cttatgatgg tgtggagcca    60
tcatgcacct tatgctgtac cttatgtgct tacgatggtg aataa                    105
```

<210> SEQ ID NO 333
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 333

```
ggtttggaag catctgtaac tgcttgcatc acttcttgcg cttatgatgg tgtggagcca      60
tcatgcacct tatgctgtac cttatgtgct tacgatggtg aataa                    105
```

<210> SEQ ID NO 334
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 334

```
ggtttggaag catctgtaac tgcttgcatc actctttgcg cttatgatgg tgtggagcca      60
tcatgcacct tatgctgtac cttatgtgct tacgatggtg aataa                    105
```

<210> SEQ ID NO 335
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 335

```
ggtttggaag catctgtaac tacttgcatc acttttttgcg cttatgatgg tgtggagcca     60
tcatgcacct tatgctgtac cttatgtgct tacgatggtg aataa                    105
```

<210> SEQ ID NO 336
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 336

```
ggtttggaag catctgtaac tgcttgcatc acttttttgcg cttatgatgg tgtggagcca     60
tcatgcatct tatgctgtac cttatgtgct tacgatggtg aataa                    105
```

<210> SEQ ID NO 337
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 337

```
ggtttggaag catctgtaac tgcttgcacc acttttttgcg cttatgatgg tgtggagcca     60
ccatgcacct tatgctgtac cttatgtgct tacgatggtg aataa                    105
```

<210> SEQ ID NO 338
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 338

```
ggtttggaag catctgtaac tgcttgcatc acttttttgcg cttatgatgg tgtggagcca     60
tcatgcacct tatgctgtgc cttatgtgct tacgatggtg aataa                    105
```

<210> SEQ ID NO 339
<211> LENGTH: 105
<212> TYPE: DNA

```
<213> ORGANISM: Artificial Sequence
<220> FEATURE:
<223> OTHER INFORMATION: DNA sequence based on Prochloron didemni.

<400> SEQUENCE: 339
ggtttggaag catctgtaac tgcttgcatc acttttttgcg cttatgatgg tgtggagcca    60
tcatgcacct tatgctgtac cgtatgtgct tacgatggtg aataa                  105

<210> SEQ ID NO 340
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 340
ggtttggaag catctgtaac tgcttgcatc acttttttgcg cttatgatgg tgtggagcca    60
tcatgcacct tatgctgtac cttctgtgct tacgatggtg aataa                  105

<210> SEQ ID NO 341
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 341
ggtttggaag catctgtaac tgcttgcatc acttttttgcg cttatgatgg tgtggagcca    60
tcatgcaccg tatgctgtgc cgtatgtgct tacgatggtg aataa                  105

<210> SEQ ID NO 342
<211> LENGTH: 105
<212> TYPE: DNA
<213> ORGANISM: Artificial Sequence
<220> FEATURE:
<223> OTHER INFORMATION: DNA sequence based on Prochloron didemni.

<400> SEQUENCE: 342
ggtttggaag catctgtaac tgcttgcatc acttttttgcg cttatgatgg tgtggagcca    60
tcatgcacct tatgctatac cttatgtgct tacgatggtg aataa                  105

<210> SEQ ID NO 343
<211> LENGTH: 99
<212> TYPE: DNA
<213> ORGANISM: Artificial Sequence
<220> FEATURE:
<223> OTHER INFORMATION: DNA sequence based on Prochloron didemni.

<400> SEQUENCE: 343
ggtttggaag catctgcctg ttttcccact atttgcgctt atgatggtgt ggagccatct    60
ttctgttttc ccactgtttg cgcctatgat ggtgaataa                          99

<210> SEQ ID NO 344
<211> LENGTH: 99
<212> TYPE: DNA
<213> ORGANISM: Artificial Sequence
<220> FEATURE:
<223> OTHER INFORMATION: DNA sequence based on Prochloron didemni.

<400> SEQUENCE: 344
ggtttggaag catctgcctg ttttcccact atttgcgctt atgatggtgt ggagccatct    60
ctctgttttc ccactgtttg cgcctatgat ggtgaataa                          99
```

<210> SEQ ID NO 345
<211> LENGTH: 99
<212> TYPE: DNA
<213> ORGANISM: Artificial Sequence
<220> FEATURE:
<223> OTHER INFORMATION: DNA sequence based on Prochloron didemni.

<400> SEQUENCE: 345
ggtttggaag catctgcctg ttttcccact atttgcgctt atgatggtgt ggagccatct    60
ttctgtgttc ccactgtttg cgcctatgat ggtgaataa                           99

<210> SEQ ID NO 346
<211> LENGTH: 99
<212> TYPE: DNA
<213> ORGANISM: Artificial Sequence
<220> FEATURE:
<223> OTHER INFORMATION: DNA sequence based on Prochloron didemni.

<400> SEQUENCE: 346
ggtttggaag catctgcctg ttttcccact atttgcgctt atgatggtgt ggagccatct    60
ttctgttttc ccgctgtttg cgcctatgat ggtgaataa                           99

<210> SEQ ID NO 347
<211> LENGTH: 99
<212> TYPE: DNA
<213> ORGANISM: Artificial Sequence
<220> FEATURE:
<223> OTHER INFORMATION: DNA sequence based on Prochloron didemni.

<400> SEQUENCE: 347
ggtttggaag catctgcctg ttttcccact atttgcgctt atgatggtgt ggagccatct    60
ttctgtcttc ccactgtttg cgcctatgat ggtgaataa                           99

<210> SEQ ID NO 348
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 348

Ile Thr Val Cys Ile Ser Val Cys
1               5

<210> SEQ ID NO 349
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 349

Leu Thr Ala Cys Ile Thr Phe Cys
1               5

<210> SEQ ID NO 350
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

```
<400> SEQUENCE: 350

Val Ala Ala Cys Ile Thr Phe Cys
1               5

<210> SEQ ID NO 351
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 351

Leu Thr Thr Cys Ile Thr Phe Cys
1               5

<210> SEQ ID NO 352
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 352

Leu Thr Ala Cys Val Thr Phe Cys
1               5

<210> SEQ ID NO 353
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 353

Ile Thr Val Cys Ile Thr Val Cys
1               5

<210> SEQ ID NO 354
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 354

Leu Ala Ala Cys Ile Thr Phe Cys
1               5

<210> SEQ ID NO 355
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 355

Leu Thr Ala Cys Ile Thr Leu Cys
1               5

<210> SEQ ID NO 356
<211> LENGTH: 8
```

```
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 356

Ile Thr Val Cys Ile Ser Ala Cys
1               5

<210> SEQ ID NO 357
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 357

Ser Thr Val Cys Phe Thr Val Cys
1               5

<210> SEQ ID NO 358
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 358

Val Thr Ala Cys Ile Ala Phe Cys
1               5

<210> SEQ ID NO 359
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 359

Val Thr Ala Cys Ile Thr Ser Cys
1               5

<210> SEQ ID NO 360
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 360

Val Thr Ala Cys Ile Thr Leu Cys
1               5

<210> SEQ ID NO 361
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 361

Val Thr Thr Cys Ile Thr Phe Cys
```

```
<210> SEQ ID NO 362
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 362

Val Thr Ala Cys Thr Thr Phe Cys
1               5

<210> SEQ ID NO 363
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 363

Cys Thr Leu Cys Cys Thr Leu Cys
1               5

<210> SEQ ID NO 364
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 364

Cys Thr Leu Cys Cys Thr Leu Arg
1               5

<210> SEQ ID NO 365
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 365

Cys Ile Leu Cys Cys Thr Leu Cys
1               5

<210> SEQ ID NO 366
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 366

Cys Thr Leu Cys Cys Ala Leu Cys
1               5

<210> SEQ ID NO 367
<211> LENGTH: 8
<212> TYPE: PRT
<213> ORGANISM: Artificial Sequence
<220> FEATURE:
<223> OTHER INFORMATION: Amino acid sequence of natural cassette domain
``` based on Prochloron didemni.

<400> SEQUENCE: 367

Cys Thr Leu Cys Cys Thr Val Cys
1               5

<210> SEQ ID NO 368
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 368

Cys Thr Leu Cys Cys Thr Phe Cys
1               5

<210> SEQ ID NO 369
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 369

Cys Thr Val Cys Cys Ala Val Cys
1               5

<210> SEQ ID NO 370
<211> LENGTH: 8
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 370

Cys Thr Leu Cys Tyr Thr Leu Cys
1               5

<210> SEQ ID NO 371
<211> LENGTH: 7
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 371

Ala Cys Phe Pro Thr Ile Cys
1               5

<210> SEQ ID NO 372
<211> LENGTH: 7
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 372

Phe Cys Phe Pro Thr Val Cys
1               5

<210> SEQ ID NO 373

```
<211> LENGTH: 7
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 373

Leu Cys Phe Pro Thr Val Cys
1               5

<210> SEQ ID NO 374
<211> LENGTH: 7
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 374

Phe Cys Val Pro Thr Val Cys
1               5

<210> SEQ ID NO 375
<211> LENGTH: 7
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 375

Phe Cys Phe Pro Ala Val Cys
1               5

<210> SEQ ID NO 376
<211> LENGTH: 7
<212> TYPE: PRT
<213> ORGANISM: Artificial Sequence
<220> FEATURE:
<223> OTHER INFORMATION: Amino acid sequence of natural cassette domain
      based on Prochloron didemni.

<400> SEQUENCE: 376

Phe Cys Leu Pro Thr Val Cys
1               5
```

The invention claimed is:

1. A method of constructing an azoline compound library containing two or more azoline compounds having an azoline backbone introduced into at least one of Cys, Ser, Thr, and 2,3-diamino acid, and analogs thereof of $Xaa_0$ of a peptide comprising a sequence represented by $-(Xaa_0)_m-$, wherein m is an integer selected from 2 to 40, and each $Xaa_0$ is an arbitrary amino acid, at least one of which is an amino acid that forms an azoline ring in the presence of heterocyclase and comprises the structural formula (II):

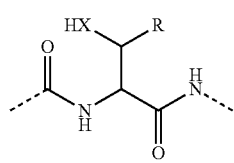

(II)

wherein R represents a hydrogen atom, a substituted or unsubstituted alkyl group having from 1 to 10 carbon atoms, or a substituted or unsubstituted aromatic group, X is O, S, or NH, comprising:

constructing an mRNA library encoding a plurality of precursor peptides, each precursor peptide independently comprising $-(Xaa_0)_m-$, which is a patellamide C cassette domain modified to have one or more amino acid substitutions, deletions, and/or additions, and each precursor peptide independently and optionally comprises a recognition sequence 1 at its N-terminus, a recognition sequence 2 at its C-terminus, or both, and wherein the recognition sequences are recognized by the azoline backbone introducing enzyme;

expressing the plurality of precursor peptides in a cell-free translation system by using the mRNA library and thereby constructing a peptide library; and reacting the azoline backbone-introducing enzyme and the peptide library, optionally in the presence a leader sequence of a substrate of the azoline backbone-introducing enzyme, and thereby introducing the azoline backbone into $(Xaa_O)_m$, wherein the leader sequence is present where the recognition sequences are absent.

2. The method of constructing an azoline compound library according to claim 1, wherein in the step of expressing the plurality of precursor peptides, each mRNA is bound to puromycin at its 3' end prior to expressing each precursor peptide and thereby constructing a peptide library comprising peptide-mRNA complexes.

3. The method of constructing an azoline compound library according to claim 1, wherein:

$(Xaa_O)_m$- includes -$(Xaa_1-Xaa_2)_n$- wherein n represents an integer selected from 1 to 20, and $Xaa_2$ comprises the structural formula (II).

4. The method according to claim 1, wherein at least one of the peptides of the peptide library is a peptide represented by any of SEQ ID NOS: 10 to 57.

5. The method according to claim 1, wherein the leader sequence is provided as a fusion peptide, wherein the leader sequence is fused to a precursor peptide of the plurality of precursor peptides, said precursor peptide comprising a recognition sequence 1, -$(Xaa_O)_m$-, and a recognition sequence 2.

6. The method according to claim 1, wherein the leader sequence is not fused to the substrate of the azoline backbone-introducing enzyme.

7. The method according to claim 1, further comprising macrocyclizing the azoline compound.

8. A method of constructing an azole compound library, comprising, after the step of introducing an azoline backbone in the method of constructing an azoline compound library according to claim 1, reacting the library having an azoline backbone introduced therein with an azole backbone-introducing enzyme in the presence or absence of a peptide comprising a leader sequence of a substrate of the azole backbone-introducing enzyme and converting at least one of the azoline backbones into an azole backbone.

9. A screening method for identifying an azoline compound that binds to a target substance, comprising:

constructing an azoline compound library containing two or more azoline compounds having an azoline backbone introduced into at least one of Cys, Ser, Thr, and 2,3-diamino acid, and analogs thereof of $Xaa_O$ of a peptide comprising a sequence represented by -$(Xaa_O)_m$-, wherein m is an integer selected from 2 to 40, and each $Xaa_O$ is an arbitrary amino acid, at least one of which is an amino acid that forms an azoline ring in the presence of heterocyclase and comprises the structural formula (II):

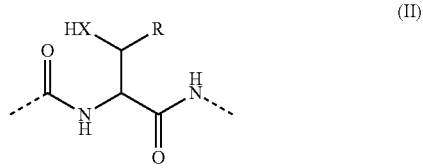

wherein R represents a hydrogen atom, a substituted or unsubstituted alkyl group having from 1 to 10 carbon atoms, or a substituted or unsubstituted aromatic group, X is O, S, or NH, by:

constructing an mRNA library encoding a plurality of precursor peptides, each precursor peptide independently comprising -$(Xaa_O)_m$-, which is a patellamide C cassette domain modified to have one or more amino acid substitutions, deletions, and/or additions, and each precursor peptide independently and optionally comprises a recognition sequence 1 at its N-terminus, a recognition sequence 2 at its C-terminus, or both, and wherein the recognition sequences are recognized by the azoline backbone introducing enzyme;

expressing the plurality of precursor peptides in a cell-free translation system by using the mRNA library and thereby constructing a peptide library; and reacting the azoline backbone-introducing enzyme and the peptide library, optionally in the presence a leader sequence of a substrate of the azoline backbone-introducing enzyme, and thereby introducing the azoline backbone into $(Xaa_O)_m$, wherein the leader sequence is present where the recognition sequences are absent;

bringing the azoline compound library into contact with a target substance, followed by incubation, and selecting the azoline compound that has bound to the target substance.

10. The screening method according to claim 9, wherein in the step of expressing the plurality of precursor peptides, each mRNA is bound to puromycin at its 3' end prior to expressing each precursor peptide and thereby constructing a peptide library comprising peptide-mRNA complexes, and further comprising:

analyzing the base sequence of the mRNA of the azoline compound thus selected.

11. A method of preparing an azoline compound having an azoline backbone introduced into at least one of Cys, Ser, Thr, and 2,3-diamino acid, and analogs thereof of $Xaa_O$ of a peptide comprising a sequence represented by -$(Xaa_O)_m$-, wherein m is an integer selected from 2 to 40, and each $Xaa_O$ is an arbitrary amino acid, at least one of which is an amino acid that forms an azoline ring in the presence of azoline backbone-introducing enzyme and comprises the structural formula (II):

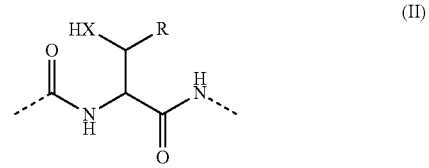

wherein R represents a hydrogen atom, a substituted or unsubstituted alkyl group having from 1 to 10 carbon atoms, or a substituted or unsubstituted aromatic group, X is O, S, or NH, comprising:

preparing an mRNA encoding a precursor peptide comprising -$(Xaa_O)_m$-, which is a patellamide C cassette domain modified to have one or more amino acid substitutions, deletions, and/or additions, said precursor polypeptide optionally comprising a recognition sequence 1 at its N-terminus, a recognition sequence 2 at its C-terminus, or both, and wherein the recognition sequences are recognized by the azoline backbone introducing enzyme, and wherein at least one $Xaa_O$ of the precursor peptide is a noncanonical amino acid;

expressing the precursor peptide in a cell-free translation system by using the mRNA; and reacting the azoline backbone-introducing enzyme and the precursor peptide in the presence of a leader sequence of a substrate of the azoline backbone-introducing enzyme and thereby introducing an azoline backbone into $(Xaa_0)_m$, wherein the substrate with the leader sequence is separate from the precursor peptide.

12. The method according to claim 1, wherein the peptide comprises up to 100 amino acids at its N-terminus and up to 100 amino acids at its C-terminus.

13. The method according to claim 1, wherein the peptide comprises 2-70 amino acids at its N-terminus and up to 30 amino acids at its C-terminus.

14. The method according to claim 1, wherein the recognition sequence 1 comprises up to 10 amino acids.

15. The method according to claim 1, wherein the recognition sequence 2 comprises up to 10 amino acids.

16. The method according to claim 1, wherein the leader sequence comprises up to 50 amino acids.

* * * * *